(12) United States Patent
Chang et al.

(10) Patent No.: US 8,703,129 B2
(45) Date of Patent: Apr. 22, 2014

(54) ANTIBODIES AGAINST EXTENDED TYPE 1 CHAIN ANTIGENS, DERIVATIVES THEREOF AND USE

(75) Inventors: Tong-Hsuan Chang, Taipei (TW); Jerry Ting, Taipei (TW); Mei-Chin Yang, Taipei (TW); Liahng-Yirn Liu, Taipei (TW); Shu-Yen Chang, New Taipei (TW); Chia-Hao Chang, New Taipei (TW)

(73) Assignee: GlycoNex, Inc., New Taipei (TW)

( * ) Notice: Subject to any disclaimer, the term of this patent is extended or adjusted under 35 U.S.C. 154(b) by 0 days.

(21) Appl. No.: 13/433,881

(22) Filed: Mar. 29, 2012

(65) Prior Publication Data

US 2012/0184717 A1 Jul. 19, 2012

Related U.S. Application Data

(63) Continuation-in-part of application No. 12/299,013, filed as application No. PCT/US2008/075533 on Sep. 7, 2008, now Pat. No. 8,163,497.

(51) Int. Cl.
*A61K 39/395* (2006.01)
*G01N 33/53* (2006.01)
*A61K 39/21* (2006.01)
*C07K 16/00* (2006.01)
*C07K 16/28* (2006.01)

(52) U.S. Cl.
USPC . 424/130.1; 435/7.1; 530/387.1; 530/388.22; 424/137.1

(58) Field of Classification Search
None
See application file for complete search history.

(56) References Cited

U.S. PATENT DOCUMENTS

| | | | |
|---|---|---|---|
| 6,083,929 A | 7/2000 | Stroud | |
| 6,294,523 B1 | 9/2001 | Stroud | |
| 6,432,402 B1 | 8/2002 | Chapman | |
| 7,041,870 B2 | 5/2006 | Tomizuka | |
| 7,115,717 B2 | 10/2006 | Mori | |
| 8,163,497 B2 * | 4/2012 | Chang et al. | 435/7.1 |

FOREIGN PATENT DOCUMENTS

| | | | |
|---|---|---|---|
| WO | WO2010/027364 | * | 11/2010 |
| WO | WO 2011/063980 | | 6/2011 |

OTHER PUBLICATIONS

Reiss et al. ition of platelet aggregation by grafting RGD and KGD sequences on the structural scaffold of small disulfide-rich proteins. Platelets 17(3):153-157, 2006.*
Yang et al. Human monoclonal antibody GNX-8 directed to extended type 1 chain: Specific binding to human colorectal cancer. Int J Cancer. Dec. 21, 2009, pp. 1-39.*
Yang et al., "Human Monolonal Antibody GNX-8 Directed to Extended Type 1 Chain: Specific Binding to Human Colorectal Cancer," International Journal of Cancer, pp. 1-39, 2009.
Tomizuka et al., "Double trans-chromosomic mice . . . human antibodies," PNAS 97: 722-727 (2000).
Motoki et al., "Enhanced apoptosis . . . ligand receptor 2," Clin Cancer Res 11:3126-3135 (2005).
Nozawa e al., "HMMC-1 . . . duct-related carcinomas," Clin Cancer Res 51:7071-7078 (2004).
Watanabe et al., "In vitro and in vivo . . . epitope," Cancer Res 51:2199-2204 (1991).
Suzuki et al., "MHOCC-1, a human . . . mesothelial cells," Gyn Oncol 95:290-298 (2004).
Ito et al., "Specificity and . . . chain antigen," Canc Res 52:3739-3745 (1992).
Finstad et al., "Distribution of . . . ovarian cancer," Clin Canc Res 3:1433-1442 (1997).
Suzuki et al., "Human monoclonal antibody . . . CA125-like antigen," Int J Gyn Canc 1-11 (2007).
Tawara et al., "Fully human antibody . . . lymphomas" Cancer Sci 98:921-928 (2007).
Stroud et al., "Extended Type I . . . Antigen" JBC 266:8436-8446 (1991).
Stroud et al., "Extended Type-1 . . . antigens" Eur J Biochem 203: 577-586 (1992).
Hakomori et al., "Glycosylation defining . . . in an old bottle" PNAS 99:10231-10233 (2002).
Rudikoff et al., "Single Amino Acid Substitution Altering Antigen-Binding Specificity," PNAS 79(6):1979-1983 (1982).
Stroud et al., Extended Type 1 Chain Glycosphingolipids Lea-Lea (dimeric Lea) and Leb-Lea as Human Tumor Associated Antigens, in Carbohydrate Antigens, Garegg, P., et al., ACS Symposium Series; American Chemical Society: Washington DC, pp. 159-175 (1993).
Shibaguchi et al., Cloning and Sequencing of Variable Region cDNAs of a Novel Human Monoclonal Anitibody to Carcinoembryonic Antigen, and Generation of a Single Chain Variable Fragmented Antibody, Anticancer Research, 24: 3355-3360 (2004).
Imakiire et al., "Generation, Immunologic Characterization and Antitumor Effects of Human Monoclonal Antibodies for Carcinoembryonic Antigen," Int J. Cancer, 108:564-570 (2004).
Brown et al., Tolerance of single, but not multiple, amino acid replacements in antibody VH CDR 2: a means of minimizing B cell wastage from somatic hypermutation, J. Immuno. 3285-3291 (1996).
Vajdos et al., Comprehensive Functional Maps of the Antigen-Binding Site of an Anti-ErbB2 Antibody obtained with shotgun scanning mutagenesis, J. Mol. Biol. 320(2):415-428 (2002).
Eduardo Padian, "Anatomy of the antibody molecule," Mol. Immunol. 31(3):169-217 (1994).
Paul, "Fundamental Immunology," 3rd Edition, pp. 292-295 (1993).

* cited by examiner

*Primary Examiner* — Maher Haddad
(74) *Attorney, Agent, or Firm* — Cesari and McKenna, LLP

(57) ABSTRACT

Disclosed herein are antibodies or antigen-binding portions thereof directed against extended Type I chain antigens, in particular extended Type I chain glycosphingolipids, and the uses of the antibodies or antigen-binding portions thereof in the diagnosis, amelioration, treatment or prevention of diseases or disorders in mammals, including humans, resulting from or associated with the improper activity/metabolism or the presence of extended Type I chain antigens, in particular extended Type I chain glycosphingolipids.

14 Claims, 4 Drawing Sheets

SEQUENCE LISTING

<160> NUMBER OF SEQ ID NOS: 44

<210> SEQ ID NO 1
<211> LENGTH: 5
<212> TYPE: PRT
<213> ORGANISM: Homo sapiens

<400> SEQUENCE: 1

Glu Leu Leu Gly Gly
1               5

<210> SEQ ID NO 2
<211> LENGTH: 5
<212> TYPE: PRT
<213> ORGANISM: Homo sapiens

<400> SEQUENCE: 2

Met Ile Ser Arg Thr
1               5

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcatgtacta gttttgtcac aagatttggg                                    30

<210> SEQ ID NO 4
<211> LENGTH: 26

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgcacgccg ctggtcaggg cgcctg                                            26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtgccaggg ggaagaccga tgg                                               23

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgaattcacc atggctgtct ccttcctc                                          28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctctagatc atttacccgg agacagg                                           27

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actcccagtt caattacagc                                                   20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggtttgtcc aaactcatc                                                    19

<210> SEQ ID NO 10
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 10
gcatgtacta gttttgtcac aagatttggg                                        30

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttttcccag tcacgac                                                      17

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgaattcac catggcctgg acttcac                                           27

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gccgtacgta ggacagtgac cttggttc                                          28

<210> SEQ ID NO 14
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ggactggtga agccctcgca gaccctctca ctcacctgtg ccatctccgg ggacagtgtc        60
tctagcaaga gtgttgcttg gaactggatc aggcagtccc cattgagagg ccttgagtgg      120
ctgggaagga catactacag gtccaagtgg tataatgaat atgcagtatc tgtgaaaagt      180
cgaataacca tcaatccaga cacatccaag aaccagttct ccctgcacct gaactctgtg      240
actcccgagg acacggctgt gtattactgt gcaagaaact ttgactactg gggccaggga      300
accctggtca ccgtctcc                                                    318

<210> SEQ ID NO 15
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15
```

Gly Leu Val Lys Pro Ser Gln Thr Leu Ser Leu Thr Cys Ala Ile Ser
1               5                   10                  15

Gly Asp Ser Val Ser Ser Lys Ser Val Ala Trp Asn Trp Ile Arg Gln
            20                  25                  30

Ser Pro Leu Arg Gly Leu Glu Trp Leu Gly Arg Thr Tyr Tyr Arg Ser
        35                  40                  45

Lys Trp Tyr Asn Glu Tyr Ala Val Ser Val Lys Ser Arg Ile Thr Ile
50                  55                  60

Asn Pro Asp Thr Ser Lys Asn Gln Phe Ser Leu His Leu Asn Ser Val
65                  70                  75                  80

Thr Pro Glu Asp Thr Ala Val Tyr Tyr Cys Ala Arg Asn Phe Asp Tyr
                85                  90                  95

Trp Gly Gln Gly Thr Leu Val Thr Val Ser
            100                 105

<210> SEQ ID NO 16
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ctcaccacag cacctggtgg aacagtcata ctcacttgtc gctcaagtac tggggctgtt      60
acaactaata actatgccaa ctgggtccaa gaaaaaccag atcatttatt cactggtcta    120
atagatgcta ccagcaaccg agttccaggt gttcctgtca gattctccgg ctccctgatt    180
ggagacaagg ctgccctcac catcacaggg gcacagactg aggatgatgc aatgtatttc    240
tgtgctctat ggtacaacac ccatttgtt ttcggcggtg aaccaaggt cactgtccta    300

<210> SEQ ID NO 17
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Thr Thr Ala Pro Gly Gly Thr Val Ile Leu Thr Cys Arg Ser Ser
1               5                   10                  15

Thr Gly Ala Val Thr Thr Asn Asn Tyr Ala Asn Trp Val Gln Glu Lys
            20                  25                  30

Pro Asp His Leu Phe Thr Gly Leu Ile Asp Ala Thr Ser Asn Arg Val
        35                  40                  45

Pro Gly Val Pro Val Arg Phe Ser Gly Ser Leu Ile Gly Asp Lys Ala
50                  55                  60

Ala Leu Thr Ile Thr Gly Ala Gln Thr Glu Asp Asp Ala Met Tyr Phe
65                  70                  75                  80

Cys Ala Leu Trp Tyr Asn Thr His Phe Val Phe Gly Gly Gly Thr Lys
                85                  90                  95

Val Thr Val Leu
            100

<210> SEQ ID NO 18
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 18

Gly Asp Ser Val Ser Ser Lys Ser Val Ala
1               5                   10

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggggacagtg tctctagcaa gagtgttgct                                      30

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Tyr Tyr Arg Ser Lys Trp Tyr Asn
1               5

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
acatactaca ggtccaagtg gtataat                                         27

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Arg Asn Phe Asp Tyr
1               5

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcaagaaact ttgactac                                                   18

<210> SEQ ID NO 24
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 24

Thr Gly Ala Val Thr Thr Asn Asn Tyr
1               5

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
actggggctg ttacaactaa taactat                                         27

<210> SEQ ID NO 26
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Thr Ser
1

<210> SEQ ID NO 27
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 gctaccagc                                                              9

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Leu Trp Tyr Asn Thr His Phe Val
1               5

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gctctatggt acaacaccca ttttgtt                                         27

<210> SEQ ID NO 30
<211> LENGTH: 106
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Leu Val Lys Pro Ser Gln Thr Leu Ser Leu Thr Cys Thr Ile Ser
1               5                   10                  15

Gly Asp Ser Val Ser Ser Asn Thr Val Ala Trp Asn Trp Ile Arg Gln
            20                  25                  30

Ser Pro Ser Arg Gly Leu Glu Trp Leu Gly Arg Thr Tyr Tyr Arg Ser
        35                  40                  45

Lys Trp Tyr Asn Asp Tyr Ala Ile Phe Val Lys Ser Arg Ile Thr Phe
    50                  55                  60

Asn Pro Asp Thr Ser Lys Asn Gln Phe Ser Leu His Leu Asn Ser Val
65                  70                  75                  80

Thr Pro Glu Asp Thr Ala Val Tyr Tyr Cys Ala Arg Asn Phe Asp Ser
                85                  90                  95

Trp Gly Gln Gly Thr Leu Val Thr Val Ser
            100                 105

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Asp Ser Val Ser Ser Asn Thr Val Ala
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Tyr Tyr Arg Ser Lys Trp Tyr Asn
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Asn Phe Asp Ser
1               5

<210> SEQ ID NO 34
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 34

Leu Thr Thr Ser Pro Gly Gly Thr Val Ile Leu Thr Cys Arg Ser Ser
1               5                   10                  15

Thr Gly Ala Val Thr Thr Asp Asn Tyr Ala Asn Trp Val Gln Glu Lys
            20                  25                  30

Pro Asp His Leu Phe Thr Gly Leu Ile Asp Ala Thr Ser Asn Arg Val
        35                  40                  45

Pro Gly Val Pro Val Arg Phe Ser Gly Ser Leu Ile Gly Asp Lys Ala
    50                  55                  60

Ala Leu Thr Ile Thr Gly Ala Gln Thr Glu Asp Asp Ala Met Tyr Phe
65                  70                  75                  80

Cys Ala Leu Trp Tyr Asn Thr His Phe Val Phe Gly Gly Thr Lys
                85                  90                  95

Val Thr Val Leu
            100

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Gly Ala Val Thr Thr Asp Asn Tyr
1               5

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Thr Ser
1

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Leu Trp Tyr Asn Thr His Phe Val
1               5

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgaattcacc atggctgtct ccttcctc                                        28

<210> SEQ ID NO 39

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtgcacgccg ctggtcaggg cgcctg                                          26

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcgaattcac catggcctgg acttcac                                         27

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gccgtacgta ggacagtgac cttggtta                                        28

<210> SEQ ID NO 42
<211> LENGTH: 10
<212> TYPE: PRT
<213> ORGANISM: Artificial sequence
<220> FEATURE:
<223> OTHER INFORMATION: Synthetic peptie
<220> FEATURE:
<221> NAME/KEY: MISC_FEATURE
<222> LOCATION: (7)..(7)
<223> OTHER INFORMATION: Xaa = Asn or Lys
<220> FEATURE:
<221> NAME/KEY: MISC_FEATURE
<222> LOCATION: (8)..(8)
<223> OTHER INFORMATION: Xaa = Thr or Ser

<400> SEQUENCE: 42

Gly Asp Ser Val Ser Ser Xaa Xaa Val Ala
1               5                   10

<210> SEQ ID NO 43
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa = Ser or Tyr

<400> SEQUENCE: 43

Ala Arg Asn Phe Asp Xaa
1               5

<210> SEQ ID NO 44
<211> LENGTH: 9
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa = Asp or Asn

<400> SEQUENCE: 44

Thr Gly Ala Val Thr Thr Xaa Asn Tyr
1               5
```

ANTIBODIES AGAINST EXTENDED TYPE 1 CHAIN ANTIGENS, DERIVATIVES THEREOF AND USE

CROSS-REFERENCE TO RELATED APPLICATIONS

This application is a continuation-in-part application of U.S. patent application Ser. No. 12/299,013, filed on Dec. 19, 2008, which is a U.S. National Stage Application of International Patent Application No. PCT/US2008/075533, filed on Sep. 7, 2008 and published as WO 2010/027364 A1 on Mar. 11, 2010. To the extent appropriate, a claim of priority is made to each of the applications disclosed above.

All of the foregoing related applications, as well as all documents cited or referenced therein or during their prosecution, are incorporated herein by reference in their entireties.

BACKGROUND OF THE INVENTION

1. Field of the Invention

The present invention relates to antibodies or antigen-binding portions thereof directed against extended Type I chain antigens, in particular extended Type I chain glycosphingolipids, and the uses of said antibodies or antigen-binding portions thereof in the amelioration, treatment or prevention of diseases or disorders in mammals, including humans, resulting from or associated with the improper activity/metabolism or the presence of extended Type I chain antigens, in particular extended Type I chain glycosphingolipids, for example, in a cancer (such as colorectal cancer) or other pathology.

An antibody of interest can be used for therapeutic purposes or diagnostic purposes. Thus, prophylactic, immunotherapeutic and diagnostic compositions comprising the antibodies and derivatives thereof of interest and their uses in methods for preventing or treating, or diagnosing diseases in mammals, including humans, caused by inappropriate metabolism and/or expression of extended Type I chain antigens, in particular extended Type I chain glycosphingolipids in and on cells, such as certain malignant cells, also are disclosed.

2. Description of the Related Art

Extended Type I glycosphingolipid is a cell surface molecule that may be associated with, for example, certain malignant states.

Aberrant glycosylation has been observed to be a common feature of many cancer types (S. Hakomori, *PNAS*, 99:10231-10233, 2002). Some of the carbohydrate antigens used for the diagnosis of human cancers carry polylactosamine structures. Polylactosamines are usually classified into two categories according to the unit structure. A polylactosamine having the Gal$\beta$1→3GlcNAc structure is called a Type I chain, and that having the Gal$\beta$1→4GlcNAc structure is referred to as a Type II chain. The most common tumor-associated antigens found in some human cancers have the lacto series Type II chain structure, which usually is sialylated and/or fucosylated. Type I chain antigens are abundant in normal cells and tissues, and occasionally are associated with cancer (Stroud et al., *JBC*, 266: 8439-8446, 1991). For example, 2→3 sialylated Le$^a$ antigen (the CA 19-9 antigen defined by the N19-9 antibody) is a cancer-associated Type I chain antigen. However, cancer diagnostic methods based on the detection of those Type I chain antigens have been hampered by high false positive and/or high false negative incidences, see, for example, U.S. Pat. Nos. 6,083,929 and 6,294,523.

Two mouse monoclonal antibodies, NCC-ST421 and IMH2, were raised against extended Type I chain antigens. NCC-ST421 is specific for Le$^a$-Le$^a$. The NCC-ST421 antibody strongly induced antibody dependant cell cytotoxicity (ADCC) using human peripheral blood leukocytes as effectors against a variety of human tumor cells, and induced complement-dependent cytotoxicity (CDC) with a human complement source (Watanabe et al., *Cancer Res.*, 51:2199-2204, 1991). The Le$^a$-Le$^a$ antigen was found to be highly expressed in the human colon carcinoma cell line, Colo205.

MAb IMH2 was also established against extended Type I chains. MAb IMH2 bound to Le$^b$-Le$^a$, Le$^y$-Le$^x$, Le$^b$ and Le$^y$ based on $^1$H-NMR, FAB-MS and enzymatic degradation studies (Stroud et al., *Eur. J. Biochem.*, 203:577-586, 1992). MAb IMH2 showed strong lymphocyte-activated killing or complement-dependent killing of Colo205 cells in vitro, and inhibited the growth of Colo205 cells in vivo.

MAb IMH2 reacted with carcinoma tissues derived from colon, pancreas, liver and endometrium. However, normal colon showed no reactivity with MAb IMH2. Normal liver and pancreas showed weak or highly restricted reactivity in normal hepatocytes and islets of Langerhans cells. Immunochemical staining intensity was much stronger in endometrial carcinomas than in normal endometrium (Ito et al., *Cancer Res.*, 52:3739-3745, 1992).

Both mAbs NCC-ST421 and IMH2 exhibit inhibition of tumor growth in nude mice after inoculation of human tumor cells expressing the extended Type I chain antigen, but no inhibition of growth occurred in tumor cells that did not express extended Type I chain antigen.

Because of the abundance of Type I chain structures on normal cells, the use of antibodies against Type I chain structures for diagnostic and/or therapeutic purposes heretofore was not possible.

Conventional cancer treatments, such as chemotherapy and radiotherapy, have shown some advantages in various cancer patients. Despite the benefits of antitumor activity in conventional therapies, however, treatment-induced toxicity to normal tissues can substantially reduce the quality of life in cancer patients. Dose intensification for better antitumor activity is also limited. Monoclonal antibodies enable the promise of targeted cytotoxicity, focusing on tumor tissues, but not normal tissues.

Monoclonal antibodies (mAbs) can be developed with high specificity for antigens expressed on tumor cells and can elicit desired antitumor activities. The promise of mAbs was furthered by the development of mice that produce fully human mAbs. One such tool is the KM mouse. See U.S. Pat. No. 7,041,870 and Tomizuka et al., Nat. Genet. 16:133-143, 1997. In the KM mouse, the mouse genes encoding immunoglobulins were inactivated and replaced with human antibody genes. Thus, the KM mouse expresses fully human antibodies.

Several fully human antibodies have been successfully developed using the KM mouse.

For example, Motoki et al. developed a human IgG (KMTR2) which directed antibody-dependent oligomerization of TRAIL-R2 and initiated efficient apoptotic signaling and tumor regression independent of host effector function (Motoki et al., *Clin. Cancer Res.*, 11(8):3126-3135, 2005; and see also U.S. Pat. No. 7,115,717 and Imakire et al., *Int. J. Cancer,* 108:564-570, 2004). HD8, a fully human monoclonal antibody specific for human leukocyte antigen DR (HLA-DR), exerted antibody-dependent cellular cytotoxicity (ADCC) as well as complement-dependent cytotoxicity (CDC) in vitro, and extended the life span of immunocompromised mice inoculated with non-Hodgkin lymphoma cell lines (Tawara et al., *Cancer Sci.*, 98(6):921-928, 2007).

Additionally, two human IgMs raised in KM mice and directed to carbohydrate antigens were reported. HMMC-1 specifically recognizes a novel O-glycan structure, reacts positively with Mullerian duct-related carcinomas, and exhibits complement-dependent cytotoxicity on a human uterine endometrial cancer cell line, SNG-S (Nozawa et al., *Clin. Cancer Res.*, 10:7071-7078, 2004). Another human monoclonal IgM, HMOCC-1, recognizing a glycoprotein located on the cell membrane, reacted with ovarian cancer (Suzuki et al., *Gynecol. Oncol.*, 95:290-298, 2004). Since these two antibodies are IgMs, their application in cancer therapy should be limited due to molecule size and restrictions in production.

SUMMARY OF THE INVENTION

This invention provides novel human antibodies, as well as fragments and derivatives thereof, that specifically bind to extended Type I chain antigens, in particular extended Type I chain glycosphingolipids.

This invention also includes the amino acid sequences of the variable heavy and light chains of the aforesaid antibodies and their corresponding nucleic acid sequences.

Another embodiment of this invention includes the complementarity determining region (CDR) sequences of the antibodies of interest to obtain binding molecules that comprise one or more CDR regions, or CDR-derived regions, that retain extended Type I chain antigen-binding capacity of the parent molecule from which the CDR regions were obtained.

Another embodiment of the present invention includes cell lines and vectors capable of expressing the antibody of this invention.

Another embodiment of this invention relates to the use of the aforesaid antibodies for the preparation of a medicament or composition for the treatment of diseases or disorders associated with the function, metabolism or expression of extended Type I chain antigens, in particular an extended Type I chain glycosphingolipids.

Another embodiment of this invention relates to the use of the aforesaid antibodies in the diagnosis of disorders associated with atypical or abnormal biology and/or expression of extended Type I chain antigens, in particular an extended Type I chain glycosphingolipids.

These and other goals were met in the development of human monoclonal antibodies against extended Type I chain carbohydrate antigens. For example, mAb GNX-8, which is a human $IgG_1$ derived from a KM mouse, exhibits both CDC and ADCC activities on several human colorectal cancer cell lines and inhibits Colo205 and DLD-1 tumor growth in vivo. Besides, mAb GNX-8 reacts with primary and metastatic colorectal cancers, breast cancers, pancreas cancers as well as lung cancers, but not with normal human tissues and blood cells.

A further mAb GNX-10, which has heavy chain and light chain variable regions structurally similar to those of mAb GNX-8, exhibits binding specificity characteristics closely similar to those of mAb GNX-8.

Based on the CDR regions of mAbs GNX-8 and GNX-10, in one aspect of this invention, there is provided a binding moiety which specifically binds to an epitope comprising an extended Type I chain comprising $Le^b$, wherein the binding moiety comprises:
(a) a heavy chain variable region ($V_H$) that includes:
(i) a $V_H$ CDR1 sequence: Gly-Asp-Ser-Val-Ser-Ser-$X_1$-$X_2$-Val-Ala (SEQ ID NO:42), wherein $X_1$ is selected from the group consisting of Asn and Lys, and $X_2$ is selected from the group consisting of Thr and Ser;
(ii) a $V_H$ CDR2 sequence: Thr-Tyr-Tyr-Arg-Ser-Lys-Trp-Tyr-Asn (SEQ ID NO:32); and
(iii) a $V_H$ CDR3 sequence: Ala-Arg-Asn-Phe-Asp-$X_3$ (SEQ ID NO:43), wherein $X_3$ is selected from the group consisting of Ser and Tyr; and
(b) a light chain variable region ($V_L$) that includes:
(i) a $V_L$ CDR1 sequence: Thr-Gly-Ala-Val-Thr-Thr-$X_4$-Asn-Tyr (SEQ ID NO:44), wherein $X_4$ is selected from the group consisting of Asp and Asn;
(ii) a $V_L$ CDR2 sequence: Ala-Thr-Ser (SEQ ID NO:36); and
(iii) a $V_L$ CDR3 sequence: Ala-Leu-Trp-Tyr-Asn-Thr-His-Phe-Val (SEQ ID NO:37).

BRIEF DESCRIPTION OF THE DRAWINGS

The above and other objects, features and advantages of this invention will become apparent with reference to the following detailed description and the preferred embodiments taken in conjunction with the accompanying drawings, in which.

DETAILED DESCRIPTION OF THE INVENTION

Figure 1:
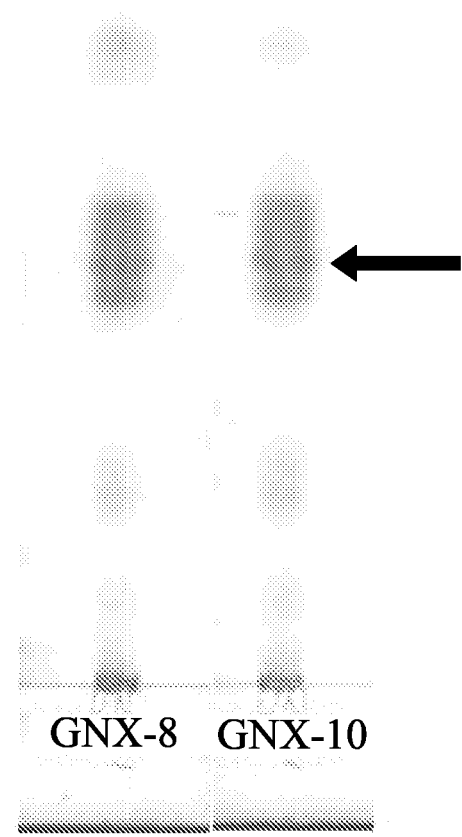
FIG. 1 shows the TLC immunostaining results of mAbs GNX-8 and GNX-10.

For the purpose of this specification, it will be clearly understood that the word "comprising" means "including but not limited to", and that the word "comprises" has a corresponding meaning.

This invention is not limited to the particular methodology, protocols, polypeptides, polynucleotides, cell lines, vectors, or reagents described herein because variations can occur or can be used without departing from the spirit and scope of the invention. Further, the terminology used herein is for the purpose of exemplifying particular embodiments only and is not intended to limit the scope of the present invention. Unless defined otherwise, all technical and scientific terms and any acronyms used herein have the same meanings as commonly understood by one of ordinary skill in the art in the field of this invention. Any method and material similar or equivalent to those described herein could be used in the practice of this invention and only exemplary methods, devices, and materials are described herein.

All patents and publications mentioned herein are incorporated herein in their entirety by reference for the purpose of describing and disclosing the proteins, enzymes, vectors, host cells and methodologies reported therein that might be used with and in this invention. However, nothing herein is to be construed as an admission that this invention is not entitled to antedate such disclosures by virtue of prior invention.

"An extended Type I chain antigen disease", in particular "an extended Type I chain glycosphingolipid disease" is a malady, disorder, disease, pathology, condition, abnormality and so on, which is characterized by, associated with or caused by abnormal metabolism, overexpression or increased levels of extended Type I chain antigen, in particular extended Type I chain glycosphingolipid, for example, at the cell surface.

The phrase "substantially identical" with respect to an antibody polypeptide sequence may be construed as an antibody chain exhibiting at least 70%, 80%, 90%, 95% or more sequence identity to a reference polypeptide sequence. The term with respect to a nucleic acid sequence may be construed as a sequence of nucleotides exhibiting at least about 85%, 90%, 95%, 97% or more sequence identity to a reference nucleic acid sequence.

As used herein, the terms "identity" and "homolog" each may mean the percentage of nucleotide bases or amino acid residues in the candidate sequence that is identical with the residues of a corresponding sequence to which the candidate is compared, after aligning the sequences and introducing gaps, if necessary, to achieve the maximum percent identity for the entire sequence, and not considering any conservative substitutions as part of the sequence identity. Neither N-terminal nor C-terminal extensions or insertions shall be construed as reducing identity or homology. Methods and computer programs for the alignment of sequences are available and are well known in the art. Sequence identity may be measured using sequence analysis software.

The phrases and terms "functional fragment, variant, derivative or analog" and the like, as well as forms thereof, of an antibody, nucleic acid or antigen is a compound or molecule having qualitative biological activity in common with a full length antibody or antigen of interest. For example, a functional fragment or analog of an antibody against an extended Type I chain antigen, in particular extended Type I chain glycosphingolipid, is one which can bind to an extended Type I chain antigen molecule, in particular an extended Type I chain glycosphingolipid molecule, or is an agonistic or antagonistic antibody which binds to an extended Type I chain antigen, in particular extended Type I chain glycosphingolipid. An example is a scFv molecule. As to an extended Type I chain glycosphingolipid, a variant or derivative thereof is a molecule that is not identical to a naturally occurring extended Type I chain glycosphingolipid and yet can be used for a purpose of the instant invention, such as, while not identical to a wild-type extended Type I chain glycosphingolipid nevertheless can be used, for example, as an immunogen to raise antibodies that selectively bind to wild-type extended Type I chain glycosphingolipid.

"Substitutional" variants are those that have at least one amino acid residue in a native sequence removed and replaced with a different amino acid inserted in place at the same position. The substitutions may be single, where only one amino acid in the molecule is substituted, or may be multiple, where two or more amino acids are substituted in the same molecule. The plural substitutions may be at consecutive sites. Also, one amino acid can be replaced with plural residues, in which case such a variant comprises both a substitution and an insertion.

"Insertional" variants are those with one or more amino acids inserted immediately adjacent to an amino acid at a particular position in a native sequence.

Immediately adjacent to an amino acid means connected to either the α-carboxyl or α-amino functional group of the amino acid.

"Deletional" variants are those with one or more amino acids in the native amino acid sequence removed. Ordinarily, deletional variants will have one or two amino acids deleted in a particular region of the molecule.

The terms "substitutional, insertional and deletional variants" as described above also apply analogously to nucleic acids.

The adaptive immune response has two major arms: the cellular immune response of T lymphocytes and the humoral immune response of antibody secreting B lymphocytes. B cell epitopes can be linear, contiguous amino acids, or can be conformational (Blythe et al., *Protein Science* (2005), 14:246-248). In contrast, T cell epitopes are short linear peptides that are cleaved from antigenic proteins that are presented in the context of major histocompatibility complex (MHC) proteins, or, in case of humans, human leukocyte antigen (HLA) class I or class II molecules. Epitope presentation depends on both MHC-peptide binding and T cell receptor (TCR) interactions. MHC proteins are highly polymorphic, and each binds to a limited set of peptides. Thus, the particular combination of MHC alleles present in a host limits the range of potential epitopes recognized during an infection.

Two fundamental types of T cells are distinguished by expression of CD8 and CD4 proteins, which dictate whether a T cell will recognize epitopes presented by HLA class I or class II molecules, respectively. CD4$^+$ T epitopes are processed after encapsulation by antigen presenting cells in membrane bound vesicles, where the antigen is degraded by proteases into peptide fragments that bind to MHC class II proteins. In contrast, CD8$^+$ T cells generally recognize viral or self antigens expressed from or within a cell, proteins that are cleaved into short peptides in the cytosol by the immunoproteasome. After cleavage, peptides are translocated by the transporter associated with antigen processing (TAP) into the endoplasmic reticulum for loading onto HLA I antigens. CD4$^+$ T (helper) cell epitopes are critical in driving T cell-dependent immune responses to protein antigens.

The term "antibody" is used in the broadest sense, and includes monoclonal antibodies (including full length monoclonal antibodies), polyclonal antibodies, multispecific antibodies (e.g., bispecific antibodies), antibody fragments or synthetic polypeptides carrying one or more CDR or CDR-derived sequences so long as the antibody fragments or synthetic polypeptides exhibit the desired biological activity. Antibodies (Abs) and immunoglobulins (Igs) are glycoproteins having the same structural characteristics. Generally, antibodies are considered Igs with a defined or recognized specificity. Thus, while antibodies exhibit binding specificity to a specific target, immunoglobulins include both antibodies and other antibody-like molecules which lack target specificity.

The antibodies of this invention can be of any class (e.g., IgG, IgE, IgM, IgD, IgA and so on), or subclass (e.g., IgG$_1$, IgG$_2$, IgG$_{2a}$, IgG$_3$, IgG$_4$, IgA$_1$, IgA$_2$ and so on) ("type" and "class," and "subtype" and "subclass," are used interchangeably herein). Native or wild-type (that is, obtained from a non-artificially manipulated member of a population) antibodies and immunoglobulins, and monomers of polymeric antibodies, such as IgA and IgM, are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at the other end.

By "non-artificially manipulated" is meant not treated by non-natural means, such as immunization or transformation, to contain or to express a foreign antigen-binding molecule. Wild-type can refer to the most prevalent allele or species found in a population or to the antibody obtained from a non-artificially manipulated animal, as well as to naturally occurring alleles or polymorphisms which arise naturally and can be sustained in a population, or a variant or derivative arising through natural means, such as a malignancy, as compared to that obtained by a form of manipulation, such as mutagenesis, use of recombinant methods and so on to change an amino acid of the antigen-binding molecule. The use of the term is readily inferred and understood by the artisan in the context of the sentence, paragraph, concept, thought, idea and so on in which the term is found, used and so on.

According to this invention, the term "antibody against extended Type I chain antigen" and the term "anti-extended Type I chain antigen antibody" are interchangeably used herein and refer to an antibody or derived polypeptide which binds specifically to human extended Type I chain antigen(s), including glycosphingolipids, glycoproteins and glycans.

The term "variable," in the context of a variable domain of antibodies, refers to certain portions of a pertinent molecule which differ extensively in sequence between and amongst antibodies and can be integral in the specific recognition and binding site of a particular antibody to a particular target. However, the variability is not evenly distributed through the variable domains of antibodies.

The variability can be concentrated in three segments called complementarity determining regions (CDRs, i.e., CDR1, CDR2 and CDR3), also known as hypervariable regions, existing in both the light chain and the heavy chain variable domains. The more highly conserved portions of variable domains are called the framework (FR) regions or sequences. The variable domains of native heavy and light chains each comprise four FR regions, largely adopting a β sheet configuration, connected by three CDRs, which form loops connecting, and in some cases forming part of, the β sheet structure. The CDRs in each chain are held together, often in proximity, by the FR regions and, with the CDRs from the other chain, contribute to the formation of the target (epitope or determinant) binding site of antibodies (see Kabat et al., Sequences of Proteins of Immunological Interest, National Institute of Health, Bethesda, Md., USA (1987)). One CDR, such as CDR3 of the heavy chain, can alone carry the ability to bind specifically to the cognate epitope.

As used herein, numbering of immunoglobulin amino acid residues is done according to the immunoglobulin amino acid residue numbering system of Kabat et al., supra, unless otherwise indicated.

The term "antibody fragment" refers to a portion of an intact or a full length chain of an antibody, generally the target binding site or variable region. Examples of antibody fragments include, but are not limited to, Fab, Fab', F(ab')$_2$ and Fv fragments. A "functional fragment" or "analog" of an anti-extended Type I chain glycosphingolipid antibody" is one which can bind a cognate antigen. As used herein, functional fragment generally is synonymous with "antibody fragment," and with respect to antibodies, can refer to fragments, such as Fv, Fab, F(ab')$_2$ and so on which can bind a cognate antigen.

An "Fv" fragment consists of a dimer of one heavy and one light chain variable domain in a non-covalent association ($V_H$-$V_L$ dimer). In that configuration, the three CDRs of each variable domain interact to define a target binding site on the surface of the $V_H$-$V_L$ dimer, as in an intact antibody. Collectively, the six CDRs confer target binding specificity on the intact antibody. However, even a single variable domain (or half of an Fv comprising only three CDRs specific for a target) can have the ability to recognize and to bind target.

"Single-chain Fv," "scFv" or "scAb" antibody fragments comprise the $V_H$ and $V_L$ domains of an antibody, wherein the domains are present in a single polypeptide chain. Generally, the scFv polypeptide further comprises, between the $V_H$ and $V_L$ domains, a polypeptide linker, often a flexible molecule, such as an oligopeptide, which may be obtained from a naturally occurring molecule, derived from a naturally occurring molecule, or is an artificial sequence, such as polyglycine, and so on, which enables the sFv to form the desired structure for target binding. Some molecules can include one or more constant domains or a portion thereof.

The term "diabodies" refers to antibody fragments with two antigen binding sites, which fragments can comprise a heavy chain variable domain ($V_H$) connected to a light chain variable domain ($V_L$) in the same polypeptide chain. By using a linker that is too short to allow pairing between the two variable domains on the same chain, the diabody domains are forced to pair with the binding domains of another chain to create an antigen binding site.

The Fab fragment contains the variable and constant domains of the light chain and the variable and first constant domain ($C_{H1}$) of the heavy chain. Fab' fragments differ from Fab fragments by the addition of a few residues at the carboxyl terminus of the $C_{H1}$ domain to include one or more cysteines from the antibody hinge region. Fab' fragments can be produced by cleavage of the disulfide bond at the hinge cysteines of the F(ab')$_2$ pepsin digestion product. Additional enzymatic and chemical treatments of antibodies can yield other functional fragments of interest.

The term "monoclonal antibody" (mAb or MAb) as used herein refers to an antibody obtained from a population of substantially homogeneous antibodies, i.e., the individual antibodies comprising the population are identical except for possible naturally occurring mutations that may be present in minor amounts.

Monoclonal antibodies herein specifically include "chimeric" antibodies in which a portion of the heavy and/or light chain is identical with or homologous to corresponding sequences in antibodies derived from a particular species or belonging to a particular antibody class or subclass (type or subtype), with the remainder of the chain(s) identical with or homologous to corresponding sequences in antibodies derived from another species or belonging to another antibody class or subclass, as well as fragments of such antibodies, so long as the chimeric antibodies exhibit the desired biological activity of binding to extended Type I chain glycosphingolipid or impacting extended Type I chain glycosphingolipid activity or metabolism (U.S. Pat. No. 4,816,567; and Morrison et al., Proc. Natl. Acad. Sci. USA, 81:6851-6855, 1984). Thus, CDR's from one class of antibody can be grafted into the FR of an antibody of different class or subclass.

Monoclonal antibodies are specific, being directed against a single target site, epitope or determinant. Furthermore, in contrast to conventional (polyclonal) antibody preparations which typically include different antibodies directed against different determinants (epitopes) of an antigen, each monoclonal antibody is directed against a single determinant on the target. In addition to their specificity, monoclonal antibodies are advantageous being synthesized by a host cell, uncontaminated by other immunoglobulins, and provide for cloning the relevant gene and mRNA encoding the antibody chains thereof. The modifier "monoclonal" indicates the character of the antibody as being obtained from a substantially homogeneous population of antibodies, and is not to be construed as requiring production of the antibody by any particular method. For example, the monoclonal antibodies for use with this invention may be isolated from phage antibody libraries using well known techniques or can be purified from a polyclonal preparation. The parent monoclonal antibodies to be used in accordance with this invention may be made by the hybridoma method described by Kohler et al. (1975), *Nature,* 256:495-497, or may be made by recombinant methods well known in the art.

"Humanized" forms of non-human (e.g., murine) antibodies are chimeric immunoglobulins, immunoglobulin chains or fragments thereof (such as Fv, Fab, Fab', F(ab')$_2$ or other target-binding subsequences of antibodies) which contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence.

The humanized antibody may also comprise at least a portion of an immunoglobulin constant region (Fc), typically that of the human immunoglobulin template chosen. In general, the goal is to have an antibody molecule of certain specificity that is minimally immunogenic in a human. Thus, it is possible that one or more amino acids in one or more CDR's also can be changed to one that is less immunogenic to a human host, without substantially minimizing the specific binding function of the one or more CDR's to extended Type I chain antigen, in particular extended Type I chain glycosphingolipid.

Alternatively, the FR can be non-human but those amino acids most immunogenic are replaced with ones less immunogenic. Nevertheless, CDR grafting, as discussed above, is not the only way to obtain a humanized antibody. For example, modifying just the CDR regions may not be sufficient to optimize an antibody as it is not uncommon for framework residues to have a role in determining the overall three-dimensional structure of the CDR loops and the overall affinity of the antibody for the ligand.

Hence, any means can be practiced to reduce antibody immunogenicity so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule surface and not buried within the molecule, and hence, not readily accessible to the host immune system. Such a method is taught herein with respect to substituting, for example, charged or certain other residues on the antibody molecule, the goal being to reduce or dampen the immunogenicity of the resultant molecule without compromising the specificity of the antibody for the cognate epitope or determinant. See, for example, Studnicka et al. (1994), *Prot. Eng.,* 7(6):805-814; Greg A. Lazar et al. (2007), *Mol. Immunol.,* 44:1986-1998; Sims et al. (1993), *J. Immunol.,* 151:2296-2308; Chothia et al. (1987), *J. Mol. Biol.,* 196:901-917; Carter et al. (1992), *Proc. Natl. Acad. Sci. USA,* 89:4285-4289; Presta et al. (1993), *J. Immunol.,* 151:2623-2632, WO 2006/042333 and U.S. Pat. No. 5,869,619.

Strategies and methods for resurfacing antibodies, and other methods for reducing immunogenicity of antibodies within a different host, are disclosed, for example, in U.S. Pat. No. 5,639,641. Briefly, in a preferred method, (1) position alignments of a pool of antibody heavy and light chain variable regions are generated to yield heavy and light chain variable region framework surface exposed positions, wherein the alignment positions for all variable regions are at least about 98% identical; (2) a set of heavy and light chain variable region framework surface exposed amino acid residues is defined for a non-human, such as, a rodent antibody (or fragment thereof); (3) a set of heavy and light chain variable region framework surface exposed amino acid residues that is most closely identical to the set of rodent surface exposed amino acid residues is identified; and (4) the set of heavy and light chain variable region framework surface exposed amino acid residues defined in step (2) is substituted with the set of heavy and light chain variable region framework surface exposed amino acid residues identified in step (3), except for those amino acid residues that are within about 5 Å of any atom of any residue of a CDR of the, for example, rodent antibody, to yield a humanized, such as, a rodent antibody retaining binding specificity.

Antibodies can be humanized by a variety of other techniques including CDR grafting (EP 0239400 A2; WO 91/09967; and U.S. Pat. Nos. 5,530,101 and 5,585,089), veneering or resurfacing (EP 0592106 A1; EP 0519596 A1; Padlan (1991), *Mol. Immunol.,* 28(4/5):489-498; Studnicka et al. (1994), *Prot. Eng.,* 7(6):805-814; and Roguska et al. (1994), *Proc. Natl. Acad. Sci. USA,* 91:969-973), and chain shuffling (U.S. Pat. No. 5,565,332). Human antibodies can be made by a variety of methods known in the art including, but not limited to, phage display methods, see U.S. Pat. Nos. 4,444,887, 4,716,111, 5,545,806 and 5,814,318; and WO 98/46645, WO 98/50433, WO 98/24893, WO 98/16654, WO 96/34096, WO 96/33735 and WO 91/10741, using transgenic animals, such as rodents (Amgen, Kirin and Merdarex mice), using chimeric cells and so on.

"Antibody homolog" or "homolog" refers to any molecule which specifically binds extended Type I chain antigen, in particular extended Type I glycosphingolipid, as taught herein. Thus, an antibody homolog includes native or recombinant antibody, whether modified or not, portions of antibodies that retain the biological properties of interest, such as binding to extended Type I chain antigen, in particular extended Type I glycosphingolipid, such as an Fab or Fv molecule, a single chain antibody, a polypeptide carrying one or more CDR regions and so on. The amino acid sequence of the homolog need not be identical to that of the naturally occurring antibody but can be altered or modified to carry substituted amino acids, inserted amino acids, deleted amino acids, amino acids other than the twenty normally found in proteins and so on to obtain a polypeptide with enhanced or other beneficial properties.

Antibodies with homologous sequences are those antibodies with amino acid sequences that have sequence homology with the amino acid sequence of an antibody against extended Type I chain antigen according to this invention. Preferably, homology is with the amino acid sequence of the variable regions of an antibody of this invention. "Sequence homology" as applied to an amino acid sequence herein is defined as a sequence with at least about 90%, 91%, 92%, 93%, 94% or more sequence homology, and more preferably at least about 95%, 96%, 97%, 98% or 99% sequence homology to another amino acid sequence, as determined, for example, by the FASTA search method in accordance with Pearson and Lipman, *Proc. Natl. Acad. Sci. USA,* 85:2444-2448 (1988).

A chimeric antibody, as taught hereinabove, is one with different portions of an antibody derived from different sources, such as different antibodies, different classes of antibody, different animal species, for example, an antibody having a variable region derived from a murine monoclonal antibody paired with a human immunoglobulin constant region and so on. Thus, a humanized antibody is a species of chimeric antibody. Methods for producing chimeric antibodies are known in the art, see, e.g., Morrison (1985), *Science,* 229:1202-1207; Oi et al. (1986), *BioTechniques,* 4:214-221; Gillies et al. (1989), *J. Immunol. Methods,* 125:191-202; and U.S. Pat. Nos. 5,807,715, 4,816,567, and 4,816,397.

Artificial antibodies include scFv fragments, chimeric antibodies, diabodies, triabodies, tetrabodies and mru (see reviews by Winter and Milstein (1991), *Nature,* 349:293-299; and Hudson (1999), *Curr Opin. Immunol.,* 11:548-557), each with antigen-binding or epitope-binding ability. In the single chain Fv fragment (scFv), the $V_H$ and $V_L$ domains of an antibody are linked by a flexible peptide. Typically, the linker is a peptide of about 15 amino acids. If the linker is much smaller, for example, 5 amino acids, diabodies are formed, which are bivalent scFv dimers. If the linker is reduced to less than three amino acid residues, trimeric and tetrameric structures are formed that are called triabodies and tetrabodies, respectively. The smallest binding unit of an antibody is a CDR, for example, CDR3 of the heavy chain which has sufficient specific recognition and binding capacity. Such a fragment is called a molecular recognition unit or mru. Several such mrus can be linked together with short linker peptides, therefore forming an artificial binding protein with higher avidity than a single mru.

Also included within the scope of this invention are functional equivalents of an antibody of interest. The term "functional equivalents" includes antibodies with homologous sequences, antibody homologs, chimeric antibodies, antibody variants, antibody derivatives, artificial antibodies and modified antibodies, for example, wherein each functional equivalent is defined by the ability to bind to extended Type I chain antigen, in particular extended Type I chain glycosphingolipid. The skilled artisan will understand that there is an overlap in the group of molecules termed "antibody fragments" and the group termed "functional equivalents." Methods of producing functional equivalents which retain binding ability to extended Type I chain antigen, in particular extended Type I chain glycosphingolipid, are known to a person skilled in the art and are disclosed, for example, in WO 93/21319, EP 0239400 A2, WO 89/09622, EP 0338745 A1 and EP 0332424 A2.

The functional equivalents of this application also include modified antibodies, e.g., antibodies modified by the covalent attachment of any type of molecule to the antibody. For example, modified antibodies include antibodies that have been modified, e.g., by glycosylation, acetylation, pegylation, deamidation, phosphorylation, amidation, derivatization by known protecting/blocking groups, proteolytic cleavage, linkage to a cellular ligand, linkage to a toxin or cytotoxic moiety or other protein, etc. The covalent attachment need not yield an antibody that is immune from generating an anti-idiotypic response. The modifications may be achieved by known techniques, including, but not limited to, specific chemical cleavage, acetylation, formylation, metabolic synthesis, chemical conjugation, etc. Additionally, the modified antibodies may contain one or more non classical amino acids.

Many techniques are available to one of ordinary skill in the art which permit the optimization of binding affinity. Typically, the techniques involve substitution of various amino acid residues at the site of interest, followed by a screening analysis of binding affinity of the mutant polypeptide for the cognate antigen or epitope.

Once the antibody is identified and isolated, it is often useful to generate a variant antibody or mutant, or mutein, wherein one or more amino acid residues are altered, for example, in one or more of the hypervariable regions of the antibody. Alternatively, or in addition, one or more alterations (e.g., substitutions) of framework residues may be introduced in the antibody where these result in an improvement in the binding affinity of the antibody mutant for extended Type I chain antigen, in particular extended Type I chain glycosphingolipid.

Examples of framework region residues that can be modified include those which non-covalently bind antigen directly (Amit et al. (1986), *Science,* 233:747-753); interact with/ affect the conformation of a CDR (Chothia et al. (1987), *J. Mol. Biol.,* 196:901-917); and/or participate in the VL-VH interface (EP 239 400 A2). In certain embodiments, modification of one or more of such framework region residues results in an enhancement of the binding affinity of the antibody for the cognate antigen. For example, from about one to about five framework residues may be altered in the particular embodiment of this invention. Sometimes, that may be sufficient to yield an antibody mutant suitable for use in preclinical trials, even where none of the hypervariable region residues have been altered. Normally, however, the antibody mutant can comprise one or more hypervariable region alteration(s). The constant regions also can be altered to obtain desirable or more desirable effector properties.

The hypervariable region residues which are altered may be changed randomly, especially where the starting binding affinity of the parent antibody is such that randomly-produced antibody mutants can be readily screened for altered binding in an assay as taught herein.

One procedure for obtaining antibody mutants, such as CDR mutants, is "alanine scanning mutagenesis" (Cunningham and Wells (1989), *Science,* 244:1081-1085; and Cunningham and Wells (1991), *Proc. Nat. Acad. Sci. USA,* 84:6434-6437). One or more of the hypervariable region residue(s) is/are replaced by alanine or polyalanine residue(s). That/those hypervariable region residue(s) demonstrating functional sensitivity to the substitutions then is/are refined by introducing further or other mutations at or for the sites of substitution. Thus, while the site for introducing an amino acid sequence variation is predetermined, the nature of the mutation per se need not be predetermined. Similar substitutions can be attempted with other amino acids, depending on the desired property of the scanned residues.

A more systematic method for identifying amino acid residues to modify comprises identifying hypervariable region residues involved in binding extended Type I chain antigen, in particular extended Type I chain glycosphingolipid, and those hypervariable region residues with little or no involvement in binding extended Type I chain antigen, in particular extended Type I chain glycosphingolipid. An alanine scan of the non-binding hypervariable region residues is performed, with each Ala mutant tested for enhancing binding to extended Type I chain antigen, in particular extended Type I chain glycosphingolipid. In another embodiment, that/those residue(s) significantly involved in binding extended Type I chain antigen, in particular extended Type I chain glycosphingolipid, is/are selected to be modified. Modification can involve deletion of a residue or insertion of one or more residues adjacent to a residue of interest. However, normally the modification involves substitution of the residue by another amino acid. A conservative substitution can be a first substitution. If such a substitution results in a change in biological activity (e.g., binding affinity), then another conservative substitution can be made to determine if more substantial changes are obtained.

Even more substantial modification in an antibody range and presentation of biological properties can be obtained by selecting an amino acid that differs more substantially in properties from that normally resident at a site. Thus, such a substitution can be made while maintaining (a) the structure of the polypeptide backbone in the area of the substitution, for example, as a sheet or helical conformation; (b) the charge or hydrophobicity of the molecule at the target site, or (c) the bulk of the side chain.

For example, the naturally occurring amino acids can be divided into groups based on common side chain properties:
(1) hydrophobic: methionine (M or Met), alanine (A or Ala), valine (V or Val), leucine (L or Leu) and isoleucine (I or Ile);
(2) neutral, hydrophilic: cysteine (C or Cys), serine (S or Ser), threonine (T or Thr), asparagine (N or Asn) and glutamine (Q or Gln);
(3) acidic: aspartic acid (D or Asp) and glutamic acid (E or Glu);
(4) basic: histidine (H or H is), lysine (K or Lys) and arginine (R or Arg);
(5) residues that influence chain orientation: glycine (G or Gly) and proline (P or Pro), and
(6) aromatic: tryptophan (W or Trp), tyrosine (Y or Tyr) and phenylalanine (F or Phe).

Non-conservative substitutions can entail exchanging an amino acid with an amino acid from another group. Conservative substitutions can entail exchange of one amino acid for another within a group.

Preferred amino acid substitutions can include those which, for example: (1) reduce susceptibility to proteolysis, (2) reduce susceptibility to oxidation, (3) alter binding affinity, and (4) confer or modify other physicochemical or functional properties of such analogs.

Analogs can include various muteins of a sequence other than the naturally occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence) unless of a change in the bulk or conformation of the R group or side chain (see Thomas E. Creighton, in "Proteins: Structures and Molecular Principles," published by W. H. Freeman and Company, New York (1984); Introduction to Protein Structure, Branden and Tooze, eds., Garland Publishing, Inc., New York, N.Y. (1991); and Thornton et al. (1991), *Nature*, 354:105).

Ordinarily, the antibody mutant with improved biological properties will have an amino acid sequence having at least 75% amino acid sequence identity or similarity with the amino acid sequence of either the heavy or light chain variable domain of the parent antibody against human extended Type I chain antigen, more preferably at least 80%, at least 85%, at least 90% and often at least 95% identity. Identity or similarity with respect to parent antibody sequence is defined herein as the percentage of amino acid residues in the candidate sequence that are identical (i.e., same residue) or similar (i.e., amino acid residue from the same group based on common side-chain properties, supra) with the parent antibody residues, after aligning the sequences and introducing gaps, if necessary, to achieve the maximum percent sequence identity.

Alternatively, antibody mutants can be generated by systematic mutation of the FR and CDR regions of the heavy and light chains, or the Fc region of extended Type I chain antigen, in particular extended Type I chain glycosphingolipid.

Another procedure for generating antibody mutants involves the use of affinity maturation using phage display (Hawkins et al. (1992), *J. Mol. Biol.*, 254:889-896; and Lowman et al. (1991), *Biochemistry*, 30(45):10832-10838). Bacteriophage coat-protein fusions (Smith (1985), *Science*, 228: 1315-1317; Scott and Smith (1990), *Science*, 249:386-390; Cwirla et al. (1990), *Proc Natl Acad Sci USA*, 87:6378-6382; Devlin et al. (1990), *Science*, 249:404-406; Wells and Lowman (1992), *Curr. Opin. Struct. Biol.*, 2:597-604; and U.S. Pat. No. 5,223,409) are known to be useful for linking the phenotype of displayed proteins or peptides to the genotype of bacteriophage particles which encode them. The Fab domains of antibodies have also been displayed on phage (McCafferty et al. (1990), *Nature*, 348: 552-554; Barbas et al. (1991), *Proc. Natl. Acad. Sci. USA*, 88:7978-7982; and Garrard et al. (1991), *Biotechnol.*, 9:1373-1377).

Monovalent phage display consists of displaying a set of protein variants as fusions of a bacteriophage coat protein on phage particles (Bass et al. (1990), *Proteins*, 8:309-314) Affinity maturation, or improvement of equilibrium binding affinities of various proteins, has previously been achieved through successive application of mutagenesis, monovalent phage display and functional analysis (Lowman and Wells (1993), *J. Mol. Biol.*, 234:564-578; and U.S. Pat. No. 5,534, 617), as well as using that approach with Fab domains of antibodies (Barbas et al. (1994), *Proc. Natl. Acad. Sci. USA*, 91:3809-3813; and Yang et al. (1995), *J. Mol. Biol.*, 254:392-403).

Libraries of many (for example, $10^6$ or more) protein variants, differing at defined positions in the sequence, can be constructed on bacteriophage particles, each of which contains DNA encoding the particular protein variant. Thus, several hypervariable region sites (e.g., 6-7 sites) are mutated to generate all possible amino acid substitutions at each site. After cycles of affinity purification, using an immobilized antigen, individual bacteriophage clones are isolated, and the amino acid sequence of the displayed protein is deduced from the DNA.

Following production of the antibody mutant, the biological activity of that molecule relative to the parent antibody can be determined as taught herein. As noted above, this may involve determining the binding affinity and/or other biological activities or physical properties of the antibody. In a preferred embodiment of this invention, a panel of antibody mutants is prepared and is screened for binding affinity for the antigen. One or more of the antibody mutants selected from the screen are optionally subjected to one or more further biological activity assays to confirm that the antibody mutant(s) has/have new or improved properties. In preferred embodiments, the antibody mutant retains the ability to bind extended Type I chain antigen, in particular extended Type I chain glycosphingolipid, with a binding affinity similar to or better/higher than that of the parent antibody.

Alternatively, multivalent phage (McCafferty et al. (1990), *Nature*, 348:552-554; and Clackson et al. (1991), *Nature*, 352:624-628) also can be used to express random point mutations (for example, generated by use of an error-prone DNA polymerase) to generate a library of phage antibody fragments which then could be screened for affinity to extended Type I chain antigen, in particular extended Type I chain glycosphingolipid (Hawkins et al. (1992), *J, Mol, Biol.*, 254: 889-896).

Preferably, during the affinity maturation process, the replicable expression vector is under tight control of a transcription regulatory element, and the culturing conditions are adjusted so that the amount or number of particles displaying more than one copy of the fusion protein is less than about 1%. Also preferably, the amount of particles displaying more than one copy of the fusion protein is less than about 10% of the amount of particles displaying a single copy of the fusion protein. Preferably the amount is less than about 20%.

Another equivalent phrase used herein is an antigen-binding portion, which relates to that portion of an antibody of interest which binds an epitope of extended Type I chain antigen. All of the phrases and terms used herein to describe various changes that can be made to an original antibody are considered to fall within the scope of the phrase "antigen-binding portion." Hence, for example, an antibody fragment, such as a Fab molecule, a Fv, a scAb, an mru, any such functional fragments, an antibody variant, such as an allele or a molecule containing a change in the primary amino acid sequence thereof, a derivative, such as a chimeric or humanized antibody, an analog and so on, including functional equivalents, which include genetically modified forms of an antibody of interest, antibody homologs, as described herein, and so on are included in the phrase antigen-binding portion.

The antibody mutant(s) so selected may be subjected to further modifications, often depending on the intended use of the antibody. Such modifications may involve further alteration of the amino acid sequence, fusion to heterologous polypeptide(s) and/or covalent modifications. For example, a cysteine residue not involved in maintaining the proper conformation of the antibody mutant may be substituted, generally with serine, to improve the oxidative stability of the molecule and to prevent aberrant cross-linking. Conversely, a cysteine may be added to the antibody to improve stability (particularly where the antibody is an antibody fragment, such as a Fv fragment).

Another type of antibody mutant has an altered glycosylation pattern. That may be achieved by adding or deleting one or more carbohydrate moieties found in the antibody and/or by adding or deleting one or more glycosylation sites that are not present in the antibody. Glycosylation of antibodies is typically either N linked to Asn or O-linked to Ser or Thr. The tripeptide sequences, asparagine-X-serine and asparagine-X-threonine, where X is any amino acid except proline, are common recognition sequences for enzymatic attachment of a carbohydrate moiety to the asparagine side chain. N-acetylgalactosamine, galactose, fucose or xylose, for example, is bonded to a hydroxyamino acid, most commonly serine or threonine, although 5-hydroxyproline or 5-hydroxylysine also may be used. Addition or substitution of one or more serine or threonine residues to the sequence of the original antibody can enhance the likelihood of O-linked glycosylation.

It may be desirable to modify the antibody of this invention with respect to effector function, so as to enhance the effectiveness of the antibody. For example, cysteine residue(s) may be introduced in the Fc region, thereby allowing interchain disulfide bond formation in that region. The homodimeric antibody thus generated may have improved internalization capability and/or increased cell killing mediated by complement and antibody-dependent cellular cytotoxicity (ADCC), see Caron et al. (1992), *J. Exp. Med.*, 176: 1191-1195 and Shopes (1992), *J. Immunol.*, 148:2918 2922. Such an antibody derivative or analog also may be more resistant to degradation in vivo.

Alternatively, an antibody can be engineered which has dual Fc regions and may thereby have enhanced complement lysis and ADCC capabilities, see Stevenson et al. (1989), *Anti-Cancer Drug Design*, 3: 219-230.

Covalent modifications of the antibody are included within the scope of this invention. Such may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or with the N terminal or C-terminal residue.

Cysteinyl residues can be reacted with α-haloacetates (and corresponding amines), such as chloroacetic acid or chloroacetamide, to yield carboxylmethyl or carboxyamidomethyl derivatives. Cysteinyl residues also can be derivatized by reaction with bromotrifluoroacetone, α-bromo-β-(5-imidazoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol or chloro-7-nitrobenzo-2-oxa-1,3-diazole, for example.

Histidyl residues can be derivatized by reaction with diethylpyrocarbonate at pH 5.5-7.0. p-Bromophenacyl bromide also can be used, and the reaction is preferably performed in 0.1 M sodium cacodylate at pH 6.0.

Lysinyl and α-terminal residues can be reacted with succinic or other carboxylic acid anhydrides to reverse the charge of the residues. Other suitable reagents for derivatizing α-amino-containing residues include imidoesters, such as, methyl picolinimidate, pyridoxal phosphate, pyridoxal, chloroborohydride, trinitrobenzenesulfonic acid, O-methylisourea and 2,4-pentanedione, and the amino acid can be transaminase-catalyzed with glyoxylate.

Arginyl residues can be modified by reaction with one or several conventional reagents, such as phenylglyoxal, 2,3-butanedione, 1,2-cyclohexanedione and ninhydrin. Derivatization of arginine residues often requires alkaline reaction conditions. Furthermore, the reagents may react with lysine as well as the arginine ε-amino group.

The specific modification of tyrosyl residues can be made with aromatic diazonium compounds or tetranitromethane. For example, N-acetylimidazole and tetranitromethane are used to form O-acetyl tyrosyl species and 3-nitro derivatives, respectively. Tyrosyl residues can be iodinated using $^{125}$I or $^{131}$I to prepare labeled proteins for use in a radioimmunoassay.

Carboxyl side groups (aspartyl or glutamyl) can be modified by reaction with carbodiimides (R—N═C═C—R'), where R and R' can be different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonium ions.

Glutaminyl and asparaginyl residues are frequently deamidated to the corresponding glutamyl and aspartyl residues, respectively, under neutral or basic conditions. The deamidated form of those residues falls within the scope of this invention.

Other modifications include hydroxylation of proline and lysine, phosphorylation of hydroxyl groups of serinyl or threonyl residues, methylation of the α-amino groups of lysine, arginine, and histidine side chains (Thomas E. Creighton, in "Proteins: Structures and Molecular Principles," published by W. H. Freeman and Company, San Francisco, pp. 79-86, 1983), acetylation of the N-terminal amine and amidation of any C-terminal carboxyl group.

Another type of covalent modification involves chemically or enzymatically coupling carbohydrates and glycosides to the antibody. Those procedures do not require production of the antibody in a host cell that has glycosylation capabilities for N-linked or O-linked glycosylation. Depending on the coupling mode used, the sugar(s) may be attached to: (a) arginine and histidine; (b) free carboxyl groups; (c) free sulfhydryl groups, such as those of cysteine; (d) free hydroxyl groups, such as those of serine, threonine or hydroxyproline; (e) aromatic residues such as those of phenylalanine, tyrosine or tryptophan; or (f) the amide group of glutamine. Such methods are described in WO 87/05330 and in Aplin and Wriston (1981), *CRC Crit. Rev. Biochem.*, 10(4):259-306.

Removal of any carbohydrate moieties present on the antibody may be accomplished chemically or enzymatically. Chemical deglycosylation, for example, can require exposure of the antibody to the compound, trifluoromethanesulfonic acid, or an equivalent compound, resulting in cleavage of most or all sugars except the linking sugar (N-acetylglucosamine or N-acetylgalactosamine), while leaving the antibody intact. Chemical deglycosylation is described, for example, in Sojar and Bahl (1987), *Arch. Biochem. Biophys.*, 259:52-57 and in Edge et al. (1981), *Anal. Biochem.*, 118:131-137. Enzymatic cleavage of carbohydrate moieties on antibodies can be achieved by any of a variety of endoglycosidases and exoglycosidases as described, for example, in Thotakura et al. (1987), *Meth. Enzymol.*, 138:350-359.

Another type of covalent modification of the antibody comprises linking the antibody to one of a variety of nonproteinaceous polymers, e.g., polyethylene glycol, polypropylene glycol or polyoxyalkylenes, in the manner set forth in any of U.S. Pat. Nos. 4,640,835, 4,496,689, 4,301,144, 4,670,417, 4,791,192 and 4,179,337.

Functional equivalents may be produced by interchanging different CDR's of different antibody chains within a framework or a composite FR derived from plural antibodies. Thus, for example, different classes of antibody are possible for a given set of CDRs by substitution of different heavy chains, for example, $IgG_1$-$IgG_4$, IgM, $IgA_1$-$IgA_2$ or IgD, to yield different antibody types and isotypes against extended Type I chain antigen, in particular extended Type I chain glycosphingolipid. Similarly, artificial antibodies within the scope of this invention may be produced by embedding a given set of CDR's within an entirely synthetic framework.

The antibody fragments and functional equivalents of this invention encompass those molecules with a detectable degree of specific binding to extended Type I chain antigen, in particular extended Type I chain glycosphingolipid. A detectable degree of binding includes all values in the range of at least 10-100%, preferably at least 50%, 60% or 70%, more preferably at least 75%, 80%, 85%, 90%, 95% or 99% of the binding ability of an antibody of interest. Also included are equivalents with an affinity greater than 100% that of an antibody of interest.

The CDR's generally are of importance for epitope recognition and antibody binding. However, changes may be made to residues that comprise the CDR's without interfering with the ability of the antibody to recognize and to bind the cognate epitope. For example, changes that do not impact epitope recognition, yet increase the binding affinity of the antibody for the epitope, may be made. Several studies have surveyed the effects of introducing one or more amino acid changes at various positions in the sequence of an antibody, based on the knowledge of the primary antibody sequence, on the properties thereof, such as, binding and level of expression (Yang et al. (1995), *J. Mol. Biol.*, 254:392-403; Rader et al. (1998), *Proc. Natl. Acad. Sci. USA*, 95:8910-8915; and Vaughan et al. (1998), *Nature Biotechnology*, 16:535-539).

Thus, equivalents of an antibody of interest can be generated by changing the sequences of the heavy and light chain genes in the CDR1, CDR2 and/or CDR3, or in the framework regions, using methods such as oligonucleotide-mediated site directed mutagenesis, cassette mutagenesis, error-prone PCR, DNA shuffling, amino acid modification or mutator-strains of *E. coli* (Vaughan et al. (1998), *Nature Biotechnology*, 16:535-539; and Adey et al. (1996), Chap. 16, pp. 277-291, in Phage Display of Peptides and Proteins: A Laboratory Manual, Kay et al. eds., Academic Press, Inc., San Diego, Calif.), for example. The methods of changing the nucleic acid sequence of the primary antibody can result in antibodies with improved affinity (Gram et al. (1992), *Proc. Natl. Acad. Sci. USA*, 89:3576-3580; Boder et al. (2000), *Proc. Natl. Acad. Sci. USA*, 97:10701-10705; Davies and Riechmann (1996), *Immunotech.*, 2:169-179; Thompson et al. (1996), *J. Mol. Biol.*, 256:77-88; Short et al. (2002), *J. Biol. Chem.*, 277:16365-16370; and Furukawa et al. (2001), *J. Biol. Chem.*, 276:27622-27628).

Repeated cycles of "polypeptide selection" can be used to select for higher affinity binding by, for example, the selection of multiple amino acid changes which are selected by multiple selection of cycles. Following a first round of selection, involving a first region of selection of amino acids in the ligand or antibody polypeptide, additional rounds of selection in other regions or amino acids of the ligand are conducted. The cycles of selection are repeated until the desired affinity properties are achieved.

Improved antibodies also include those antibodies having improved characteristics that are prepared by the standard techniques of animal immunization, hybridoma formation and selection for antibodies with specific characteristics.

As used herein, the term "antagonist" refers to a molecule capable of inhibiting one or more biological activities associated with extended Type I chain antigen, in particular extended Type I chain glycosphingolipid. Antagonists may interfere with the maintenance and the growth of a cell expressing an extended Type I chain antigen, in particular extended Type I chain glycosphingolipid. All points of intervention by an antagonist are considered equivalent for purposes of this invention. Thus, included within the scope of this invention are antagonists, e.g., neutralizing antibodies that bind to extended Type I chain antigen, in particular extended Type I chain glycosphingolipid.

As used herein, the term "agonist" refers to an antibody, an antibody fragment, a conjugate and so on, which activates one or more biological activities of extended Type I chain antigen, in particular extended Type I chain glycosphingolipid, or a cell expressing same. Agonists can act as a mitogen of cells expressing extended Type I chain antigen, in particular extended Type I chain glycosphingolipid. All points of intervention by an agonist shall be considered equivalent for purposes of the instant invention. Thus, included within the scope of the invention are antibodies that bind to extended Type I chain antigen, in particular extended Type I chain glycosphingolipid, and enhance an activity, such as differentiation, for example.

As used herein, the terms "cell," "cell line" and "cell culture" include progeny thereof. It is also understood that all progeny may not be precisely identical, e.g., in DNA content, due to deliberate or inadvertent mutation. Variant progeny that have the same function or biological property of interest, as screened for in the original cell, are included in the scope of this invention. The term "host cells" used in this invention generally are prokaryotic or eukaryotic hosts, selected as a design choice.

In this invention, "transformation" of a cellular organism, cell or cell line with a nucleic acid means introducing a nucleic acid into a target cell so that the nucleic acid is replicable, either as an extrachromosomal element or by chromosomal integration; and, optionally, expressed. "Transfection" of a cell or organism with a nucleic acid refers to the taking up of the nucleic acid, e.g., an expression vector, by the cell or organism whether or not any coding sequences are in fact expressed. The terms "transfected host cell" and "transformed host cell" refer to a host cell in which an exogenous nucleic acid was introduced. Typical prokaryotic host cells include various strains of E. coli. Typical eukaryotic host cells are mammal cells, such as Chinese hamster ovary, or cells of human origin. The introduced nucleic acid sequence may be from the same species as the host cell or of a different species from the host cell, or may be a hybrid nucleic acid sequence, containing some foreign and some homologous nucleic acids. Transformation can also occur by transduction or infection with virus derived elements or carriers.

As used herein, the term "vector" means a nucleic acid construct, a carrier, containing a nucleic acid, a transgene, a foreign gene or a gene of interest, which can be operably linked to suitable control sequences to effect the expression thereof in a suitable host cell. Such control sequences include, for example, a promoter to effect transcription, an optional operator sequence to control such transcription, a sequence encoding suitable mRNA ribosome binding sites and sequences which control the termination of transcription and translation. The vector may be a plasmid, a phage particle or just a potential genomic insert. Once transformed into a suitable host cell, the vector may replicate and function independently of the host cell's genome, or may in some instances, integrate into a host cell's genome or other nucleic acid. In this invention, the terms "plasmid" and "vector" are used interchangeably, as a plasmid is a commonly used form of vector. However, this invention is intended to include such other forms of vectors which serve equivalent carrier function as and which are, or become, known in the art, such as viruses, phagemids, transposons, synthetic molecules that carry nucleic acids, liposomes and the like.

For purposes of treatment, the term "mammal" refers to any animal classified as a mammal, including human, domestic and farm animals, non-human primates, and zoo, sports or pet animals, such as dogs, horses, cats, cows, etc.

The antibodies of interest can be screened or can be used in an assay as described herein or as known in the art. Often, such assays require a reagent to be detectable, that is, for example, labeled. The word "label" when used herein refers to a detectable compound or composition which can be conjugated directly or indirectly to a molecule or protein, e.g., an antibody. The label may itself be detectable (e.g., radioisotope labels, particles or fluorescent labels) or may be an instrument to obtain a detectable signal, such as, in the case of an enzymatic label, may catalyze a chemical alteration of a substrate compound or composition which then is detectable.

As used herein, the term "solid phase" means a matrix to which an entity or molecule, such as, the antibody of this invention, can adhere or bind. Example of solid phases encompassed herein include those formed partially or entirely of glass (e.g., controlled pore glass), polysaccharides (e.g., agarose), plastics, polypropylenes, polyacrylamides, polystyrene, polyvinyl alcohol and silicones. In certain embodiments, depending on the context, the solid phase can comprise the well of an assay plate; in others, can be used in a purification column (e.g., an affinity chromatography column). Thus, the solid phase can be a paper, a bead, a plastic, a chip and so on, can be made from a variety of materials, such as nitrocellulose, agarose, polystyrene, polypropylene, silicon and so on, and can be in a variety of configurations.

Cells expressing extended Type I chain glycosphingolipid or glycans thereof, such as cell membrane preparations, as well as purified extended Type I chain glycosphingolipid, can be used as immunogens for generating antibodies of interest. The immunogen can be obtained or isolated from natural sources or can be made enzymatically or chemically. Whole cells, such as extended Type I chain glycosphingolipid expressing cells, cells derived from a natural source or from cancers, such as cancer cell lines, can be used. Cells that overexpress extended Type I chain glycosphingolipid may be used as the immunogen for making the antibodies of interest. Also, membrane preparations carrying extended Type I glycosphingolipid can be used, as known in the art. Such cells and portions thereof can be used as the antigen source in a diagnostic assay.

Nucleic acid molecules encoding amino acid sequence mutants can be prepared by a variety of methods known in the art. The methods include, but are not limited to, oligonucleotide-mediated (or site directed) mutagenesis, PCR mutagenesis and cassette mutagenesis of an earlier prepared mutant or a non-mutant version of the molecule of interest; (see, for example, Kunkel (1985), *Proc. Natl. Acad. Sci. USA*, 82:488-492).

Recombinant expression of an antibody of this invention, or fragment, derivative or analog thereof (e.g., a heavy or light chain of an antibody of this invention, a single chain antibody of this invention or an antibody mutein of this invention), includes construction of an expression vector containing a polynucleotide that encodes the antibody or a fragment of the antibody as described herein. Once a polynucleotide encoding an antibody molecule has been obtained, the vector for the production of the antibody may be produced by recombinant DNA technology as known in the art. An expression vector is constructed containing antibody coding sequences and appropriate transcriptional and translational control signals. The methods include, for example, in vitro recombinant DNA techniques, synthetic techniques and in vivo genetic recombination.

The expression vector is transferred to a host cell by conventional techniques and the transfected cells then are cultured by conventional techniques to produce an antibody or fragment thereof according to this invention. In one aspect of this invention, vectors encoding both the heavy and light chains may be co-expressed in the host cell for expression of the entire immunoglobulin molecule, as detailed herein.

A variety of host/expression vector systems may be utilized to express the antibody molecules of this invention. Such expression systems represent vehicles by which the coding sequences of interest may be produced and subsequently purified, but also represent cells which may, when transformed or transfected with the appropriate nucleotide coding sequences, express an antibody molecule of this invention in situ. Bacterial cells, such as *E. coli*, and eukaryotic cells are commonly used for the expression of a recombinant antibody molecule, especially for the expression of whole recombinant antibody molecule. For example, mammal cells such as CHO cells, in conjunction with a vector, such as one carrying the major intermediate early gene promoter element from human cytomegalovirus, are an effective expression system for antibodies (Foecking et al. (1986), *Gene*, 45:101-105; and Cockett et al. (1990), Bio/Technology, 8:622-667). Plants and plant cell culture, insect cells and so on also can be used to make the proteins of interest, as known in the art.

In addition, a host cell is chosen which modulates the expression of the inserted sequences, or modifies and processes the gene product in the specific fashion desired. Such modifications (e.g., glycosylation) and processing (e.g., cleavage) of protein products may be important for the function of the protein. Different host cells can have the particular characteristic and specific mechanisms for the desired post-translational processing and modification of proteins and gene products. Appropriate cell lines or host systems can be chosen to ensure the correct modification and processing of the expressed antibody of interest. Hence, eukaryotic host cells which possess the cellular machinery for proper processing of the primary transcript, glycosylation and phosphorylation of the gene product may be used. Such mammalian host cells include, but are not limited to, CHO, COS, 293, 3T3 or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with a foreign DNA controlled by appropriate expression control elements (e.g., promoter, enhancer sequences, transcription terminators, polyadenylation sites, etc.) and a selectable marker. Following the introduction of the foreign DNA, engineered cells may be allowed to grow for one to two days in an enriched media, and then are moved to a selective medium. The selectable marker in the foreign DNA confers resistance to the selection and allows cells to stably integrate the foreign DNA into a chromosome and be expanded into a cell line. Alternatively, an extrachromosomal element can be maintained in the cells under selection. Such engineered cell lines not only are useful for antibody production but are useful in screening and evaluation of compounds that interact directly or indirectly with the antibody molecule.

A number of selection systems may be used, including, but not limited to, using the Herpes simplex virus thymidine kinase (Wigler et al. (1977), *Cell,* 11:223-232), hypoxanthine-guanine phosphoribosyltransferase (Szybalska et al. (1962), *Proc. Natl. Acad. Sci. USA,* 48(12):2026-2034), glutamate synthase, in the presence of methionine sulfoximine (Birch et al. (2006), *Adv. Drug Del. Rev.,* 58:671-685; and see the website or literature of Lonza Group Ltd.) and adenine phosphoribosyltransferase (Lowy et al. (1980), *Cell,* 22:817-823) genes in tk, hgprt, gs or aprt cells, respectively. Also, antimetabolite resistance can be used as the basis of selection for the following genes: dhfr, which confers resistance to methotrexate (Wigler et al. (1980), *Proc. Natl. Acad. Sci. USA,* 77(6):3567-3570; O'Hare et al. (1981), *Proc. Natl. Acad. Sci. USA,* 78:1527-1531); gpt, which confers resistance to mycophenolic acid (Mulligan et al. (1981), *Proc. Natl. Acad. Sci. USA* 78:2072-2076); neo, which confers resistance to the aminoglycoside, G-418 (Wu et al. (1991), *Biotherapy,* 3:87-95); and hygro, which confers resistance to hygromycin (Santerre et al. (1984), Gene, 30:147-156). Methods known in the art of recombinant DNA technology may be routinely applied to select the desired recombinant clone, and such methods are described, for example, in Current Protocols in Molecular Biology, Ausubel et al. eds., John Wiley & Sons, Inc. (1998); M. Kriegler, Gene Transfer and Expression: A Laboratory Manual, Stockton Press, New York, N.Y. (1990); Current Protocols in Human Genetics, Dracopoli et al. eds., John Wiley & Sons, Inc. (1994); and Colberre-Garapin et al. (1981), *J. Mol. Biol.,* 150:1-14.

The expression levels of an antibody molecule can be increased by vector amplification (for example, see Bebbington et al., in DNA Cloning, Vol. 3., Glover, D., ed., IRL Press Ltd., Oxford, England, pp. 163-188 (1987)). When a marker in the vector system expressing antibody is amplifiable, an increase in the level of inhibitor present in the culture will increase the number of copies of the marker gene. Since the amplified region is associated with the antibody gene, production of the antibody will also increase (Crouse et al. (1983), *Mol. Cell. Biol.,* 3:257-266).

The host cell may be co-transfected with two or more expression vectors of this invention, for example, the first vector encoding a heavy chain-derived polypeptide and the second vector encoding a light chain-derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain can be placed before the heavy chain to avoid an excess of toxic free heavy chain (Proudfoot (1986), Nature, 322:562-565; and Kohler (1980), *Proc. Natl. Acad. Sci. USA,* 77:2197-2199). The coding sequences for the heavy and light chains may comprise cDNA or genomic DNA.

Once an antibody molecule of this invention has been produced by an animal, chemically synthesized or recombinantly expressed, it may be purified by any method known in the art for purification of an immunoglobulin molecule, for example, by chromatography (e.g., ion exchange, affinity, particularly by affinity for extended Type I chain antigen, in particular extended Type I chain glycosphingolipid, after Protein A and size-exclusion chromatography and so on), centrifugation, differential solubility or by any other standard technique(s) for the purification of proteins. In addition, the antibodies of this invention or fragments thereof, can be fused to heterologous polypeptide sequences described herein or otherwise known in the art, to facilitate purification.

The antibodies of this invention may be generated by any suitable method known in the art. Thus, a purified extended Type I chain structure can be used as antigen, optionally, with an adjuvant, such as complete or incomplete Freund's adjuvant. The antibodies of this invention may comprise polyclonal antibodies, although because of the modification of antibodies to optimize use in human, as well as to optimize the use of the antibody per se, monoclonal antibodies are preferred because of ease of production and manipulation of particular proteins. Methods of preparing polyclonal antibodies are known to the skilled artisan (Harlow et al., Antibodies: a Laboratory Manual, Cold Spring Harbor Laboratory Press, 2nd ed., Cold Spring Harbor, N.Y. (1988)).

For example, an immunogen, as exemplified herein, may be administered to various host animals including, but not limited to, rabbits, mice, camelids, rats, etc., to induce the production of serum containing polyclonal antibodies specific for extended Type I chain antigen, in particular extended Type I chain glycosphingolipid. The administration of the immunogen may entail one or more injections of an immunizing agent and, if desired, an adjuvant. Various adjuvants may be used to increase the immunological response, depending on the host species, and include, but are not limited to, Freund's (complete and incomplete), mineral oil, gels, alum (aluminum hydroxide), surface active substances, such as lysolecithin, pluronic polyols, polyanions, peptides, oil emulsions, keyhole limpet hemocyanins (KLH), dinitrophenol and potentially useful human adjuvants, such as BCG (bacille Calmette-Guerin) and *Corynebacterium parvum.* Additional examples of adjuvants which may be employed include the MPL-TDM adjuvant (monophosphoryl lipid A, synthetic trehalose dicorynomycolate). Immunization protocols are well known in the art and may be performed by any method that elicits an immune response in the animal host chosen. Thus, various administration routes can be used over various time periods as a design choice.

Typically, the immunogen (with or without adjuvant) is injected into the mammal by multiple subcutaneous or intraperitoneal injections, or intramuscularly or intravenously. In certain circumstances, whole cells expressing extended Type I chain antigen, in particular extended Type I chain glycosphingolipid, can be used. Depending on the nature of the immunogen (i.e., percent hydrophobicity, percent hydrophilicity, stability, net charge, isoelectric point, etc.), the extended Type I chain antigen or portion thereof may be modified or conjugated to be immunogenic or more immunogenic in the animal, such as a mammal, being immunized. For example, extended Type I chain antigen or a portion thereof can be conjugated to a carrier. The conjugation includes either chemical conjugation by derivatizing active chemical functional groups on either or both the immunogen and the immunogenic protein to be conjugated such that a covalent bond is formed, or other methods known to the skilled artisan. Examples of such carriers or immunogenic proteins include, but are not limited to, KLH, ovalbumin, serum albumin, bovine thyroglobulin, soybean trypsin inhibitor and promiscuous T helper peptides. Various adjuvants may be used to increase the immunological response as described above.

Once a suitable preparation is obtained, it is possible to isolate particular antibodies from the plural antibodies by known separation techniques, such as affinity chromatography, panning, absorption and so on. In that way, an individual antibody species can be obtained for further study, for example, sequencing to obtain the amino acid sequences of one or more CDRs.

The antibodies of this invention preferably comprise monoclonal antibodies. Monoclonal antibodies may be prepared using hybridoma technology, such as described in Kohler et al. (1975), Nature, 256:495-497; U.S. Pat. No. 4,376,110; Harlow et al., Antibodies: A Laboratory Manual, Cold Spring Harbor Laboratory Press, 2nd ed., Cold Spring Harbor, N.Y. (1988); and Hammerling et al., Monoclonal Antibodies and T-Cell Hybridomas, Elsevier/North Holland Biomedical Press, Inc., New York, N.Y. (1981), recombinant DNA methods, for example, making and using transfectomas, or other methods known to the artisan. Other examples of methods which may be employed for producing monoclonal antibodies include, but are not limited to, the human B-cell hybridoma technique (Kosbor et al. (1983), Immunology Today, 4:72-79; and Cole et al. (1983), Proc. Natl. Acad. Sci. USA, 80:2026-2030), and the EBV hybridoma technique (Cole et al., in Monoclonal Antibodies and Cancer Therapy, Vol. 27, pp. 77-96, R. A. Reisfeld et al. eds., Alan R. Liss, Inc., N.Y. (1985)). Such antibodies may be of any immunoglobulin class including IgG, IgM, IgE, IgA and IgD, and any subclass thereof. The hybridoma producing the mAb of this invention may be cultivated in vitro or in vivo.

In the hybridoma model, a host such as a mouse, a humanized mouse, a transgenic mouse with human immune system genes, horse, sheep, hamster, rabbit, rat, camel or any other appropriate host animal, is immunized to elicit lymphocytes that produce or are capable of producing antibodies that specifically bind to extended Type I chain antigen, in particular extended Type I chain glycosphingolipid.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, 2nd ed., Academic Press, Inc., pp. 59-103 (1986)).

Generally, in making antibody-producing hybridomas, either peripheral blood lymphocytes ("PBLs") are used if cells of human origin are desired, or spleen cells or lymph node cells are used if non-human mammalian sources are desired. Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells. For example, if the parental cells lack the enzyme, hypoxanthine guanine phosphoribosyl transferase (HGPRT or HPRT), the culture medium for the hybridomas typically will include hypoxanthine, aminopterin and thymidine ("HAT medium"), substances that prevent the growth of HGPRT-deficient cells.

Preferred immortalized cell lines are those that fuse efficiently, support stable high level production of antibody by the selected antibody-producing cells, and are sensitive to a medium, such as HAT medium. Amongst the myeloma cell lines are murine myeloma lines, such as those derived from the MOPC-21 and MPC-11 mouse tumors available from the Salk Institute Cell Distribution Center, San Diego, Calif., and SP2/0, FO or X63 Ag8-653 cells available from the American Type Culture Collection, Manassas, Va. The mouse myeloma cell line NSO also may be used (European Collection of Cell Cultures, Salisbury, Wilshire, UK).

Human myeloma and mouse-human heteromyeloma cell lines also have been described for the production of human monoclonal antibodies (Kozbor (1984), J. Immunol., 133: 3001-3005; and Brodeur et al., in Monoclonal Antibody Production Techniques and Applications, Schook ed., Marcel Dekker, Inc., New York, N.Y., pp. 51-63 (1987)).

Another alternative is to use electrical fusion rather than chemical fusion to form hybridomas. Instead of chemical fusion, a B cell can be immortalized using, for example, Epstein Barr Virus or another transforming gene, see, e.g., Zurawaki et al., in Monoclonal Antibodies, Kennett et al. ed., Plenum Press, N.Y., pp. 19-33. (1980). Transgenic mice expressing immunoglobulins and severe combined immunodeficient (SCID) mice transplanted with human B lymphocytes also can be used.

The culture medium in which hybridoma cells are grown is assayed for production of monoclonal antibodies directed against extended Type I chain antigen, in particular extended Type I chain glycosphingolipid. The binding specificity of monoclonal antibodies produced by hybridoma cells may be determined by immunoprecipitation or by an in vitro binding assay, such as radioimmunoassay (RIA), fluorocytometric analysis (FACS) or enzyme-linked immunosorbent assay (ELISA). Such techniques are known in the art and are within the skill of the artisan. Also, the Biacore system can be used, as known in the art. The binding affinity of the monoclonal antibody to extended Type I chain antigen, in particular extended Type I chain glycosphingolipid, can, for example, be determined by a Scatchard analysis (Munson et al. (1980), Anal. Biochem., 107:220-239).

After hybridoma cells that produce antibodies of the desired specificity, affinity and/or activity are identified, the clones may be subcloned by limiting dilution procedures and grown by standard methods (Goding, Monoclonal Antibodies: Principles and Practice, 2nd ed., Academic Press, Inc., pp. 59-103 (1986)). Suitable culture medium includes, for example, Dulbecco's Modified Eagle's Medium (DMEM) or RPMI-1640. In addition, the hybridoma cells may be grown in vivo as ascites tumors in an animal.

The monoclonal antibodies secreted by the subclones are suitably separated or isolated from the culture medium, ascites fluid or serum by conventional immunoglobulin purification procedures such as, for example, protein A Sepharose, protein G Sepharose, hydroxylapatite chromatography, gel exclusion chromatography, gel electrophoresis, dialysis or affinity chromatography.

A variety of methods exist in the art for the production of monoclonal antibodies and thus, this invention is not limited to their sole production in hybridomas. For example, the monoclonal antibodies may be made by recombinant DNA methods, such as those described in U.S. Pat. No. 4,816,567. Alternatively, human antibodies can be obtained from transgenic animals, such as the KM mouse, discussed above. In that context, the term "monoclonal antibody" refers to an antibody derived from a single eukaryotic, viral or prokaryotic clone.

Thus, using human cancer cells known to express an extended Type I chain structure, such as Colo205 cells, or an extended Type I chain-containing compound, such as $Le^b$-$Le^a$ glycosphingolipid, as antigen, inbred or transgenic mice are immunized and boosted as known in the art. Spleen cells were obtained and fused to myeloma cells, and hybridomas thus made were cultured. Cell supernatants were screened by ELISA using, for example, $Le^b$-$Le^a$ as the capture reagent. Positive clones were amplified. IMH2 is an example of a mouse $IgG_3$ monoclonal antibody that binds specifically to an extended Type I chain structure.

Using a transgenic mouse model, human antibodies can be produced by immunizing the transgenic mice with an extended Type I chain immunogen. Such antibodies can be generated on a fee basis, for example, by Medarex, NJ and Amgen, CA. Using the KM mouse, a monoclonal antibody GNX-8 ($IgG_1$) was selected for further characterization and use.

MAb GNX-8 is a cytotoxic antibody. In assays using Colo205 colon cancer cells as targets, GNX-8 lysed the cancer cell line cells, and at a dose of at least 50 µg/mL, the antibody lysed all cells in the culture. MAb GNX-8 does not bind to RBCs. The antibody binds to colorectal cancer cells, breast cancer cells and lung cancer cells. Unlike IMH2, mAb GNX-8 does not bind to $Le^y$-$Le^x$ or $Le^y$.

DNAs encoding the monoclonal antibodies of this invention are readily isolated and sequenced using conventional procedures (e.g., by using oligonucleotide probes that are capable of binding specifically to genes encoding the heavy and light chains of murine antibodies, or such chains from human, humanized or other sources)(see PCR Protocols. A Guide to Methods and Applications, Innis et al. eds., Academic Press, Inc., San Diego, Calif. (1990); and Sanger et al. (1977), *Proc. Natl. Acad. Sci.,* 74:5463-5467). The hybridoma cells can serve as the source of such DNA.

Once isolated, the DNA may be placed into expression vectors, which are then transfected into host cells such as *E. coli* cells, NSO cells, COS cells, Chinese hamster ovary (CHO) cells or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; and Morrison et al. (1984), *Proc. Natl. Acad. Sci. USA,* 81:6851-6855) or by covalently joining to the immunoglobulin coding sequence, all or part of the coding sequence of a non-immunoglobulin polypeptide. Such a non-immunoglobulin polypeptide can be substituted for the constant domains of an antibody of this invention, or can be substituted for the variable domains of one extended Type I chain antigen-binding site of an antibody of this invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Antibody fragments which recognize specific epitopes may be generated by known techniques. Traditionally, those fragments are derived via proteolytic digestion of intact antibodies (see, e.g., Morimoto et al. (1992), *J. Biochem. Biophys. Methods,* 24:107-117; and Brennan et al. (1985), *Science,* 229:81-83). For example, Fab and $F(ab')_2$ fragments of this invention may be produced by proteolytic cleavage of immunoglobulin molecules, using enzymes, such as papain (to produce Fab fragments) or pepsin (to produce $F(ab')_2$ fragments). F) fragments contain the variable region, the light chain constant region and the $C_{H1}$ domain of the heavy chain. However, those fragments can be produced directly by recombinant host cells. For example, the antibody fragments can be isolated from an antibody phage library. Alternatively, $F(ab')_2$-SH fragments can be directly recovered from *E. coli* cells and chemically coupled to form $F(ab')_2$ fragments (Carter et al. (1992), *Bio/Technology,* 10:163-167). According to another approach, $F(ab')_2$ fragments can be isolated directly from recombinant host cells cultured. Other techniques for the production of antibody fragments will be apparent to the skilled practitioner. In other embodiments, the antibody of choice is a single chain Fv fragment (scFv), see, for example, WO 93/16185.

For some uses, including in vivo use of antibodies in humans and in vitro detection assays, it may be preferable to use chimeric, humanized or human antibodies. Methods for producing chimeric antibodies are known in the art, see e.g., Morrison (1985), *Science,* 229:1202-1207; Oi et al. (1986), BioTechniques, 4:214-221; Gillies et al. (1989), *J. Immunol. Methods,* 125:191-202; and U.S. Pat. Nos. 5,807,715, 4,816, 567 and 4,816,397.

Humanized antibodies are derived from antibody molecules generated in a non-human species that bind extended Type I chain antigen, in particular extended Type I chain glycosphingolipid, wherein one or more CDR's therefrom are inserted into the FR regions from a human immunoglobulin molecule. Antibodies can be humanized using a variety of techniques known in the art including, for example, CDR grafting (EP 0239400 A2; WO 91/09967; and U.S. Pat. Nos. 5,225,539, 5,530,101 and 5,585,089), veneering or resurfacing (EP 0592106 A1; EP 0519596 A1; Padlan (1991), *Mol. Immunol.,* 28(4/5):489-498; Studnicka et al. (1994), *Prot. Eng.,* 7(6):805-814; and Roguska et al. (1994), *Proc. Natl. Acad. Sci. USA,* 91:969-973), and chain shuffling (U.S. Pat. No. 5,565,332).

A humanized antibody has one or more amino acid residues from a source that is non-human. The non-human amino acid residues are often referred to as "import" residues, which are typically taken from an "import" variable domain. Humanization can be essentially performed following the methods of Winter et al. (Jones et al. (1986), *Nature,* 321:522-525; Riechmann et al. (1988), *Nature,* 332:323-327; and Verhoeyen et al. (1988), *Science,* 239:1534-1536), by substituting non-human CDR's or portions of CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies. The heavy chain constant region and hinge region can be from any class or subclass to obtain a desired effect, such as a particular effector function.

Oftentimes, framework residues in the human framework regions can be substituted with the corresponding residue from the CDR donor antibody to alter, and possibly improve, antigen binding. The framework substitutions are identified by methods known in the art, e.g., by modeling of the interactions of the CDR and framework residues to identify framework residues important for antigen binding and sequence comparison to identify unusual framework residues at particular positions, see, e.g., U.S. Pat. No. 5,585,089; and Riechmann et al. (1988), Nature, 332:323-327.

It is further preferable that humanized antibodies retain high affinity for extended Type I chain antigen, in particular extended Type I chain glycosphingolipid, and retain or acquire other favorable biological properties. Thus, humanized antibodies can be prepared by a process by analyzing the parental sequences and various conceptual humanized antibody derivatives using three-dimensional models of the parental and humanized sequences. The hypothetical three-dimensional immunoglobulin models are commonly available and are familiar to those skilled in the art. Computer programs are available which illustrate and display probable three dimensional conformational structures of selected candidate immunoglobulin sequences. Inspection of the displays permits analysis of the likely role of certain residues in the functioning of the candidate immunoglobulin sequence, i.e., the analysis of residues that influence the ability of the candidate immunoglobulin to bind extended Type I chain antigen, in particular extended Type I chain glycosphingolipid. In that way, FR residues can be selected and combined from the recipient and import sequences so that the desired antibody characteristic, such as increased affinity for the target antigen, is maximized, although it is the CDR residues that directly and most substantially influence the extended Type I chain antigen binding. The CDR regions also can be modified to contain one or more amino acids that vary from that obtained from the parent antibody from which the CDR was obtained, to provide enhanced or different properties of interest, such as binding of greater affinity or greater avidity, for example.

Certain portions of the constant regions of the antibody of this invention can be manipulated and changed to provide antibody homologs, derivatives, fragments and the like with properties different from or better than that observed in the parent antibody. Thus, for example, many $IgG_4$ antibodies form intrachain disulfide bonds near the hinge region. The intrachain bond can destabilize the parent bivalent molecule to form monovalent molecules comprising the heavy chain associated with the light chain. Such molecules can reassociate, but, on a random basis.

Another set of amino acids suitable for modification include amino acids in the area of the hinge which impact antibody functions, such as binding of a molecule containing a heavy chain to the Fc receptor and internalization of bound antibody. Such amino acids include, in $IgG_1$ molecules, residues from about 233 to about 237 (Glu-Leu-Leu-Gly-Gly, SEQ ID NO:1); from about 252 to about 256 (Met-Ile-Ser-Arg-Thr, SEQ ID NO:2); and from about 318 (Glu) to about 331 (Pro), including, for example, $Lys_{320}$, $Lys_{322}$ and $Pr_{329}$.

Completely human antibodies are particularly desirable for therapeutic treatment of human patients. Human antibodies can be made by a variety of methods known in the art including phage display methods described above using antibody libraries derived from human immunoglobulin sequences, see, U.S. Pat. Nos. 4,444,887 and 4,716,111; and WO 98/46645, WO 98/50433, WO 98/24893, WO 98/16654, WO 96/34096, WO 96/33735 and WO 91/10741. The techniques of Cole et al. and Boerder et al. are also available for the preparation of human monoclonal antibodies (Cole et al., in Monoclonal Antibodies and Cancer Therapy, Vol. 27, pp. 77-96, R. A. Reisfeld et al. eds., Alan R. Liss, Inc., N.Y. (1985); and Boerner et al. (1991), J. Immunol., 147:86-95).

Human antibodies can also be produced using transgenic mice which are incapable of expressing functional endogenous immunoglobulins, but which also express certain human immunoglobulin genes. For example, the human heavy and light chain immunoglobulin gene complexes may be introduced randomly or by homologous recombination into mouse embryonic stem cells. Alternatively, nucleic acid sequences encoding the human variable region, constant region and diversity region may be introduced into mouse embryonic stem cells, in addition to the human heavy and light chain immunoglobulin genes. The mouse heavy and light chain immunoglobulin genes may be treated so as to be non-functional separately or simultaneously with the introduction of the human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies, see, e.g., Jakobovitis et al. (1993), Proc. Natl. Acad. Sci. USA, 90:2551-2555; Jakobovitis et al. (1993), Nature, 362:255-258; Bruggermann et al. (1993), Year in Immunol., 7:33-40; and Duchosal et al. (1992), Nature, 355:258-262).

The transgenic mice are immunized in the normal fashion with an extended Type I chain antigen, in particular extended Type I chain glycosphingolipid, e.g., all or a portion of an extended Type I chain antigen, or a membrane preparation containing same. Monoclonal antibodies directed against the extended Type I chain antigen, in particular extended Type I chain glycosphingolipid, can be obtained from the immunized, transgenic mice using conventional hybridoma technology. The human immunoglobulin transgenes harbored in the transgenic mice, rearrange during B cell differentiation, and subsequently undergo class switching and somatic mutation. Thus, using such a technique, it is possible to produce therapeutically useful IgG, IgA, IgM and IgE antibodies. For an overview, see Lonberg et al. (1995), Int. Rev. Immunol., 13:65-93. For a discussion of producing human antibodies and human monoclonal antibodies and protocols for producing such antibodies, see, e.g., WO 98/24893; WO 92/01047; WO 96/34096; and WO 96/33735; EP 0589877 A1; and U.S. Pat. Nos. 5,413,923, 5,625,126, 5,633,425, 5,569,825, 5,661,016, 5,545,806, 5,814,318, 5,885,793, 5,916,771 and 5,939,598. In addition, companies such as Amgen (Fremont, Calif., USA), Genpharm (San Jose, Calif., USA) and Medarex, Inc. (Princeton, N.J., USA) can be engaged to provide human antibodies directed against extended Type I chain antigen, in particular extended Type I chain glycosphingolipid, using technology similar to that described above.

Also, human mAbs could be made by immunizing mice transplanted with human peripheral blood leukocytes, splenocytes or bone marrow (e.g., trioma technique of XTL Biopharmaceuticals, Israel).

Completely human antibodies which recognize a selected epitope can be generated using a technique referred to as "guided selection." In that approach, a selected non-human monoclonal antibody, e.g., a mouse antibody, is used to guide the selection of a completely human antibody recognizing the same epitope (Jespers et al. (1988), *Bio/Technology*, 12:899-903).

When using recombinant techniques, the antibody variant can be produced intracellularly, in the periplasmic space, or directly secreted into the medium. If the antibody variant is produced intracellularly, as a first step, the particulate debris, either host cells or lysed fragments, may be removed, for example, by centrifugation or ultrafiltration. In Bio/Technology, 10:163 (1992), Carter et al. described a procedure for isolating antibodies which are secreted to the periplasmic space of transformed *E. coli* cells. Briefly, cell paste is exposed to sodium acetate (pH 3.5) and EDTA. Cell debris can be removed by centrifugation. Where the antibody variant is secreted into the medium, supernatant from such expression systems are generally first concentrated using a commercially available protein concentration filter, for example, an Amicon or Millipore Pellicon ultrafiltration unit. A protease inhibitor, such as, PMSF, may be included to inhibit proteolysis, and antibiotics may be included to prevent growth of adventitious contaminants.

The antibody composition prepared from the cells can be purified using, for example, hydroxylapatite chromatography, gel electrophoresis, dialysis and affinity chromatography. The suitability of protein A or protein G as an affinity ligand depends on the species and isotype of an immunoglobulin Fc domain that is present in the antibody variant. Protein A can be used to purify antibodies that are based on human $IgG_1$, $IgG_2$ or $IgG_4$ heavy chains (Lindmark et al. (1983), *J. Immunol. Meth.*, 62:1-13). Protein G can be used for mouse isotypes and for human $IgG_3$ (Guss et al. (1986), *EMBO J.*, 5:1567-1575). The matrix to which the affinity ligand is attached is most often agarose, but other matrices are available. Mechanically stable matrices, such as controlled pore glass or poly(styrenedivinyl)benzene, allow for faster flow rates and shorter processing times than can be achieved with agarose. Where the antibody variant comprises a $C_{H3}$ domain, the Bakerbond ABXTM resin (JT Baker; Phillipsburg, N.J., USA) is useful for purification. Other techniques for protein purification, such as fractionation on an ion-exchange column, ethanol precipitation, reverse phase HPLC, chromatography on silica, chromatography on heparin agarose, chromatography on an anion or cation exchange resin (such as a polyaspartic acid column), chromatofocusing, SDS-PAGE and ammonium sulfate precipitation, are also available, depending on the antibody or variant to be recovered.

Following any preliminary purification step(s), the mixture comprising the antibody or variant of interest and contaminants may be subjected to low pH hydrophobic interaction chromatography using an elution buffer at a pH of between about 2.5-4.5, preferably performed at low salt concentrations (e.g., from about 0 0.25 M salt).

Further, antibodies of this invention can, in turn, be utilized to generate anti-idiotype antibodies that "mimic" extended Type I chain antigen, in particular extended Type I chain glycosphingolipid, using techniques well known to those skilled in the art (see, e.g., Greenspan et al. (1989), *FASEB J.*, 7:437-444; and Nissinoff (1991), *J. Immunol.*, 147:2429-2438). For example, antibodies which bind to and competitively inhibit multimerization and/or binding of a ligand to extended Type I chain antigen can be used to generate anti-idiotypes that "mimic" extended Type I chain antigen. Such neutralizing anti-idiotypes or Fab fragments of such anti-idiotypes can be used in therapeutic or diagnostic regimens.

The antibodies of this invention may be bispecific antibodies. Bispecific antibodies can be monoclonal, preferably human or humanized, antibodies that have binding specificities for at least two different antigens. In this invention, one of the binding specificities is directed towards extended Type I chain antigen, in particular extended Type I chain glycosphingolipid, whereas the other specificity may be for any other antigen, such as a cell-surface protein, receptor, receptor subunit, ligand, tissue specific antigen, viral protein, virally-encoded envelope protein, pharmacologically active agent, such as a drug, bacterially-derived protein, bacterial surface protein, etc.

Methods for making bispecific antibodies are well known. Traditionally, the recombinant production of bispecific antibodies is based on the co-expression of two immunoglobulin heavy chain/light chain pairs, where the two heavy chains have different specificities (Milstein et al. (1983), *Nature*, 305:537-540). Because of the random assortment of immunoglobulin heavy and light chains, the hybridomas (quadromas) produce a potential mixture of about ten different antibody molecules, of which only about one might have the correct bispecific structure. The purification of the correct molecule is usually accomplished by affinity chromatography steps. Similar procedures are disclosed in WO 93/08829 and in Traunecker et al. (1991), *EMBO J.*, 10:3655-3659. Other methods for making bispecific antibodies are provided in, for example, Kufer et al. (2004), *Trends Biotech.*, 22:238-244.

Antibody variable domains with the desired binding specificities can be fused to immunoglobulin constant domain sequences. The fusion preferably is with an immunoglobulin heavy chain constant domain, comprising at least part of the hinge, $C_{H2}$ and $C_{H3}$ regions. It may have the first heavy chain constant region ($C_{H1}$) containing the site necessary for light chain binding present in at least one of the fusions. DNAs encoding the immunoglobulin heavy chain fusions and, if desired, the immunoglobulin light chain, are inserted into separate expression vectors, and are co-transformed into a suitable host organism. For further details of generating bispecific antibodies see, for example Suresh et al. (1986), *Meth. Enzym.*, 121:210-228.

Heteroconjugate antibodies are also contemplated by this invention. Heteroconjugate antibodies are composed of two covalently joined antibodies. Such antibodies have, for example, been proposed to target immune system cells to unwanted cells (U.S. Pat. No. 4,676,980). It is contemplated that the antibodies may be prepared in vitro using known methods in synthetic protein chemistry, including those involving cross-linking agents. For example, immunotoxins may be constructed using a disulfide exchange reaction or by forming a thioester bond. Examples of suitable reagents for that purpose include iminothiolate and methyl-4-mercaptobutyrimidate, and those disclosed, for example, in U.S. Pat. No. 4,676,980.

In addition, one can generate single domain antibodies to extended Type I chain antigen, in particular extended Type I chain glycosphingolipid. Examples of that technology have been described in WO 94/25591 for antibodies derived from Camelidae heavy chain Ig, as well as in US 20030130496 A1 describing the isolation of single domain fully human antibodies from phage libraries.

Alternatively, techniques described for the production of single chain antibodies (U.S. Pat. No. 4,946,778; Bird et al. (1988), Science 242:423-426; Huston et al. (1988), *Proc. Natl. Acad. Sci. USA*, 85:5879-5883; and Ward et al. (1989), *Nature*, 334:544-546) can be practiced. Single chain antibodies are formed by linking the heavy and light chain fragments of the Fv region via an amino acid bridge, resulting in a single chain polypeptide. Techniques for the assembly of functional Fv fragments in *E. coli* cells may also be used (Pollack et al. (1988), *Science*, 242:1038-1040). Single chain antibodies ("scFv") and a method of their construction are described in, for example, U.S. Pat. No. 4,946,778. Alternatively, Fab can be constructed and expressed by similar means. All of the wholly and partially human antibodies can be less immunogenic than wholly murine mAbs, and the fragments and single chain antibodies also can be less immunogenic.

This invention encompasses antibodies recombinantly fused or chemically conjugated (including both covalent and non-covalent conjugations) to a polypeptide. Fused or conjugated antibodies of this invention may be used for ease in purification, see e.g., WO 93/21232; EP 439,095 A2; Naramura et al. (1994), *Immunol Lett.*, 39:91-99; U.S. Pat. No. 5,474,981; Gillies et al. (1992), *Proc. Natl. Acad. Sci. USA*, 89:1428-1432; and Fell et al. (1991), *J. Immunol.*, 146:2446-2452.

The purification can be facilitated by using a recognition marker or tag. For example, the marker can be an amino acid sequence, such as, a hexa-histidine peptide, such as the tag provided in a pQE vector (Qiagen, Inc., Chatsworth, Calif.), among others, many of which are commercially available, Gentz et al., Proc Natl Acad Sci USA 86:821 (1989). Other peptide tags useful for purification include, but are not limited to, the "HA" tag, which corresponds to an epitope derived from the influenza hemagglutinin protein (Wilson et al. (1984), *Cell*, 37:767-778) and the "flag" tag.

Antibodies or antibody fragments can be isolated from antibody phage libraries generated using the techniques described in McCafferty et al. (1990), *Nature*, 348: 552-554. In Nature, 352:624 (1991) and *J. Mol. Biol.*, 222:581 (1991), Clarkson et al. and Marks et al. described the isolation of murine and human antibodies, respectively, using phage libraries. Subsequent publications describe the production of high affinity (nM range) human antibodies by chain shuffling (Marks et al. (1992), *Bio/Technology*, 10:779-783), as well as combinatorial infection and in vivo recombination as a strategy for constructing very large phage libraries (Waterhouse et al. (1993), *Nucl. Acids. Res.*, 21:2265-2266). Thus, the techniques are viable alternatives to traditional monoclonal antibody hybridoma techniques for isolation of monoclonal antibodies.

Candidate antibodies against extended Type I chain antigen, in particular extended Type I chain glycosphingolipid, can be tested by enzyme-linked immunosorbent assay (ELISA), FACS, Western immunoblotting or other immunochemical techniques, as known in the art. Thus, cells expressing extended Type I chain antigen can be used to detect antibody binding thereto using a known technique, or suitable membrane preparations containing extended Type I chain antigen or portion thereof, or purified or isolated extended Type I chain structures can be adhered to a solid phase and used as a capture element in an assay, configured as a design choice.

To determine whether a particular antibody homolog binds to human extended Type I chain antigen, in particular extended Type I chain glycosphingolipid, any conventional binding assay may be used. Useful binding assays for extended Type I chain antigen, in particular extended Type I chain glycosphingolipid, include FACS analysis, ELISA assays, radioimmunoassays and the like, which detect binding of antibody, and functions resulting therefrom, to human extended Type I chain antigen, in particular extended Type I chain glycosphingolipid. Full-length and soluble forms of human extended Type I chain antigen taught herein, in particular extended Type I chain glycosphingolipid, are useful in such assays. The binding of an antibody or homolog to extended Type I chain antigen, or to soluble fragments thereof, may conveniently be detected through the use of a second antibody specific for immunoglobulins of the species from which the antibody or homolog is derived. The second antibody can carry a detectable label or configured to be detected.

The ability of an antibody or homolog to bind to human extended Type I chain antigen, in particular extended Type I chain glycosphingolipid, can be evaluated by testing the ability thereof to bind to human extended Type I chain antigen[+] cells, in particular extended Type I chain glycosphingolipid[+] cells. Suitable extended Type I chain glycosphingolipid[+] cells for use in determining whether a particular antibody or homolog binds to human extended Type I chain glycosphingolipid are available from mammal tissue culture cells expressing extended Type I chain glycosphingolipid, e.g., on the cell surface.

Binding of the antibody or homolog to the extended Type I chain antigen[+] cells can be detected by staining the cells with, for example, a fluorescently labeled second antibody specific for immunoglobulins of the same species from which the antibody homolog being tested is derived. A fluorescence activated cell sorter ("FACS") can be used to detect and to quantify any binding, see generally, Practical Flow Cytometry, by Howard M. Shapiro, Alan R. Liss, Inc., New York, N.Y. (1985).

To determine whether a particular antibody or homolog causes no significant decrease in the number of circulating extended Type I chain antigen[+] cells in vivo, the number of circulating extended Type I chain antigen[+] cells isolated from a mammal within 24 hours after administration of the antibody or homolog to a mammal having normal immune function is quantified, and compared to the pre-administration number or the number in a control mammal to whom an isotype-matched antibody or homolog of irrelevant specificity has been administered instead of an antibody or homolog of this invention. Quantification of extended Type I chain antigen[+] cells in animals dosed with an antibody against extended Type I chain antigen, or a functional portion or derivative thereof, may be accomplished, for example, by staining obtained cells with fluorescently-labeled antibodies that bind the antibodies against extended Type I chain antigen, as well as labeled antibodies specific for T cells and B cells, followed by FACS analysis.

Antibodies of this invention may be described or specified in terms of the epitope(s) or portion(s) of extended Type I chain antigen, in particular extended Type I chain glycosphingolipid, to which the antibody recognizes or specifically binds. The epitope(s) may be specified as described herein, e.g., by physical means, such as mass spectrometry, and by compositional analysis of the saccharides, analyses of the molecules to which the sugars bind, analyses of conformational epitopes, etc.

Antibodies of this invention may also be described or specified in terms of cross-reactivity. Antibodies that bind extended Type I chain antigen, in particular extended Type I chain glycosphingolipid, which has at least 95%, at least 90%, at least 85%, at least 80%, at least 75%, at least 70%, at least 65%, at least 60%, at least 55%, and at least 50% identity (as calculated using methods known in the art and described herein) to the original antibody against extended Type I chain antigen, are also included in this invention.

Antibodies of this invention also may be described or specified in terms of binding affinity to an extended Type I chain antigen of interest, in particular extended Type I chain glycosphingolipid. Antibodies against extended Type I chain antigen, in particular extended Type I chain glycosphingolipid, may bind with a $K_D$ of less than about $10^{-7}$ M, less than about $10^{-6}$ M, or less than about $10^{-5}$ M. Higher binding affinities in an antibody of interest can be beneficial, such as those with an equilibrium dissociation constant or $K_D$ of from about $10^{-8}$ to about $10^{-15}$ M or lower, from about $10^{-8}$ to about $10^{-12}$ M, from about $10^{-9}$ to about $10^{-11}$ M, or from about $10^{-8}$ to about $10^{-10}$ M. This invention also provides antibodies that competitively inhibit binding of an antibody to an epitope of this invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

This invention also includes conjugates comprising an antibody of interest. The conjugates comprise two primary components, an antibody of interest and a second component, which may be a cell binding agent, a cytotoxic agent, a pharmacologically active agent, a drug and so on.

As used herein, the term "cell-binding agent" refers to an agent that specifically recognizes and binds to a molecule on the cell surface. Thus, the cell binding agent can be one that binds a CD antigen, a pathogen antigen, such as a virus antigen, a differentiation antigen, a cancer antigen, a cell-specific antigen, a tissue-specific antigen, an Ig or Ig-like molecule and so on.

Cell-binding agents may be of any type as presently known, or that become known, and includes peptides, non-peptides, saccharides, nucleic acids, ligands, receptors and so on, or combinations thereof. The cell-binding agent may be any compound that can bind a cell, either in a specific or non-specific manner. Generally, the agent can be an antibody (especially monoclonal antibodies), lymphokines, hormones, growth factors, vitamins, nutrient-transport molecules (such as transferrin), or any other cell-binding molecule or substance.

Other examples of cell-binding agents that can be used include: polyclonal antibodies; monoclonal antibodies; and fragments of antibodies such as Fab, Fab', F(ab')$_2$ and Fv fragments (Parham (1983), *J. Immunol.*, 131:2895-2902; Spring et al. (1974), *J. Immunol.*, 113:470-478; and Nisonoff et al. (1960), *Arch. Biochem. Biophys.*, 89: 230-244).

The second component also can be a cytotoxic agent. The term "cytotoxic agent" as used herein refers to a substance that reduces or blocks the function or growth of cells and/or causes destruction of cells. Thus, the cytotoxic agent can be a taxol, a maytansinoid, such as DM1 or DM4, CC-1065 or a CC-1065 analog, a ricin, a drug, mitomycin C and so on. In some embodiments, the cytotoxic agent, as with any binding agent of a conjugate of this invention, is covalently attached, directly or via a cleavable or non-cleavable linker, to an antibody of interest.

Examples of suitable maytansinoids include maytansinol and maytansinol analogs. Maytansinoids inhibit microtubule formation and are highly toxic to mammalian cells.

Examples of suitable maytansinol analogues include those having a modified aromatic ring and those having modifications at other positions. Such suitable maytansinoids are disclosed in U.S. Pat. Nos. 4,424,219, 4,256,746, 4,294,757, 4,307,016, 4,313,946, 4,315,929, 4,331,598, 4,361,650, 4,362,663, 4,364,866, 4,450,254, 4,322,348, 4,371,533, 6,333,410, 5,475,092, 5,585,499 and 5,846,545.

Examples of suitable analogues of maytansinol having a modified aromatic ring include: (1) C-19-dechloro (U.S. Pat. No. 4,256,746) (prepared, for example, by LAH reduction of ansamitocin P2); (2) C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using lithium aluminum hydride (LAH)); and (3) C-20-demethoxy, C-20-acyloxy (—OCOR), +/−dechloro (U.S. Pat. No. 4,294,757) (prepared by acylation using acyl chlorides).

Examples of suitable analogues of maytansinol having modifications at other positions include: (1) C-9-SH (U.S. Pat. No. 4,424,219) (prepared by the reaction of maytansinol with $H_2S$ or $P_2S_5$); (2) C-14-alkoxymethyl (demethoxy/$CH_2OR$) (U.S. Pat. No. 4,331,598); (3) $C_{1-4}$-hydroxymethyl or acyloxymethyl ($CH_2OH$ or $CH_2OAc$) (U.S. Pat. No. 4,450,254) (prepared from *Nocardia*); (4) C-15-hydroxy/acyloxy (U.S. Pat. No. 4,364,866) (prepared by the conversion of maytansinol by *Streptomyces*); (5) C-15-methoxy (U.S. Pat. Nos. 4,313,946 and 4,315,929) (isolated from *Trewia nudiflora*); (6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

The cytotoxic conjugates may be prepared by in vitro methods. To link a cytotoxic agent, drug or prodrug to the antibody, commonly, a linking group is used. Suitable linking groups are known in the art and include disulfide groups, thioether groups, acid labile groups, photolabile groups, peptidase labile groups and esterase labile groups. For example, conjugates can be constructed using a disulfide exchange reaction or by forming a thioether bond between an antibody of interest and the drug or prodrug.

The molecule conjugated to an antibody of interest can be a molecule with a pharmacologic activity, such as a drug, such as a small molecule or a biologic. Thus, the biologic can be a cytokine, for example. The molecule can be a prodrug, such as a drug ester. The molecule can be a radionuclide.

As discussed above, this invention provides isolated nucleic acid sequences encoding an antibody or functional variant thereof as disclosed herein, vector constructs comprising a nucleotide sequence encoding the extended Type I chain antigen-binding polypeptides of this invention, host cells comprising such a vector, and recombinant techniques for the production of the polypeptide that binds extended Type I chain antigen, in particular extended Type I chain glycosphingolipid.

The vector normally contains components known in the art and generally include, but are not limited to, one or more of the following: a signal sequence, an origin of replication, a promoter, a polyA sequence, one or more marker or selection genes, sequences facilitating and/or enhancing translation, an enhancer element and so on. Thus, the expression vectors include a nucleotide sequence operably linked to such suitable transcriptional or translational regulatory nucleotide sequences such as those derived from mammalian, microbial, viral or insect genes. Examples of additional regulatory sequences include operators, mRNA ribosomal binding sites, and/or other appropriate sequences which control transcription and translation, such as initiation and termination thereof. Nucleotide sequences are "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of that nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody or portion thereof. The signal peptide may be cleaved from the polypeptide on secretion of antibody from the host cell. Examples of such secretory signals are well known and include, e.g., those described in U.S. Pat. Nos. 5,698,435, 5,698,417 and 6,204,023.

The vector may be a plasmid, a single-stranded or double-stranded viral vector, a single-stranded or double-stranded RNA or DNA phage vector, a phagemid, a cosmid or any other carrier of a transgene of interest. Such vectors may be introduced into cells as polynucleotides by well known techniques for introducing DNA and RNA into cells. The vectors, in the case of phage and viral vectors also may be introduced into cells as packaged or encapsulated virus, or a virus-like particle by well known techniques for infection and transduction. Viral vectors may be replication competent or replication defective. In the latter case, viral propagation generally will occur only in complementing host cells and using plural vectors carrying the various virus components necessary to produce a particle. Cell-free translation systems may also be employed to produce the protein using RNAs derived from the present DNA constructs of interest (see, e.g., WO 86/05807 and WO 89/01036; and U.S. Pat. No. 5,122,464).

The antibodies of this invention can be expressed from any suitable host cell. Examples of host cells useful in this invention include prokaryotic, yeast or eukaryotic cells and include, but are not limited to, microorganisms such as bacteria (e.g., *E. coli, B. subtilis, Enterobacter, Erwinia, Klebsiella, Proteus, Salmonella, Serratia* and *Shigella*, as well as *Bacilli, Pseudomonas* and *Streptomyces*) transformed with recombinant bacteriophage DNA, plasmid DNA or cosmid DNA expression vectors containing the antibody coding sequences of interest; yeasts (e.g., *Saccharomyces, Pichia, Actinomycetes, Kluyveromyces, Schizosaccharomyces, Candida, Trichoderma, Neurospora*) and filamentous fungi, such as *Neurospora, Penicillium, Tolypocladium* and *Aspergillus*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; or tobacco mosaic virus, TMV) or transformed with recombinant plasmid expression vectors (e.g., Ti plasmid) containing antibody coding sequences; or mammalian cell systems (e.g., COS, CHO, BHK, 293 or 3T3 cells) harboring recombinant expression constructs containing promoters derived from the genome of mammalian cells (e.g., metallothionein promoter) or from mammalian viruses (e.g., the adenovirus late promoter, or the vaccinia virus 7.5K promoter).

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids, such as pKK223-3 (Pharmacia Fine Chemicals, Uppsala, Sweden), pGEM1 (Promega Biotec, Madison, Wis., USA), pET (Novagen, Madison, Wis., USA) and the pRSET (Invitrogen, Carlsbad, Calif., USA) series of vectors (Studier (1991), *J. Mol. Biol.*, 219:37-44; and Schoepfer (1993), *Gene*, 124:83-85). Promoter sequences commonly used for recombinant prokaryotic host cell expression vectors include T7 promoter (Rosenberg et al. (1987), *Gene*, 56:125-135), β-lactamase (penicillinase), lactose promoter (Chang et al. (1978), *Nature*, 275:615; and Goeddel et al. (1979), *Nature*, 281:544-548), tryptophan (trp) promoter system (Goeddel et al. (1980), *Nucl. Acids Res.*, 8:4057-4074), and tac promoter (Sambrook et al., Molecular Cloning, A Laboratory Manual, 2nd ed., Cold Spring Harbor Laboratory Press, Cold Spring Harbor, N.Y. (1990)).

Yeast vectors will often contain an origin of replication sequence, such as, from a 2μ yeast plasmid, an autonomously replicating sequence (ARS), a promoter region, sequences for polyadenylation, sequences for transcription termination and a selectable marker gene. Suitable promoter sequences for yeast vectors include, amongst others, promoters for metallothionein, 3-phosphoglycerate kinase (Hitzeman et al. (1980), *J. Biol. Chem.*, 255:2073) or other glycolytic enzymes (Holland et al. (1978), *Biochem.*, 17:4900-4907) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other suitable vectors and promoters for use in yeast expression are further described in Fleer et al. (1991), *Gene*, 107:285-295. Other suitable promoters and vectors for yeast and yeast transformation protocols are well known in the art. Yeast transformation protocols are well known. One such protocol is described by Hinnen et al. (1978), *Proc. Natl. Acad. Sci.*, 75:1929-1933, which selects for Trp$^+$ transformants in a selective medium.

Any eukaryotic cell culture is workable, whether from vertebrate or invertebrate culture. Examples include plant and insect cells (Luckow et al. (1988), Bio/Technology, 6:47-55; Miller et al., in Genetic Engineering, Setlow et al., eds., Vol. 8, pp. 277-9, Plenum Publishing Corp., New York (1986); and Maeda et al. (1985), *Nature*, 315:592-594). For example, Baculovirus systems may be used for production of heterologous proteins. In an insect system, *Autographa californica* nuclear polyhedrosis virus (AcNPV) may be used as a vector to express foreign genes. The virus grows in *Spodoptera frugiperda* cells. The antibody coding sequence may be cloned under control of an AcNPV promoter (for example, the polyhedrin promoter). Other hosts that have been identified include *Aedes, Drosophila melanogaster* and *Bombyx mori*. A variety of viral strains for transfection are publicly available, e.g., the L-1 variant of AcNPV and the Bm-5 strain of *Bombyx mori* NPV. Moreover, plant cell cultures of cotton, corn, potato, soybean, petunia, tomato, algae, duckweed and tobacco can also be utilized as hosts, as known in the art.

Vertebrate cells, and propagation of vertebrate cells, in culture (tissue culture) can be a routine procedure, although fastidious cell lines do exist which require, for example, a specialized medium with unique factors, feeder cells and so on, see Tissue Culture: methods and applications, Kruse et al., eds., Academic Press, Inc. New York (1973). Examples of useful mammal host cell lines are monkey kidney cell lines; human embryonic kidney cell lines; baby hamster kidney cell lines; Chinese hamster ovary (CHO) cell lines, Urlaub et al. (1980), *Proc. Natl. Acad. Sci. USA*, 77:4216-4220); mouse Sertoli cell lines; human cervical carcinoma (for example, HeLa) cell lines; canine kidney cell lines; human lung cell lines; human liver cell lines; mouse mammary tumor cell lines; and NSO cell lines.

Host cells are transformed with vectors for antibody production and cultured in conventional nutrient medium containing growth factors, vitamins, minerals and so on, as well as inducers appropriate for the cells and vectors used. Commonly used promoter sequences and enhancer sequences are derived, for example, from polyoma virus, Adenovirus 2, Simian virus 40 (SV40) and human cytomegalovirus (CMV). DNA sequences derived from the SV40 viral genome may be used to provide other genetic elements for expression of a structural gene sequence in a mammalian host cell, including, e.g., SV40 origin, early and late promoter, enhancer, splice and polyadenylation sites. Viral early and late promoters are particularly useful because both are easily obtained from a viral genome as a fragment which may also contain a viral origin of replication. Exemplary expression vectors for use in mammalian host cells are commercially available.

Commercially available medium such as Ham's F10, Minimal Essential Medium (MEM), RPMI-1640 and Dulbecco's Modified Eagle's Medium (DMEM) are suitable for culturing host cells. In addition, any of the media described in Ham et al. (1979), *Meth. Enzymol.,* 58:44-93 and Barnes et al. (1980), *Anal. Biochem.,* 102:255-270, and in U.S. Pat. No. 4,767,704, 4,657,866, 4,560,655, 5,122,469, 5,712,163 or 6,048,728, may be used as a culture medium for the host cells. Any of those media may be supplemented as necessary with hormones and/or other growth factors (such as insulin, transferrin or epidermal growth factor), salts (such as chlorides, such as sodium, calcium or magnesium chloride; and phosphates), buffers (such as HEPES), nucleotides (such as adenosine and thymidine), antibiotics, trace elements (which may be defined as inorganic compounds usually present at final concentrations in the micromolar range) and glucose or an equivalent energy source. Any other necessary supplements may be included at appropriate concentrations, as a design choice. The culture conditions, such as temperature, pH and the like, are as known in the art appropriate for the cell and to enable the desired expression of the transgene.

The polynucleotides of interest may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al. (1994), *Bio/Techniques,* 17:242) and then amplifying the ligated oligonucleotides, for example, by PCR.

Alternatively, a polynucleotide encoding an antibody may be generated from nucleic acid of a cell expressing same. If a clone containing a nucleic acid encoding a particular antibody is not available, but the sequence of the antibody molecule is known, a nucleic acid encoding the immunoglobulin may be obtained from a suitable source, such as a library, which may be one specific for antibody-producing cells, such as hybridoma cells selected to express an antibody of this invention. Suitable primers can be configured for PCR amplification. Amplified nucleic acids generated by PCR may then be cloned into replicable cloning vectors using any method known in the art.

Once the nucleotide sequence and corresponding amino acid sequence of the antibody are determined, the nucleotide sequence of the antibody may be manipulated to obtain the equivalents of interest described herein using methods known in the art for manipulating nucleotide sequences, including, e.g., recombinant DNA techniques, site directed mutagenesis, PCR, etc. (see, for example, Sambrook et al., Molecular Cloning, A Laboratory Manual, 2nd ed., Cold Spring Harbor Laboratory Press, Cold Spring Harbor, N.Y. (1990); and Current Protocols in Molecular Biology, Ausubel et al. eds., John Wiley & Sons, Inc., New York (1998)) to generate antibodies having a different amino acid sequence, for example, to create amino acid substitutions, deletions and/or insertions.

The amino acid sequence of the heavy and/or light chain variable domain may be inspected to identify the sequences of the CDR's by well known methods, e.g., by comparison to known amino acid sequences of other heavy and light chain variable regions to determine the regions of sequence hypervariability. Using routine recombinant DNA techniques, one or more of the CDR's may be inserted within framework regions, e.g., into human framework regions to humanize a non-human antibody, as described supra. The polynucleotide of interest, generated by the combination of nucleotide sequences encoding the framework regions and one or more CDR's, encodes a molecule that specifically binds extended Type I chain antigen, in particular extended Type I chain glycosphingolipid, or at least the carbohydrate epitopes and structure recognized thereby. For example, such methods may be used to make amino acid substitutions or deletions of one or more cysteine residues participating in an intrachain disulfide bond to generate antibody molecules lacking one or more intrachain disulfide bonds.

The antibodies or antibody fragments of this invention can be used to detect extended Type I chain antigen, in particular extended Type I chain glycosphingolipid, and hence cells expressing extended Type I chain antigen, in particular extended Type I chain glycosphingolipid, in a biological sample in vitro or in vivo. In one embodiment, the antibody against extended Type I chain antigen according to this invention is used to determine the presence of and the level of extended Type I chain antigen in a tissue or in cells derived from the tissue. The levels of extended Type I chain antigen in the tissue or biopsy can be determined, for example, in an immunoassay with the antibodies or antibody fragments of this invention. The tissue or biopsy thereof can be frozen or fixed. The same or other methods can be used to determine other properties of extended Type I chain antigen, such as the level thereof, cellular localization and so on.

The above-described method can be used, for example, to diagnose a cancer in a subject known to have or suspected to have a cancer, wherein the level of extended Type I chain antigen, in particular extended Type I chain glycosphingolipid, measured in said patient is compared with that of a normal reference subject or standard.

This invention further provides for monoclonal antibodies, humanized antibodies and epitope-binding fragments thereof that are further labeled for use in research or diagnostic applications. In some embodiments, the label is a radiolabel, a fluorophore, a chromophore, an imaging agent or a metal ion, for example.

A method for diagnosis is also provided in which said labeled antibodies or epitope-binding fragments thereof are administered to a subject suspected of having a cancer, arthritis, autoimmune diseases or other diseases related to, caused by or associated with the aberrant or abnormal expression and/or function of extended Type I chain antigen, in particular extended Type I chain glycosphingolipid, and the distribution of the label within the body of the subject is measured or monitored.

The antibody and fragments thereof of this invention may be used as affinity purification agents. In that process, the antibodies are immobilized on a solid phase, such as a dextran or agarose, resin or filter paper, using methods known in the art. The immobilized antibody is contacted with a sample containing extended Type I chain antigen, in particular extended Type I chain glycosphingolipid, or cells carrying same to be purified, and thereafter the support is washed with a suitable solvent that will remove substantially all the material in the sample except the extended Type I chain antigen, in particular extended Type I chain glycosphingolipid, or cell to be purified, which is bound to the immobilized antibody of interest. Finally, the support is washed with another suitable solvent, such as glycine buffer (pH 5.0) that will release the extended Type I chain antigen, in particular extended Type I chain glycosphingolipid, or cell from the antibody of interest.

For diagnostic applications, the antibody of interest typically will be labeled with a detectable moiety or marker. Numerous labels are available which can be generally grouped into the following categories: (a) radioisotopes, such as $^{36}S$, $^{14}C$, $^{125}I$, $^3H$ and $^{131}I$ (the antibody can be labeled with the radioisotope using a technique described in, for example, Current Protocols in Immunology, Vol. 12, Coligan et al., ed., Greene Publishing Associates and Wiley-Interscience, New York (1991), and radioactivity can be measured using scintillation counting); (b) fluorescent labels, such as rare earth chelates (europium chelates), fluorescein and derivatives thereof rhodamine and derivatives thereof, dansyl, lissamine, phycoerythrin and Texas Red, in which the fluorescent labels can be conjugated to the antibody using a technique disclosed in Current Protocols in Immunology, supra, for example, where fluorescence can be quantified using a fluorimeter; and (c) various enzyme substrate labels are available (U.S. Pat. No. 4,275,149 provides a review), in which the enzyme generally catalyzes a chemical alteration of a chromogenic substrate which can be measured using various techniques, for example, the enzyme may catalyze a color change in a substrate, which can be measured spectrophotometrically, or the enzyme may alter the fluorescence or chemiluminescence of the substrate. Techniques for quantifying a change in fluorescence are known, for example, using a luminometer, or the label donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase and glucose-6-phosphate dehydrogenase), heterocyclic oxidases (such as uricase and xanthine oxidase), lactoperoxidase, microperoxidase and the like. Techniques for conjugating enzymes to antibodies are described by O'Sullivan et al. in Methods in Enzymology, J. J. Langone and H. Van Vunakis, eds., Vol. 73 (Academic Press, New York, N.Y., 1981), pp. 147-166.

When such labels are used, suitable substrates are available, such as: (i) for horseradish peroxidase with hydrogen peroxide as a substrate, wherein the hydrogen peroxide oxidizes a dye precursor, e.g., orthophenylene diamine (OPD) or 3,3',5,5'-tetramethylbenzidine hydrochloride (TMB); (ii) for alkaline phosphatase (AP) with p-nitrophenyl phosphate as the chromogenic substrate; and (iii) β-D-galactosidase (β-D-Gal) with a chromogenic substrate (e.g., p-nitrophenyl β-D-galactosidase) or a fluorogenic substrate such as, 4-methylumbelliferyl-β-D-galactosidase.

Other enzyme-substrate combinations are available to those skilled in the art. For a general review, see U.S. Pat. Nos. 4,275,149 and 4,318,980.

Sometimes, the label is indirectly conjugated with the antibody. For example, the antibody can be conjugated with biotin and any of the reporters mentioned above can be conjugated with avidin, or vice versa. Biotin binds selectively to avidin and thus, the label can be conjugated with the antibody in that indirect manner. Various avidins are known in the art. Alternatively, to achieve indirect conjugation of the label, the antibody can be conjugated with a small hapten (e.g., digoxin) and one of the different types of labels or reporters mentioned above is conjugated with an anti-digoxin antibody. Thus, indirect conjugation of the label with the antibody or mutein can be achieved using a second antibody.

In another embodiment of this invention, the antibody need not be labeled, and the presence thereof can be detected using a labeled antibody which binds to the antibody, another form of a second antibody.

The antibodies of this invention may be employed in any known assay method, such as competitive binding assays, direct and indirect sandwich assays, immunoprecipitation and immunohistochemistry assays. See Zola, Monoclonal Antibodies: A Manual of Techniques, CRC Press, Inc., Boca Raton, Fla. (1987).

Competitive binding assays rely on the ability of a labeled standard to compete with the test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, determinant or epitope, of the target to be detected. In a sandwich assay, the test sample to be analyzed is bound by a first antibody which is immobilized directly or indirectly on a solid support, and thereafter a second antibody directly or indirectly labeled binds to the bound test sample, thus forming an insoluble three-part complex, see e.g., U.S. Pat. No. 4,376,110. The second antibody may itself be labeled with a detectable moiety (direct sandwich assays) or may be measured using an anti-immunoglobulin antibody or other suitable member of the binding pair (antibody/antigen, receptor/ligand, enzyme/substrate, for example) that is labeled with a detectable moiety (indirect sandwich assay). For example, one type of sandwich assay is an ELISA assay, in which case the detectable moiety is an enzyme.

For immunohistochemistry, the cell or tissue sample may be fresh or frozen or may be embedded in paraffin and fixed with a preservative such as formalin, for example.

The antibodies may also be used for in vivo diagnostic assays. Generally, the antibody or variant thereof is labeled with a radionucleotide (such as $^{111}In$, $^{99}Tc$, $^{14}C$, $^{131}I$, $^3H$, $^{32}P$ or $^{35}S$) so that the sites expressing extended Type I chain antigen, in particular extended Type I chain glycosphingolipid, can be localized using, for example, immunoscintigraphy and a gamma camera.

This invention also includes kits, e.g., comprising an antibody, fragment thereof, homolog, derivative thereof and so on, such as a labeled or cytotoxic conjugate, and instructions for the use of the antibody or the conjugate for killing or labeling particular cell types and so on. The instructions may include directions for using the antibody, conjugate and so on in vitro, in vivo or ex vivo. The antibody can be in liquid form or as a solid, generally lyophilized. The kit can contain suitable other reagents, such as a buffer, a reconstituting solution and other necessary ingredients for the intended use. A packaged combination of reagents in predetermined amounts with instructions for use thereof, such as, for a therapeutic use for performing a diagnostic assay is contemplated. Where the antibody is labeled, such as with an enzyme, the kit can include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied to provide for concentrates of a solution of a reagent, which provides user flexibility, economy of space, economy of reagents and so on. The reagents may be provided as dry powders, usually lyophilized, including excipients, which on dissolution provide a reagent solution having the appropriate concentration.

The antibodies of this invention may be used to treat a mammal. In one embodiment, the antibody or equivalent of interest is administered to a non-human mammal for the purposes of obtaining preclinical data, for example. Exemplary non-human mammals to be treated include non-human primates, dogs, cats, rodents and other mammals in which preclinical studies are performed. Such mammals may be established animal models for a disease to be treated with the antibody, or may be used to study toxicity of the antibody of interest. In each of those embodiments, dose escalation studies may be performed in the mammal. The product of interest may have therapeutic use in those animals as well.

An antibody, with or without a second component, such as a therapeutic moiety conjugated to same, administered alone or in combination with a cytotoxic factor(s), can be used as a therapeutic. This invention is directed to antibody-based therapies which involve administering antibodies of this invention to an animal, a mammal or a human, for treating an extended Type I chain antigen-mediated or associated disease, disorder or condition. The animal or subject may be a mammal in need of a particular treatment, such as a mammal having been diagnosed with a particular disorder, e.g., one relating to extended Type I chain antigen, in particular extended Type I chain glycosphingolipid, or associated with abnormal extended Type I chain structure expression and function. Antibodies directed against extended Type I chain antigen, in particular extended Type I chain glycosphingolipid, are useful, for example, for prophylaxis or treatment of cancer and autoimmune disorders, for example. For example, by administering a therapeutically acceptable dose of an antibody against extended Type I chain antigen according to this invention, or a cocktail of a plurality of the instant antibodies or equivalents thereof, or in combination with other antibodies of varying sources, or in combination with a non-antibody drug, such as, an anti-inflammatory drug, a cytotoxic agent, an antibiotic and so on, such as, a platinum drug, methotrexate and so on, disease symptoms may be ameliorated or prevented in the treated mammal, particularly humans.

Therapeutic compounds of this invention include, but are not limited to, antibodies of this invention (including fragments, analogs, equivalents and derivatives thereof as described herein) and nucleic acids encoding antibodies of this invention as described herein (including fragments, analogs and derivatives thereof) and anti-idiotypic antibodies as described herein. The antibodies of this invention can be used to treat, inhibit or prevent diseases, disorders or conditions associated with aberrant expression and/or activity of extended Type I chain antigen, in particular extended Type I chain glycosphingolipid, including, but not limited to, any one or more of the diseases, disorders, or conditions described herein. The treatment and/or prevention of diseases, disorders or conditions associated with aberrant expression and/or activity of extended Type I chain antigen, in particular extended Type I chain glycosphingolipid, includes, but is not limited to, alleviating at least one symptom associated with those diseases, disorders, or conditions. Antibodies of this invention may be provided in pharmaceutically acceptable compositions as known in the art or as described herein. The terms "physiologically acceptable," "pharmacologically acceptable," "pharmaceutically acceptable" and so on mean approved by a regulatory agency of the Federal or a state government or listed in the U.S. Pharmacopeia or other generally recognized pharmacopeia for use in animals and more particularly in humans.

The antibody against extended Type I chain antigen, in particular extended Type I chain glycosphingolipid, can be administered to a mammal in any acceptable manner. Methods of introduction include, but are not limited to, parenteral, subcutaneous, intraperitoneal, intrapulmonary, intranasal, epidural, inhalation and oral routes, and if desired for immunosuppressive treatment, intralesional administration. Parenteral infusions include intramuscular, intradermal, intravenous, intraarterial or intraperitoneal administration. The antibodies or compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the therapeutic antibodies or compositions of this invention into the central nervous system by any suitable route, including intraventricular and intrathecal injection; intraventricular injection may be facilitated by an intraventricular catheter, for example, attached to a reservoir, such as an Ommaya reservoir. In addition, the antibody can be suitably administered by pulse infusion, particularly with declining doses of the antibody. Preferably, the dosing is given by injection, more preferably by intravenous or subcutaneous injections, depending, in part, on whether the administration is brief or chronic.

Various other delivery systems are known and can be used to administer an antibody of this invention, including, e.g., encapsulation in liposomes, microparticles, microcapsules and so on (see Langer (1990), *Science,* 249:1527-1533); expression of an antibody, mutein thereof or antigen-binding portion thereof, of interest on a liposome, particle, capsule and so on to yield a targeting vehicle (Treat et al., in Liposomes in the Therapy of Infectious Disease and Cancer, Lopez-Berestein et al., eds., Liss, New York, pp. 353-365 (1989); and Lopez-Berestein, ibid., pp. 317-327); recombinant cells capable of expressing the compound, see, e.g., Wu et al. (1987), *J. Biol. Chem.,* 262:4429-4432; construction of a nucleic acid as part of a retroviral or other vector; and so on.

The active ingredients may also be entrapped, for example, by coascervation techniques or by interfacial polymerization, in a microcapsule made of, for example, hydroxymethylcellulose, gelatin or poly(methylmethacylate), respectively, in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, A. Osal, ed., Mack Publishing Co., Easton, Pa. (1980). When the liposome or particle expresses an antibody of interest, any of a variety of compounds can be carried in the liposome, such as a non-antibody drug, small molecule drug and so on. The instant antibody can thus serve a targeting function.

Pulmonary administration can also be employed, e.g., by use of an inhaler or nebulizer, and formulation with an aerosolizing agent. The antibody may also be administered into the lungs of a patient in the form of a dry powder composition, see e.g., U.S. Pat. No. 6,514,496.

In a specific embodiment, it may be desirable to administer the therapeutic antibodies or compositions of this invention locally to the area in need of treatment; that may be achieved by, for example, and not by way of limitation, local infusion, topical application, by injection, by means of a catheter, by means of a suppository or by means of an implant, said implant being of a porous, non-porous or gelatinous material, including membranes, such as silastic membranes or fibers. Preferably, when administering an antibody of this invention, care is taken to use materials to which the protein does not absorb or adsorb.

In yet another embodiment, the antibody can be delivered via a controlled release system. In one embodiment, a pump may be used (see Langer (1990), Science, 249:1527-1533; Sefton (1987), CRC Crit. Rev. Biomed. Eng., 14:201-240; Buchwald et al. (1980), Surgery, 88:507-516; and Saudek et al. (1989), N. Engl. J, Med., 321:574-579). In another embodiment, polymeric materials can be used (see Medical Applications of Controlled Release, Langer et al., eds., CRC Press Inc., Boca Raton, Fla. (1984); Controlled Drug Bioavailability, Drug Product Design and Performance, Smolen et al., eds., Wiley-Interscience, Inc., New York (1984); Ranger et al. (1983), J. Macromol. Sci. Rev. Macromol. Chem., 23:61; see also Levy et al. (1985), Science, 228:190-192; During et al. (1989), Ann. Neurol., 25:351-356; and Howard et al. (1989), J. Neurosurg., 71:105-112). In yet another embodiment, a controlled release system can be placed in proximity of the therapeutic target.

Sustained-release preparations may be prepared. Suitable examples of sustained-release preparations include semi-permeable matrices of solid hydrophobic polymers containing the antibody, which matrices are in the form of shaped articles, e.g., films or matrices. Examples of sustained-release matrices include polyesters, hydrogels (for example, poly(2-hydroxyethylmethacrylate), poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers (such as injectable microspheres composed of lactic acid-glycolic acid copolymer) and poly D-(−)-3-hydroxybutyric acid. While polymers such as ethylene vinyl acetate and lactic acid-glycolic acid enable release of molecules for over 100 days, certain hydrogels release proteins for shorter time periods. Rational strategies can be devised for stabilization depending on the mechanism involved. For example, if the aggregation mechanism is discovered to be intermolecular S—S bond formation through thio-disulfide interchange, stabilization may be achieved by modifying sulthydryl residues, lyophilizing from acidic solutions, controlling moisture content, using appropriate additives, amino acid substitution and developing specific polymer matrix compositions.

Therapeutic formulations of the polypeptide or antibody may be prepared for storage as lyophilized formulations or aqueous solutions by mixing the polypeptide having the desired degree of purity with optional "pharmaceutically acceptable" carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th edition, A. Osal, ed., Mack Publishing Co., Easton, Pa. (1980). Such additives are generally nontoxic to the recipients at the dosages and concentrations employed, hence, the excipients, diluents, carriers and so on are pharmaceutically acceptable.

An "isolated" or "purified" antibody is substantially free of cellular material or other contaminating proteins from the cell or tissue source or medium from which the protein is derived, or substantially free of chemical precursors or other chemicals when chemically synthesized. The language "substantially free of cellular material" includes preparations of an antibody in which the polypeptide/protein is separated from cellular components of the cells from which same is isolated or recombinantly produced. Thus, an antibody that is substantially free of cellular material includes preparations of the antibody having less than about 30%, 20%, 10%, 5%, 2.5% or 1% (by dry weight) of contaminating protein or cellular or subcellular material. When the antibody is recombinantly produced, it is also preferably substantially free of culture medium, i.e., culture medium represents less than about 20%, 10%, 5%, 2.5% or 1% of the volume of the protein preparation. When the antibody is produced by chemical synthesis, it is preferably substantially free of chemical precursors or other chemicals and reagents, i.e., the antibody of interest is separated from chemical precursors or other chemicals which are involved in the synthesis of the antibody. Accordingly, such preparations of the antibody have less than about 30%, 20%, 10%, 5% or 1% (by dry weight) of chemical precursors or compounds other than antibody of interest. In a preferred embodiment of the present invention, antibodies are isolated or purified.

As used herein, the phrase "low to undetectable levels of aggregation" refers to samples containing no more than 5%, no more than 4%, no more than 3%, no more than 2%, no more than 1% and often no more than 0.5% aggregation of antibody or variant thereof, that is, two or more antibody molecules or variants thereof joined or coalesced together, by weight of protein, as measured by, for example, high performance size exclusion chromatography (HPSEC).

As used herein, the term "low to undetectable levels of fragmentation" refers to samples containing equal to or more than 80%, 85%, 90%, 95%, 98% or 99% of intact antibody molecule or variant thereof, of the total protein, for example, in a single peak, as determined by HPSEC, or in two (2) peaks (heavy chain and light chain) by, for example, reduced capillary gel electrophoresis (rCGE) and containing no other single peaks having more than 5%, more than 4%, more than 3%, more than 2%, more than 1% or more than 0.5% of the total protein, each. The rCGE as used herein refers to capillary gel electrophoresis under reducing conditions sufficient to reduce disulfide bonds in an antibody or antibody-type or derived molecule.

This invention provides methods for preparing liquid formulations of the antibody or extended Type I chain antigen-binding fragment thereof, said methods comprising concentrating a fraction of purified antibody to a final concentration of about 15 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 200 mg/mL, about 2500 mg/mL, about 300 mg/mL or more using, for example, a semi-permeable membrane with an appropriate molecular weight (mw) cutoff (e.g., 30 kD cutoff for F(ab')$_2$ fragments thereof; and 10 kD cutoff for Fab fragments) and, optionally, diafiltering the concentrated antibody fraction into the formulation buffer using the same membrane.

In addition, the present invention also encompasses stable liquid formulations of the products of interest that can have improved half-life in vivo. Thus, the antibody of interest has a half-life in a subject, preferably a human, of greater than 3 days, greater than 7 days, greater than 10 days, greater than 15 days, greater than 25 days, greater than 30 days, greater than 35 days, greater than 40 days, greater than 45 days, greater than 2 months, greater than 3 months, greater than 4 months, greater than 5 months or more.

As used herein, the terms "stability" and "stable" in the context of a liquid formulation comprising an antibody against extended Type I chain antigen or an antigen-binding fragment thereof refer to the resistance of the antibody or antigen-binding fragment thereof in the formulation to thermal and chemical unfolding, aggregation, degradation or fragmentation under given manufacture, preparation, transportation and storage conditions. The "stable" formulations of this invention retain biological activity equal to or more than 80%, 85%, 90%, 95%, 98%, 99% or 99.5% under given manufacture, preparation, transportation and storage conditions. The stability of said antibody preparation can be assessed by degrees of aggregation, degradation or fragmentation by methods known to those skilled in the art, including, but not limited to, rCGE, sodium dodecyl sulfate polyacrylamide gel electrophoresis (SDS-PAGE) and high performance size exclusion chromatography (HPSEC), compared to a reference, for a predetermined period of time under selected storage conditions as a design choice.

This invention encompasses liquid formulations having stability at temperatures found in a commercial refrigerator or freezer found in the office of a physician or laboratory, such as from about −20° C. to about 5° C., said stability assessed, for example, by HPSEC, for storage purposes, such as, for about 60 days, for about 120 days, for about 180 days, for about a year for about 2 years or more. The liquid formulations of this invention also exhibit stability, as assessed, for example, by HSPEC, at room temperatures, for at least a few hours, such as about one hour, about two hours or about three hours prior to use.

The term "carrier" refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. The compositions can take the form of solutions, suspensions, emulsions, tablets, pills, capsules, powders, sustained-release formulations, depots and the like. The composition can be formulated as a suppository, with traditional binders and carriers such as triglycerides. Oral formulations can include standard carriers (such as pharmaceutical grades of mannitol, lactose, starch, magnesium stearate, sodium saccharine, cellulose, magnesium carbonate, etc.), flavorants, colorants, odorants and so on. Examples of suitable carriers are described in Remington's Pharmaceutical Sciences, 13th edition, Martin et al. eds., Mack Publishing Co., Easton, Pa. (1965). Such compositions will contain an effective amount of the antibody, preferably in purified form, together with a suitable amount of carrier so as to provide the form for proper administration to the patient. As known in the art, the formulation will be constructed to suit the mode of administration.

Buffering agents help to maintain the pH in a range which approximates physiological conditions or conditions conducive to antibody stability. Buffers are preferably present at a concentration ranging from about 2 mM to about 50 mM. Suitable buffering agents for use with this invention include both organic and inorganic acid and salts thereof, such as, for example, citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid sodium-hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffers (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.), and acetate buffers (e.g., acetic acid-sodium acetate mixture, acetic acid-sodium hydroxide mixture, etc.). Phosphate buffers, carbonate buffers, histidine buffers, trimethylamine salts such as Tris, HEPES and other such known buffers can be used.

Preservatives may be added to retard microbial growth, and may be added in amounts ranging from about 0.2% to about 1% (w/v). Suitable preservatives for use with this invention include phenol, benzyl alcohol, m-cresol, methyl paraben, propyl paraben, octadecyldimethylbenzyl ammonium chloride, benzylkonium halides (e.g., chloride, bromide and iodide), hexamethonium chloride, alkyl parabens; (such as methyl or propyl paraben), catechol, resorcinol, cyclohexanol and 3-pentanol.

Isotonicifiers are present to ensure physiological isotonicity of liquid compositions of the instant invention and include polhydric sugar alcohols, such as trihydric or higher sugar alcohols, such as glycerin, erythritol, arabitol, xylitol, sorbitol and mannitol. Polyhydric alcohols can be present in an amount of between about 0.1% to about 25%, by weight, preferably about 1% to about 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, arabitol, erythritol, mannitol, sorbitol, xylitol, ribitol, myoinositol, galactitol, glycerol and the like, including cyclitols such as inositol; polyethylene glycol; amino acid polymers; sulfur-containing reducing agents, such as thio-urea, glutathione, thioctic acid, sodium thioglycolate, thioglycerol, α-monothioglycerol and sodium thiosulfate; low molecular weight polypeptides (i.e., <10 amino acid residues); proteins, such as human serum albumin, bovine serum albumin, gelatin or immunoglobulins; hydrophilic polymers, such as polyvinylpyrrolidone, saccharides: monosaccharides, such as xylose, mannose, fructose, glucose; disaccharides, such as lactose, maltose and sucrose; trisaccharides such as raffinose; polysaccharides such as dextran and so on. Stabilizers can be present in the range from about 0.1 to about 10,000 w/w per part of active protein.

Additional miscellaneous excipients can include bulking agents, (e.g., agar, gelatin, starch and so on), chelating agents (e.g., EDTA), antioxidants (e.g., ascorbic acid, methionine or vitamin E) and cosolvents.

As used herein, the term "surfactant" refers to organic substances having amphipathic structures, namely, are composed of groups of opposing solubility tendencies, typically an oil soluble hydrocarbon chain and a water soluble ionic group. Surfactants can be classified, depending on the charge of the surface active moiety, into anionic, cationic and non-ionic surfactants. Surfactants often are used as wetting, emulsifying, solubilizing and dispersing agents for various pharmaceutical compositions and preparations of biological materials as those discussed herein.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80, etc.), polyoxamers (184, 188, etc.), Pluronic® polyols and polyoxyethylene sorbitan monoethers (TWEEN-20®, TWEEN-80®, etc.). Non-ionic surfactants may be present in a range of about 0.05 mg/mL to about 1.0 mg/mL, preferably about 0.07 mg/mL to about 0.2 mg/mL.

As used herein, the term "inorganic salt" refers to any compound, containing no carbon, that results from replacement of part or all of the acid hydrogen or an acid by a metal or a group acting like a metal, and often are used as a tonicity adjusting compound in pharmaceutical compositions and preparations of biological materials. The most common inorganic salts are NaCl, KCl, $NaH_2PO_4$, etc.

This invention provides liquid formulations of an extended Type I chain antigen-binding compound or fragment thereof, having a pH ranging from about 5.0 to about 7.0, or about 5.5 to 6.5, or about 5.8 to about 6.2, or about 6.0.

The formulation herein also may contain more than one active compound as necessary for the particular indication being treated, preferably those with complementary activities that do not adversely impact each other. For example, it may be desirable to further provide an immunosuppressive agent. Such molecules suitably are present in combination in amounts that are effective for the purpose intended. The formulation also can contain another drug, or a small molecule, a pharmacologic agent, such as an anti-neoplastic drug, such as cisplatin.

The term "small molecule" and analogous terms include, but are not limited to, peptides, peptidomimetics, amino acids, amino acid analogues, organic compounds, pharmacologically active agents, such as drugs, polynucleotides, polynucleotide analogues, nucleotides, nucleotide analogues, organic or inorganic compounds (i.e., including heterorganic and/or oganometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Thus, in the case of cancer, the antibodies of this invention may be administered alone or in combination with other types of cancer treatments, including conventional chemotherapeutic agents (paclitaxel, carboplatin, cisplatin and doxorubicin), anti-EGFR agents (gefitinib, erlotinib and cetuximab), anti-angiogenesis agents (bevacizumab and sunitinib), as well as immunomodulating agents, such as interferon-α and thalidomide.

As used herein, the terms "therapeutic agent" and "therapeutic agents" refer to any agent(s) which can be used in the treatment, management or amelioration of a disease, disorder, malady and the like associated with aberrant expression, and metabolism in general, and activity of extended Type I chain antigen, in particular extended Type I chain glycosphingolipid. Also included are known compounds with a pharmacologic effect in treating a disorder and so on that is associated with aberrant expression, metabolism or activity of extended Type I chain antigen, in particular extended Type I chain glycosphingolipid.

The antibody or variant, optionally, is formulated with one or more agents currently used to prevent or treat the disorder in question. The effective amount of such other agents depends on the amount of antibody present in the formulation, the type of disorder or treatment and other factors discussed above. These are generally used in the same dosages and with administration routes as used hereinbefore or about from 1 to 99% of the heretofore employed dosages.

The formulations to be used for in vivo administration must be sterile. That can be accomplished, for example, by filtration through sterile filtration membranes. For example, the liquid formulations of this invention may be sterilized by filtration using a 0.2 μm or a 0.22 μm filter.

In addition, the antibodies of this invention may be conjugated to various effector molecules such as heterologous polypeptides, drugs, radionucleotides or toxins, see, e.g., WO 92/08495; WO 91/14438; WO 89/12624; U.S. Pat. No. 5,314, 995; and EP 0396387 A2. An antibody or fragment thereof may be conjugated to a therapeutic moiety such as a cytotoxin (e.g., a cytostatic or cytocidal agent), a therapeutic agent or a radioactive metal ion (e.g., α-emitters, such as, for example, $^{213}Bi$). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicine, doxorubicin, daunorubicin, dihydroxy anthracenedione, mitoxantrone, mithramycin, actinomycin D, 1-dehydrotestosterone, glucocorticoids, procaine, tetracaine, lidocaine, propranolol and puromycin and analogs or homologues thereof. Therapeutic agents include, but are not limited to, antimetabolites (e.g., methotrexate, 6-mercaptopurine, 6-thioguanine, cytarabine, 5-fluorouracil and decarbazine), alkylating agents (e.g., mechlorethamine, chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin, daunomycin and doxorubicin), antibiotics (e.g., dactinomycin, actinomycin, bleomycin, mithramycin and anthramycin (AMC)), and anti-mitotic agents (e.g., vincristine and vinblastine).

To prolong the serum circulation of an antibody in vivo, various techniques can be used. For example, inert polymer molecules, such as high molecular weight polyethylene glycol (PEG), can be attached to an antibody with or without a multifunctional linker either through site-specific conjugation of the PEG to the N-terminus or to the C terminus of the antibody or via s-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion exchange chromatography. PEG-derivatized antibodies can be tested for binding activity as well as for in vivo efficacy using methods known to those of skilled in the art, for example, by immunoassays described herein.

An antibody having an increased half-life in vivo can also be generated by introducing one or more amino acid modifications (i.e., substitutions, insertions or deletions) into an IgG constant domain, or FA-binding fragment thereof (such as an Fc or hinge Fc domain fragment), see, e.g., WO 98/23289; WO 97/34631; and U.S. Pat. No. 6,277,375.

Further, an antibody can be conjugated to albumin to make an antibody more stable in vivo or to have a longer half-life in vivo. The techniques are known in the art, see e.g., WO 93/15199, WO 93/15200 and WO 01/77137; and EP 0413622 A1. The antibody also can be modified, for example, by glycosylation, acetylation, phosphorylation, amidation, derivatization by known protecting/blocking groups, proteolytic cleavage, linkage to a cellular ligand or other protein and so on.

Techniques for conjugating such a therapeutic moiety to antibodies are well known, see, e.g., Amon et al., in Monoclonal Antibodies and Cancer Therapy, Vol. 27, pp. 243-256, R. A. Reisfeld et al. eds., Alan R. Liss, Inc., N.Y. (1985); Hellstrom et al., in Controlled Drug Delivery, 2nd ed., pp. 623-653, Robinson et al., eds., Marcel Dekker, Inc., New York (1987); Thorpe, in Monoclonal Antibodies '84: Biological And Clinical Applications, Pinchera et al., eds., Editrice Kurtis, s.r.l., Milan, pp. 475-506, (1985); Monoclonal Antibodies For Cancer Detection and Therapy, Baldwin et al., eds., Academic Press, Inc. (1985); and Thorpe et al. (1982), *Immunol. Rev.*, 62:119-158. Alternatively, an antibody can be conjugated to a second antibody to form an antibody heteroconjugate, such as a bifunctional antibody, see, e.g., U.S. Pat. No. 4,676,980.

The conjugates of this invention can be used for modifying a given biological response, in which the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *Pseudomonas* exotoxin or *Diphtheria* toxin; a protein such as tumor necrosis factor, $\alpha$-interferon, $\beta$-interferon, nerve growth factor, platelet derived growth factor, tissue plasminogen activator, an apoptotic agent, e.g., TNF-$\alpha$, TNF-$\beta$, AIM I (WO 97/33899), AIM II (WO 97/34911), Fas ligand (Takahashi et al. (1994), *Int. Immunol.*, 6:1567-1574), VEGF (WO 99/23105); a thrombotic agent; an anti-angiogenic agent, e.g., angiostatin or endostatin; or biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (GCSF) or other growth factors.

The antibody or variant composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody or variant to be administered will be governed by such considerations, and can be the minimum amount necessary to prevent, ameliorate or treat a disease, condition or disorder caused by or associated with extended Type I chain antigen, in particular extended Type I chain glycosphingolipid.

As used herein, the term "effective amount" refers to the amount of a therapy (e.g., a prophylactic or therapeutic agent), which is sufficient to reduce the severity and/or duration of an extended Type I chain antigen related or associated disease, ameliorate one or more symptoms thereof, prevent the advancement of an extended Type I chain antigen related or associated disease, or cause regression of an extended Type I chain antigen related or associated disease, or which is sufficient to result in the prevention of the development, recurrence, onset, or progression of an extended Type I chain antigen related or associated disease or one or more symptoms thereof, or enhance or improve the prophylactic and/or therapeutic effect(s) of another therapy (e.g., another therapeutic agent) useful for treating an extended Type I chain antigen related or associated disease. For example, a treatment of interest can reduce a symptom, based on baseline or a normal level, by at least about 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In one other embodiment, an effective amount of a therapeutic or a prophylactic agent reduces a symptom of an extended Type I chain antigen related or associated disease, such as a cancer, by at least about 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Also used herein as an equivalent is the term "therapeutically effective amount."

The amount of therapeutic polypeptide, antibody or fragment thereof which will be effective in the use or treatment of a particular disorder or condition will depend on the nature of the disorder or condition, and can be determined by standard clinical techniques. Where possible, a dose-response curve of the pharmaceutical composition of this invention can be first derived in vitro. If a suitable animal model system is available, again a dose-response curve can be obtained and used to extrapolate a suitable human dose by practicing methods known in the art. However, based on common knowledge of the art, a pharmaceutical composition effective in promoting a diminution of an inflammatory effect, for example, may provide a local therapeutic agent concentration of between about 5 and about 20 ng/mL, and, preferably, between about 10 and about 20 ng/mL.

In a preferred embodiment, an aqueous solution of therapeutic polypeptide, antibody or fragment thereof can be administered by subcutaneous injection. Each dose may range from about 0.5 mg to about 50 mg per kilogram of body weight, or more preferably, from about 3 mg to about 30 mg per kilogram body weight. The dosage can be ascertained empirically for the particular disease, patient population, mode of administration and so on, by practicing pharmaceutical methods known in the art.

The dosing schedule for subcutaneous administration may vary from once a week to daily to multiple times a day depending on a number of clinical factors, including the type of disease, severity of disease and the sensitivity of the subject to the therapeutic agent.

In one embodiment, the composition is formulated in accordance with routine procedures as a pharmaceutical composition adapted for intravenous administration to humans. Typically, compositions for intravenous administration are solutions in sterile isotonic aqueous buffer. Where necessary, the composition may also include a solubilizing agent and a local anesthetic such as lidocaine or other "caine" anesthetic to ease pain at the site of the injection. Generally, the ingredients are supplied either separately or mixed together in unit dosage form, for example, as a dry lyophilized powder or a concentrate in a sealed container, such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided, for example, in a kit, so that the ingredients may be mixed prior to administration.

This invention also provides that a liquid formulation of the present invention is packaged in a sealed container such as an ampule or sachet indicating the quantity of the product of interest. The liquid formulations of the instant invention can be in a sealed container indicating the quantity and concentration of the antibody or antibody fragment. The liquid formulation of this invention can be supplied in a sealed container with at least about 15 mg/mL, 20 mg/mL, 30 mg/mL, 40 mg/mL, 50 mg/mL, 60 mg/mL, 70 mg/mL, 80 mg/mL, 90 mg/ml, 100 mg/mL, 150 mg/mL, 200 mg/mL, 250 mg/mL, or 300 mg/mL of an antibody against extended Type I chain antigen, in particular extended Type I chain glycosphingolipid, in a quantity of about 1 mL, 2 mL, 3 mL, 4 mL, 5 mL, 6 mL, 7 mL, 8 mL, 9 mL, 10 mL, 15 mL or 20 mL, for example.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for diagnosing, preventing or treating a condition or disease related to or associated with extended Type I chain antigen, in particular extended Type I chain glycosphingolipid, and may have a sterile access port (for example, the container may be an intravenous solution bag or a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

In another aspect of this invention, nucleic acids comprising sequences encoding antibodies or functional derivatives thereof, are administered to treat, inhibit or prevent a disease or disorder associated with aberrant expression and/or activity of extended Type I chain antigen, in particular extended Type I chain glycosphingolipid, by way of gene therapy. Gene therapy refers to therapy performed by the administration to a subject of an expressed or expressible nucleic acid of interest. Alternatively, cells manipulated to carry gene sequences of interest are administered to a host. In an embodiment of the invention, the nucleic acids produce the encoded protein in and by target host cells that mediate a therapeutic effect. Any of the methods for gene therapy available can be used according to the instant invention.

For general reviews of the methods of gene therapy, see Goldspiel et al. (1993), *Clinical Pharmacy,* 12:488-505; Wu et al. (1991), *Biotherapy,* 3:87-95; Tolstoshev (1993), *Ann. Rev. Pharmacol. Toxicol.,* 32:573-596; Mulligan (1993), *Science,* 260:926-932; Morgan et al. (1993), *Ann. Rev. Biochem.,* 62:191-217; and May (1993), *TIBTECH,* 11:155-215.

In one aspect, the compound comprises nucleic acid sequences encoding an antibody, or functional binding fragments thereof, said nucleic acid sequences being part of expression vectors that express the antibody or fragments or chimeric proteins or heavy or light chains thereof in a suitable host. In particular, such nucleic acid sequences have promoters operably linked to the antibody or antigen-binding coding region, said promoter being inducible or constitutive, and, optionally, tissue-specific, as well as other regulatory sequences.

In another particular embodiment, nucleic acid molecules are used in which the antibody coding sequences and any other desired sequences are flanked by regions that promote homologous recombination at a desired site in the genome, thus providing for integration and intrachromosomal expression of the antibody encoding sequences (Koller et al. (1989), *Proc. Natl. Acad. Sci. USA,* 86:8932-8935; Zijlstra et al. (1989), *Nature,* 342:435-438). In specific embodiments, the expressed antibody molecule is a single chain antibody; alternatively, the nucleic acid sequences include sequences encoding both the heavy and light chains, or fragments thereof, of the antibody. Alternative methods for integration include using particular transcription factors that recognize specific nucleic acid sequences, zinc fingers and so on.

Delivery of the nucleic acids into a patient may be either direct, in which case the patient is directly exposed to the nucleic acid or nucleic acid-carrying vectors, or indirectly, in which case, cells are first transformed with the nucleic acids in vitro, then transplanted into the patient.

In one embodiment, the nucleic acid sequences are directly administered in vivo and are expressed to produce the encoded product. That can be accomplished by any of numerous methods known in the art, e.g., by constructing the antibody encoding sequences as part of an appropriate nucleic acid expression vector and administering same so that the vectors become intracellular, e.g., by infection using defective or attenuated retroviral or other viral vectors (see U.S. Pat. No. 4,980,286), by direct injection of naked DNA, by use of microparticle bombardment (e.g., a gene gun; Biolistic, Dupont), using non-viral vectors, such as synthetic compositions comprising an amphipathic compound that binds the hydrophilic nucleic acid and has the ability to fuse with cells, generally thus containing a hydrophobic portion for combining with membranes, coating with lipids or cell-surface receptors or transfecting agents, encapsulation in liposomes, microparticles, or microcapsules, by administering the vector in linkage with a peptide which is known to enter the nucleus, by administering the vector in linkage with a ligand subject to receptor-mediated endocytosis (see, e.g., Wu et al. (1987), J. Biol. Chem., 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell-specific uptake and expression, by targeting a specific receptor (see, e.g., WO 92/06180; WO 92/22635; WO92/20316; WO93/14188 and WO 93/20221).

Regarding vectors, for example, a lentiviral vector can be used as known in the art. The lentiviral vectors contain components for packaging the viral genome and integration into the host cell DNA. The nucleic acid sequences encoding the antibody to be used in gene therapy are cloned into one or more vectors, which facilitate the delivery of the gene into a patient. For example, a lentiviral vector can be used to deliver a transgene to hematopoietic stem cells. References illustrating the use of retroviral vectors in gene therapy are: Clowes et al. (1994), *J. Clin. Invest.*, 93:644-651; Kiem et al. (1994), *Blood,* 83:1467-1473; Salmons et al. (1993), Human Gene Therapy, 4:129-141; and Grossman et al. (1993), *Curr. Opin. Gen. Dev.,* 3:110-114.

Adenoviruses also may be used in this invention. Targets for adenovirus-based delivery systems include liver, the central nervous system, endothelial cells and muscle, for example. Adenoviruses infect non-dividing cells, an advantage over early retroviral vectors. In *Curr. Opin. Gen. Dev.,* 3:499-503 (1993), Kozarsky et al. presented a review of adenovirus-based gene therapy. In *Human Gene Therapy,* 5:3-10 (1994), Bout et al. demonstrated the use of adenovirus vectors to transfer genes to the respiratory epithelia of rhesus monkeys. Other instances of the use of adenoviruses in gene therapy can be found in Rosenfeld et al. (1991), *Science,* 252:431-434; Rosenfeld et al. (1992), *Cell,* 68:143-155; Mastrangeli et al. (1993), *J. Clin. Invest.,* 91:225-234; WO94/12649; and Wang et al. (1995), *Gene Therapy,* 2:775-783.

Adeno-associated virus (AAV) also can be used in gene therapy (Walsh et al. (1993), *Proc. Soc. Exp. Biol. Med.,* 204:289-300; and U.S. Pat. Nos. 5,436,146, 6,632,670 and 6,642,051).

Another approach to gene therapy involves transferring a gene to cells in tissue culture by methods such as electroporation, lipofection, calcium phosphate mediated transfection or viral infection. Usually, the method of transfer includes the transfer of a selectable marker into the cells. The cells then are placed under selection to isolate those cells that have taken up and are expressing the transferred gene. Those cells then are delivered to a patient.

Thus, the nucleic acid can be introduced into a cell prior to administration in vivo of the resulting recombinant cell. Such introduction can be carried out by any method known in the art, including, but not limited to, transfection, electroporation, microinjection or infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler et al. (1993), Meth. Enzymol., 217:599-618; Cohen et al. (1993), *Meth. Enzymol.,* 217:618-644; and Cline (1985), *Pharm. Ther.,* 29:69-92) and may be used in accordance with this invention, provided that the necessary developmental and physiological functions of the recipient cells are not disrupted. The technique should provide stable transfer of the nucleic acid into the cell, so that the nucleic acid is expressed by the cell, heritable and expressed by the cell progeny.

The resulting recombinant cells can be delivered to a patient by various methods known in the art. Recombinant blood cells (e.g., hematopoietic stem or progenitor cells) are preferably administered intravenously, for example, as known in the bone marrow transplantation art. The amount of cells envisioned for use depends on the desired effect, patient state, etc., and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes, blood cells, such as T lymphocytes, B lymphocytes, monocytes, macrophages, neutrophils, eosinophils, megakaryocytes and granulocytes, various stem or progenitor cells, in particular hematopoietic stem or progenitor cells, e.g., as obtained from bone marrow, umbilical cord blood, peripheral blood, fetal liver, etc.

In one embodiment, the cell used for gene therapy is autologous to the patient. Nucleic acid sequences encoding an antibody of this invention are introduced into the cells such that the transgene is expressed by the cells or their progeny, and the recombinant cells then are administered in vivo for therapeutic effect. In a specific embodiment, stem or progenitor cells are used. Any stem and/or progenitor cells which can be isolated and maintained in vitro can potentially be used in accordance with the embodiment of this invention (see e.g., WO 94/08598; Stemple et al. (1992), *Cell,* 71:973-985; Rheinwald (1980), *Meth. Cell. Bio.,* 21A:229; and Pittelkow et al. (1986), *Mayo. Clinic Proc.,* 61:771-777). Because extended Type I chain antigen is expressed on, for example, B cells, blood cells and bone marrow cells are suitable host cells. However, the scope of this invention regarding the use of stem cell hosts does not contemplate the making and using of a transgene to make a transgenic organism by administering the transgene of interest to embryos and/or embryonic stem cells.

This invention thus provides methods of treatment, prophylaxis and amelioration of extended Type I chain antigen related or associated diseases, or one or more symptoms thereof, by administering to a subject an effective amount of, for example, a liquid formulation containing an antibody or variant thereof of this invention. The subject is preferably a mammal such as non-primate (e.g., cows, pigs, horses, cats, dogs, rats, etc.) and a primate (e.g., monkey, such as a cynomolgus monkey, and a human). In a preferred embodiment, the subject is a human.

Extended Type I chain antigen also is expressed on certain cancer cells, such as pancreas, colon and bladder cancer cells, as well as on T cell leukemias, and stimulation of extended Type I glycosphingolipid correlated with proliferation of carcinoma cells.

Thus, the antibody or derivative thereof of interest can be used to control proliferation of cancer cells expressing extended Type I chain antigen, in particular extended Type I chain glycosphingolipid, which cancer cells are identified by determining presence of extended Type I chain antigen expression by a diagnostic assay taught herein. The antibody of interest can reduce infiltration of malignant cells, reduce resistance to apoptosis and minimize proliferation. Such patients then are administered a cancer cell proliferation inhibiting amount of an antibody, or derivative thereof, of interest as provided herein. As taught herein, an antibody or antigen-binding portion thereof can be administered to a patient in a number of ways, including administering a polypeptide, a polynucleotide and so on. Essentially any cancer that expresses an epitope comprising an extended Type I chain of interest can be detected and/or treated with an antibody of interest. For example, the malignant cell can be an epithelial cell. The epithelial cell can be found in any malignant cell of any organ or tissue origin, such as, colon, rectum, esophagus, lung, prostate, breast, pancreas, the oral cavity, vagina, the gastrointestinal tract in general, urinary tract and so on. However, the cancer need not be limited to an epithelial cell, so long as the malignant cell expresses an epitope comprising an extended Type I chain of interest.

In addition to mAb GNX-8, the applicants obtained a second monoclonal antibody GNX-10, which was found to have heavy chain and light chain variable regions structurally similar to those of mAb GNX-8. According to the alignment information of the amino acid sequences of the heavy and light chain variable regions of mAbs GNX-8 and GNX-10, 9 amino acid differences are present in the heavy chain variable region and 2 amino acid differences in the light chain variable region. There are 4 amino acid differences located in predicted CDR regions of the heavy chain variable region and only one amino acid difference in predicted CDR regions of the light chain variable region. MAb GNX-10 was further found to exhibit binding specificity characteristics closely similar to those of mAb GNX-8. Both of mAb GNX-8 and mAb GNX-10 specifically bind to an epitope comprising an extended Type I chain comprising Le$^b$, in particular an epitope comprising an extended Type I chain Le$^b$-Le$^a$.

Since the sequences of mAb GNX-8 and mAb GNX-10 are very similar, hybrid antibodies having similar binding specificity could be generated by cross-matching the heavy chain and light chain variable regions of mAb GNX-8 and mAb GNX-10. In this aspect, the applicants generated 2 cross-matched antibodies, i.e., hybrid antibody "GNX8H/GNX10L" constituted of GNX-8 heavy chain and GNX-10 light chain, and hybrid antibody "GNX10H/GNX8L" constituted of GNX-10 heavy chain and GNX-8 light chain. These two hybrid antibodies were to exhibit binding specificity substantially to that of mAbs GNX-8 and GNX-10.

Accordingly, this invention provides a binding moiety which specifically binds to an epitope comprising an extended Type I chain comprising Le$^b$, wherein the binding moiety comprises:

(a) a heavy chain variable region (V$_H$) that includes:

(i) a V$_H$ CDR1 sequence: Gly-Asp-Ser-Val-Ser-Ser-X$_1$-X$_2$-Val-Ala wherein X$_1$ is selected from the group consisting of Asn and Lys, and X$_2$ is selected from the group consisting of Thr and Ser;

(ii) a V$_H$ CDR2 sequence: Thr-Tyr-Tyr-Arg-Ser-Lys-Trp-Tyr-Asn; and (iii) a V$_H$ CDR3 sequence: Ala-Arg-Asn-Phe-Asp-X$_3$, wherein X$_3$ is selected from the group consisting of Ser and Tyr; and (b) a light chain variable region (V$_L$) that includes:

(i) a V$_L$ CDR1 sequence: Thr-Gly-Ala-Val-Thr-Thr-X$_4$-Asn-Tyr wherein X$_4$ is selected from the group consisting of Asp and Asn;

(ii) a V$_L$ CDR2 sequence: Ala-Thr-Ser; and (iii) a V$_L$ CDR3 sequence: Ala-Leu-Trp-Tyr-Asn-Thr-His-Phe-Val.

As used herein, the term "binding moiety" refers to any molecule or part of a molecule that can specifically bind to a target molecule or target epitope.

The term "specifically bind" means a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

In a preferred embodiment, the binding moiety of this invention binds to an epitope comprising an extended Type I chain Le$^b$-Le$^a$.

The epitope comprising an extended Type I chain Le$^b$-Le$^a$ may be expressed on a cancer cell, which may be an epithelial cell, and may be found on glycosphigolipids, glycoproteins and glycans present on or isolated from cancer cells expressing the same. The cancer cell may be cancer cells of primary and metastatic colorectal cancers, breast cancers, pancreas cancers, lung cancers, stomach cancers, esophagus cancers, prostate cancers, etc.

The binding moiety according to this invention may be selected from:

(a) antibodies or antigen-binding fragments thereof;

(b) antibody-like proteins; and (c) peptidomimetics.

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz H. K. et al. (2005), *Nat. Biotechnol.*, 23(10):1257-1268). Antibody-like proteins can be derived from large libraries of mutants, e.g., be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers."

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of non-natural amino acids).

In preferred embodiments of this invention, the binding moiety is an antibody or an antigen-binding fragment thereof, said antibody being selected from the group consisting of polyclonal antibodies, monoclonal antibodies, monovalent antibodies, bispecific antibodies, heteroconjugate antibodies, multispecific antibodies, deimmunized antibodies, chimeric antibodies, humanized (in particular CDR-grafted) antibodies, and human antibodies.

In preferred embodiments of this invention, the binding moiety is an antigen-binding fragment of an antibody, said fragment being selected from the group consisting of Fab fragments, Fab' fragments, F(ab')$_2$ fragments, Fv fragments, disulfide-linked Fvs (dsFv), single domain antibodies (also known as nanobodies), and single chain Fv (scFv) molecules.

More detailed definitions in connection with the terms "antibodies or antigen-binding fragments thereof," "antibody-like proteins" and "peptidomimetics," etc., can be found in, e.g., WO 2011/063980 A1.

In a preferred embodiment of this invention, the binding moiety comprises a V$_H$ CDR1 sequence of SEQ ID NO:31, a V$_H$ CDR2 sequence of SEQ ID NO:32, a V$_H$ CDR3 sequence of SEQ ID NO:33, a V$_L$ CDR1 sequence of SEQ ID NO:35, a V$_L$ CDR2 sequence of SEQ ID NO:36, and a V$_L$ CDR3 sequence of SEQ ID NO:37.

In another preferred embodiment of this invention, the binding moiety comprises a V$_H$ CDR1 sequence of SEQ ID NO:18, a V$_H$ CDR2 sequence of SEQ ID NO:20, a V$_H$ CDR3 sequence of SEQ ID NO:22, a V$_L$ CDR1 sequence of SEQ ID NO:35, a V$_L$ CDR2 sequence of SEQ ID NO:36, and a V$_L$ CDR3 sequence of SEQ ID NO:37.

In yet another preferred embodiment of this invention, the binding moiety comprises a $V_H$ CDR1 sequence of SEQ ID NO:31, a $V_H$ CDR2 sequence of SEQ ID NO:32, a $V_H$ CDR3 sequence of SEQ ID NO:33, a $V_L$ CDR1 sequence of SEQ ID NO:24, a $V_L$ CDR2 sequence of SEQ ID NO:26, and a $V_L$ CDR3 sequence of SEQ ID NO:28.

In yet another preferred embodiment of this invention, the binding moiety comprises a heavy chain variable region of SEQ ID NO:30 and a light chain variable region of SEQ ID NO:34.

In yet another preferred embodiment of this invention, the binding moiety comprises a heavy chain variable region of SEQ ID NO:15 and a light chain variable region of SEQ ID NO:34.

In yet another preferred embodiment of this invention, the binding moiety comprises a heavy chain variable region of SEQ ID NO:30 and a light chain variable region of SEQ ID NO:17.

In a preferred embodiment of this invention, the binding moiety is an antibody comprising a κ chain.

In another preferred embodiment of this invention, the binding moiety is an antibody comprising a γ chain.

In a preferred embodiment of this invention, the binding moiety is a scFv.

The binding moiety of this invention, as well as nucleic acid sequence encoding the same, may be synthesized via chemical or recombinant methodologies commonly employed by those with ordinary skill in the art, e.g., those approaches described above. For example, the binding moiety of this invention may be produced using one or more of the following methods: hybridoma technique, recombinant DNA technology, chemical synthesis, and enzymatic synthesis.

The binding moiety of this invention may be used as a therapeutic or diagnostic agent, and compositions and/or articles comprising the same for these purposes may be formulated by methodologies commonly employed by those with ordinary skill in the art, e.g., those approaches described above.

This invention now will be exemplified for the benefit of the artisan by the following non-limiting examples that depict some of the embodiments by and in which the instant invention can be practiced.

EXAMPLES

Example 1

Generation of Immunogen

Colorectal adenocarcinoma cells Colo205 (ATCC CCL-222) and DLD-1 (ATCC CCL-221) were cultured in RPMI-1640 medium (Invitrogen Co., Cat. No. 31800) supplemented with 1 mM sodium pyruvate (Invitrogen Co., Cat. No. 11360). Other two colorectal adenocarcinoma cell lines, i.e., SW1116 (ATCC CCL-233) and HT-29 (ATCC HTB-38), and the lung-derived T84 cell line (ATCC, CCL-248) were maintained in Leibovitz's L-15 medium (Invitrogen Co., Cat. No. 41300), McCoy's 5a medium (Invitrogen Co., Cat. No. 12330) and DMEM/F12 medium (Invitrogen Co., Cat. No. 12400), respectively. The KATO III gastric carcinoma cell line (ATCC HTB-103) was cultured in IMDM medium (Invitrogen Co., Cat. No. 12200). All culture media used in the studies of this invention were supplemented with 10% fetal calf serum.

Colo205 cells (Semple et al. (1978), *Cancer Res.*, 38:1345-1355) were grown in RPMI-1640 medium supplemented with 10% fetal calf serum. Thereafter, the cultured cells were harvested and washed twice with PBS and stored at −20° C. until use. Cell pellets of Colo205 cells were extracted with isopropanol-hexane-water (IHW, 55:25:20), followed by Folch partition, DEAE Sephadex chromatography and HPLC on an Iatrobead 6RS-8010 column (Iatron Corp., Tokyo). Gradient elution of the upper-phase neutral fraction was performed in IHW from 55:40:5 to 55:25:20 over 200 minutes. Fractions were collected and pooled according to HPTLC migration in chloroform-methanol-water (50:40:10). The extended Type I chain glycosphingolipids were further purified by preparative TLC on Merck HPTLC plates (Silica Gel 60, Merck, Darmstadt, Germany), see U.S. Pat. No. 6,083,929.

A positive band (by immunostaining with mAb IMH2) which migrated just below dimeric Le$^a$ antigen was purified as taught herein. MAb IMH2 recognizes an epitope comprising extended Type I chain Le$^b$-Le$^a$ (Mark R. Stroud et al. (1992), *Eur. J. Biochem.*, 203:577-586; Hisashi Ito et al. (1992), *Cancer Research*, 52:3739-3745).

Example 2

Generation of Anti-Extended Type I Chain Glycosphingolipid mABs

KM mice (Kirin Brewery Co., Ltd.) were generated by cross breeding double transchromosomic mice and transgenic mice. KM mice possess human chromosome fragments containing the entire human immunoglobulin heavy chain loci and a YAC transgene for half of the human immunoglobulin kappa light chain loci. KM mice were engineered to express neither endogenous immunoglobulin heavy chain nor kappa light chain. In the studies of this invention, all of the animals were maintained and handled according to the rules and regulations accepted in the art.

Colo205 cells were injected intraperitoneally into KM mice every 3 weeks (5×10$^6$ cells/injection) for a total of 4 injections, followed by injection of extended Type I chain glycosphingolipids which were isolated from Colo205 cells and adsorbed on lipopolysaccharide (Sigma, L-7011) (Young et al. (1979*J. Exp. Med.*, 150:1008-1019) every week for 8 injections. The anti-Colo205 neutral glycosphingolipid titers of immunized mice were monitored by ELISA, using anti-human kappa-HRP (Southern Biotechnology Associates, Cat. No. 9220-05) as the secondary antibody until the titer reached 1:6000.

Three days after the final injection, splenocytes from the boosted mouse were fused with P3/NS1/1-Ag4-1 (NS-1) mouse myeloma cells (ATCC TIB-18) by practicing methods known in the art. Hybridomas were screened by ELISA using 96-well ELISA plates (Corstar, Cat. No. 2592) coated with Colo205 neutral glycolipids. Mouse anti-human IgG antibodies conjugated with HRP were used as the secondary antibody (Southern Biotechnology Associates, Cat. No. 9040-05) and 3,3',5,5'-tetramethylbenzidine (TMB)(Kem-Zn-Tec Diagnostics, Cat. No. 4390) was used as the substrate.

Hybridoma supernatants showing high immunoreactivity with Colo205 neutral glycolipids were further confirmed by HPTLC immunostaining and by flow cytometry. Clones showing strong immunoreactility to the extended Type I chain glycosphigolipids and high binding on the cell surfaces of Colo205 cells were repeatedly sub-cloned by limiting dilution until stable clones are established. One stable clone thus obtained is GNX-8.

Hybridoma clone GNX-8 has been deposited in accordance with the terms of the Budapest Treaty at the Deutsche Sammlung von Mikroorganismen and Zellkulturen GmbH (DSMZ) under the accession number DSM ACC2878.

Example 3

GNX-8 Antibody

Monoclonal antibodies (mAbs) produced by the hybridoma clone GNX-8 obtained in Example 2 were purified from culture supernatants using protein A Sepharose (GE Healthcare 17-129-79-02) with pH gradient elution according to the manufacturer's suggested procedures. Each fraction was collected and the presence of antibody was examined by ELISA. Fractions with Colo205 neutral glycolipid binding activity were pooled and dialyzed against PBS (pH 7.4). Purified antibodies were aliquoted and stored at −20° C.

The concentration of monoclonal antibody was determined with the Bio Rad Protein Assay kit (Bio-Rad, Cat. No. 500-0006) using IgG as the standard according to the manufacturer's recommended procedures.

The isotype of mAb GNX-8 was determined using an ELISA. MAb GNX-8 is a human IgG[1] whose chain is kappa.

Purified mAb GNX-8 was applied to 10% SDS-polyacrylamide gels after being boiled in 2×SDS gel-loading buffer with (reducing condition) or without (non-reducing condition) β-mercaptoethanol. Electrophoresis was conducted using the Electrophoresis System (BIO-RAD) according to the manufacturer's recommendations.

MAb GNX-8 separated on reducing SDS-PAGE gels was transferred onto nitrocellulose (NC) membranes (Amersham), which were subsequently blocked with 3% skim milk in PBS. The membranes were then incubated with secondary antibody for 1 hour at room temperature. HRP-labeled goat anti-human IgG(γ) antibody (Zymed, 62-8420) at 1:5000 dilution and HRP-labeled rabbit anti-human kappa chain IgG antibody (DAKO, P0129) at 1:2000 dilution were separately used to detect the heavy chain and light chain of mAb GNX-8. Western Lightning™ Chemiluminescence Reagent Plus (PerkinElmer Life Sciences, Cat. No. NEL105) was used to develop the signal on BioMax Light Film (KODAK, Cat. No. 1788207).

Under reducing conditions, the molecular weight of the mAb GNX-8 light chain and heavy chain are as expected for an IgG. MAb GNX-8 is a human monoclonal antibody as examined by Western blotting using goat anti-human IgG(γ)-HRP and rabbit anti-human kappa chain-HRP as secondary antibodies, separately. GNX-8 is a human $IgG_1$ antibody as examined by ELISA isotyping.

The pI analysis of mAb GNX-8 was determined by the PhastSystem (Pharmacia). Briefly, an antibody sample and pI standard were applied on an IEF PhastGel 3-9 using a PhastGel Sample applicator 8/1 comb and were separated according to the manufacturer's protocol. The gel subsequently was silver-stained in the PhastSystem Development Unit (Pharmacia) according to the manufacturer's protocol.

The pI analysis reveals multiple bands ranging from pH 8.15 to 8.65, indicating the possibility of post-translational modifications of the antibody. The high pI indicates that mAb GNX-8 will be soluble at physiologic pH.

For detecting cell binding activity, $2 \times 10^5$ cells of a test cell line were washed with PBS and incubated with various concentrations of mAb GNX-8 for 30 minutes at room temperature. After a PBS wash, FITC-labeled goat anti-human IgG (Fc) antibodies at 1:3000 dilution (ICN, Cat no. 55198) were added to each cell sample for an additional 30 minutes at room temperature. After a final PBS washing, cells were analyzed on a flow cytometer (BD, FACSort). The results were processed with CELLQuest 3.3 (BD, FACSort).

Example 4

Cytotixicity Assay

Human colon cancer cell lines, SW1116, Colo205 and DLD-1, were seeded in 48-well plates (Corning Costar) at a density of $2 \times 10^4$ cells/well. After being cultured overnight, the cells are incubated in 500 μL of medium supplemented with 25% non-inactivated human serum at various antibody concentrations for 2 hr. After a PBS wash, the remaining live cells were quantified by propidium iodide (PI) solution (Sigma-Aldrich, P4846) staining and were analyzed by flow cytometry. Cells treated with normal human IgGs purified from normal human serum served as a negative control.

In an alternative assay, target cells were labeled by incubation with about 100 μL of $^{51}Cr$ for about 90 min. at about 37° C. After washing (3×) and incubation (about 1 hr at 37° C., cells (about $1 \times 10^6$ mL) were suspended in RPMI-1640 supplemented with about 25 mM HEPES buffer and about 3% bovine serum albumin. About 20 μL of labeled cells, about 100 μL of mAb and 25% heat inactivated human serum are mixed in the wells of microtiter U bottom plates (Corning, N.Y.). Non-specific mouse Ig (Sigma, St. Louis, Mo.) could be used as a negative control. After about 4 hr incubation, the plates are centrifuged (500×g, 2 min) with a hanging plate holder assembled in a centrifuge, and radioactivity in about 100 μL supernatant in each well was measured with a gamma counter. Each experimental group could be tested in triplicate. Percent specific lysis could be calculated according to the formula ([A−B]×100)/C, where A=cpm in lysed experimental cells; B=cpm in unlysed target cells; and C=cpm in total target cells. Spontaneous release preferably should not exceed 15% of maximally releasable labeled radioactivity.

ADCC assays were performed by the lactate dehydrogenase (LDH) release assay (Promega, CytoTox 96® Non-Radioactive Cytotoxicity Assay) using human peripheral blood mononuclear cells (PBMC), which were prepared from healthy donors using Ficoll-Paque (GE, 71-7167-00), as effector cells. This assay quantitatively measures lactate dehydrogenase (LDH), a stable cytosolic enzyme that is released on cell lysis. Released LDH in culture supernatants is measured with a 30 minute coupled enzymatic assay, which results in the conversion of a tetrazolium salt (INT) into a red formazan product. The amount of color formed was proportional to the number of lysed cells.

Colo205 cells used as target cells were distributed into 96-well U bottom plates ($2 \times 10^4$ cells/well) and were incubated with antibodies in the presence of the PBMC with various E/T ratios for 4 hours at 37° C. The LDH activity in the supernatant was measured by CytoTox 96® Non-Radioactive Cytotoxicity Assay. The percent specific cytolysis was calculated according to the following formula: % specific lysis=$100 \times (E-S_E-S_T)/(M-S_T)$ where E is the experimental release (activity in the supernatant from target cells incubated with antibody and effector cells), $S_E$ is the spontaneous release in the presence of effector cells (activity in the supernatant from effector cells with medium alone), $S_T$ is the spontaneous release of target cells (activity in the supernatant from target cells incubated with medium alone), and M is the maximum release of target cells (activity released from target cells lysed with 9% Triton X-100).

The in vitro antitumor activity of mAb GNX-8 was evaluated by CDC assay. Treatment of human colorectal cancer cell lines, SW1116, Colo205 and DLD-1, with mAb GNX-8 in the presence of 25% human serum, resulted in substantial cell lysis in a dose dependent manner. The results indicate that mAb GNX-8 kills target cells through complement-dependent cytolysis.

The CDC effect of mAb GNX-8 on SW1116 and Colo205 cells in some experiments is stronger than that on DLD-1 cells. The viability of cells is inversely proportional proportion to the level of expression of GNX-8 antigen. The CDC effect of mAb GNX-8 and the levels of GNX-8 antigen expression on the three colorectal cancer cell lines demonstrate that cancer cells with higher GNX-8 antigen expression are more susceptible to cytotoxicity while those with lower GNX-8 antigen expression have higher viability. The results lead to the conclusion that the antitumor activity of mAb GNX-8 can depend on the expression level of GNX-8 antigen. Patients with high GNX-8 antigen expression on tumor cells might be treated with mAb GNX-8 alone, while tumors expressing lower levels of GNX-8 antigen may benefit from a combination therapy using one or more other cancer drugs in addition to mAb GNX-8.

ADCC activity of human peripheral blood mononuclear cells (PBMC) was evaluated against human colorectal cancer Colo205 in the presence of mAb GNX-8. Cells treated with IMH2 served as a positive control and cells treated with human IgG served as a negative control.

MAb GNX-8 induced strong ADCC activity against Colo205 cells. The cytotoxic effect was correlated positively with both E/T ratio and mAb GNX-8 concentration. One hundred percent cell lysis was observed at E/T of about 20/1. A maximal ADCC effect, and a trend observed for about 50% lysis as well, was observed at about 5 µg/mL for mAb GNX-8 and at about 50 µg/mL for IMH2, respectively. Control human IgG showed no cytotoxic effect regardless of E/T ratio or IgG concentration. The dose of mAb GNX-8 to reach 50% lysis was less than 1/10 needed for IMH2.

Example 5

BIAcore Affinity Analysis

Extended Type I chain glycosphingolipids were affixed to a chip. Then the mAbs were exposed to the chip for kinetic measurements and epitope sequence analysis surrounding the antibody-antigen binding reaction, following the manufacturer's recommendations (GE Healthcare, Pistcataway, N.J.).

Example 6

In Vivo Assay

Antitumor activity of mAb GNX-8 was evaluated in a Colo205 xenograft model. Colo205 cells are washed twice with PBS and reconstituted at a cell density of $5 \times 10^6/100$ µL in PBS. Female nude mice of age 6-8 weeks were inoculated s.c. with 100 µL of the Colo205 cell suspension in the flank region. Tumor sizes are measured three times a week with a vernier caliper and tumor weights (mg) are estimated as (width$_2$×length)/2. MAb GNX-8 or normal human IgG was i.p. injected in tumor-bearing nude mice according to designed doses and schedules.

To evaluate the in vivo antitumor efficacy of mAb GNX-8, cancer cells ($5 \times 10^6$ cells/mouse) were injected in nude mice and treated with either mAb GNX-8 (treatment group, 8 mice/group) or normal human IgG (control group, 7 mice/group) 24 hours after tumor inoculation. Five doses (300 µg/mouse) at 24-hour intervals and subsequently four doses (600 µg/mouse) at 48-hour intervals were injected in both groups.

Tumor growth was significantly inhibited in GNX-8-treated mice. The treatment group reached a median tumor weight of T/C (Treatment/Control) of about 23% on day 11 and continued at that approximate level to the end of the study. A T/C measure of ≤42% was considered significant in demonstrating antitumor activity.

Half (4/8) of the mice in the GNX-8 treatment group achieved long term tumor-free survival over 50 days. On the other hand, tumor size of the control group animals continually increased during the study.

A similar study was conducted in a Colo205 xenograft nude mice model. The first dose of mAb GNX-8 was given at a tumor size of 80 to 100 mg. MAb GNX-8 (treatment group) and normal human IgG (control group) were injected once (300 µg/mouse) daily for five days, and with two similar doses at days 17 and 21.

Significant tumor inhibition also was observed in the treatment group, although the treatments were discontinued after only 5 doses. The median tumor weight of T/C (Treatment/Control) was lower than 42% after day 10 and through to the end of the study.

To determine whether host effector function contributed to mAb GNX-8 efficacy, SCID mice bearing Colo205 xenografts were treated with mAb GNX-8 or normal human IgG at 600 µg/mouse twice weekly for three weeks. Tumor size was measured twice every week until the tumor size reached 10% of the body weight, which was considered the endpoint of the study.

Survivability was prolonged in the treatment group.

To explore the occurrence of the GNX-8 epitope on human colorectal cancer cells, several human colorectal cancer cell lines were analyzed.

For example, the in vivo inhibition of DLD-1 by mAb GNX-8 was significant.

Example 7

GNX-8 Antigen

For the analysis of cell glycoproteins, cultured cells were scraped from the T-75 flasks and washed twice with PBS, followed by lysis buffer (50 mM Tris-HCl pH 7.5, 150 mM NaCl, 1% NP-40, 0.5% sodium deoxycholate, 0.1% SDS and 1 mM PMSF). The lysates were passed through a 26 gauge needle several times to disperse any large aggregates. Protein concentration was determined by Protein Assay Kit (Bio-Rad). The lysates containing the same amount of proteins were separated on a gel and analyzed by Western blot with mAb GNX-8 as the primary antibody and mouse anti-human IgG (Fc) labeled with HRP (Southern Biotechnology Associates, #9040 05) as the secondary antibody. Western Lightning™ Chemiluminescence Reagent Plus (PerkinElmer Life Sciences, Cat. No. NEL105) was used to develop the signal on BioMax Light Film (KODAK, Cat. No. 1788207).

The results show the presence of GNX-8 antigen on glycoproteins of Colo205 and SW1116 over a molecular weight ranging from 32 to >175 kDa. Accordingly, GNX-8 antigens are not only in glycolipids but also in glycoproteins.

Colo205 neutral glycolipids (2 µL/sample) were spotted on a HPTLC plate (Merck, 1.05642, silica gel 60 F254), and developed with a mobile phase containing chloroform:methanol:water at a ratio of 50:40:10 (V:V:V). For glycan staining of glycolipids, 0.2% orcinol (Sigma, 0-1875) in 10% $H_2SO_4$ was sprayed onto a HPTLC plate and incubated for 10 minutes at 110° C. in an oven. For immunostaining, the HPTLC plate was first fixed with 0.5% poly(isobutyl methacrylate) (Aldrich, 181544) in chloroform:hexane (1:9, V:V) for 45 seconds, followed by blocking for 10 minutes in 3% BSA/PBS. The plates then were washed with PBS and incubated with the primary antibody at room temperature for 1 hr, followed by biotinylated secondary antibody (goat anti-human IgG) at room temperature for 1 hr. An Avidin-Biotin Complex kit (Vector Laboratories, Burlingame, Calif.) was used to amplify signals from the secondary antibody. The plates were incubated at room temperature for 30 minutes, followed by color development with an Immunostaining HRP-1000 kit (Konica Minolta, 130990) according to the manufacturer's protocol.

The neutral glycolipids of Colo205 were lyophilized and treated with hydrogen fluoride (HF) and then the mixture was incubated at 4° C. for 48 hours. At the end of the reaction, HF was removed with $N_2$ gas, and the resultant product was analyzed by MALDI-TOF MS to confirm the removal of fucose. The defucosylated glycolipids thus obtained were used for TLC immunostaining to analyze the binding specificity of GNX-8 to Colo205 neutral glycolipids before and after HF treatment.

MAb GNX-8 recognizes untreated Colo205 neutral glycolipids but not the defucosylated forms, suggesting that the epitope of mAb GNX-8 is a carbohydrate moiety and fucose is an essential component of the epitope's structure.

The binding specificity of mAb GNX-8 was characterized further by HPTLC immunostaining on neutral and monosialyl glycolipids isolated from Colo205 cells. One hundred grams of Colo205 cells were collected, and glycolipid fractions were extracted. Colo205 glycolipids separated by TLC were stained for carbohydrate with orcinal/$H_2SO_4$. The positions of $Le^a$, $Le^b$, $Le^a$-$Le^a$, and $Le^b$-$Le^a$ were identified according to Stroud et al. (1992), supra. Sialyl $Le^a$ ($SLe^a$) was indicated by staining with mAb NKH3 (U.S. Pat. No. 5,240,833) and was later identified with MALDI-MS. HPTLC immunostaining of the same glycolipid fractions were conducted with mAb CF4C4 (anti-Lea, U.S. Pat. No. 5,011,920), mAb T218 (anti-$Le^b$, Abcam, Cambridge, Mass.), mAb IMH2 (anti-$Le^b$-$Le^a$, Stroud et al., 1992, supra), and mAb GNX-8 of this invention.

The results indicate that mAb GNX-8 of this invention strongly reacts with extended Type I chain glycolipids. MAb GNX-8 did not bind to $Le^a$ extended Type I chains. The monosialyl glycolipids of Colo205 cells were not recognized by mAb GNX-8. MAb GNX-8 showed very slight cross-reactivity with $Le^b$ at higher concentration (0.6 μg/mL). Unlike mAb IMH2, mAb GNX-8 did not bind to $Le^x$ or to $Le^y$. MAb GNX-8 bound to an extended Type I chain containing $Le^b$. MAb GNX-8 binds to $Le^b$-$Le^a$.

In addition to TLC immunostaining, the epitope of mAb GNX-8 was characterized by competitive ELISA using synthetic glycans $Le^b$, $Le^a$-$Le^x$, $Le^b$-$Le^x$ and $Le^x$-$Le^x$ as inhibitors, and the $Le^b$-$Le^a$/$Le^a$-$Le^a$ glycolipid mixture as a positive control.

The results indicate that mAb GNX-8 of this invention slightly cross-reacts with $Le^b$-$Le^x$ at high inhibitor concentration, but has no reactivity with other tested synthetic glycans including synthetic $Le^b$ glycans. The binding activity of mAb GNX-8 to extended $Le^b$ was 1000 times higher than that to simple $Le^b$.

Based on the results, the epitope of mAb GNX-8 likely is a $Le^b$ structure on an extended Type I chain with fucosylation, but it is not a simple $Le^b$.

Example 8

Cell and Tissue Distribution

Formalin-fixed paraffin-embedded specimens of human normal and cancer tissues we obtained, for example, from US Biomax.

The formalin-fixed, paraffin-embedded tissue arrays of normal and malignant human tissues were blocked with 0.1% skim milk in PBS for 30 minutes. After an additional 10 minute incubation with 3% $H_2O_2$, the tissue arrays were washed thrice with PBS before samples were incubated with 0.1% BSA/PBS-diluted biotinylated GNX-8 for 1 hour. Then the tissue samples were reacted with biotin streptavidin-peroxidase complex (ABC kit, Vector, #PK-6100) for 30 minutes for signal amplification. The DAB PLUS Substrate Kit (Zymed #00 2020) was used to visualize immunoreactive staining according to the manufacturer's protocol. Counterstaining was performed using hematoxylin. The results were determined by visualization under a light microscope.

A variety of specimens from various organs, including both normal and cancer tissues, were separately stained with mAb GNX-8 Staining patterns in tissue specimens were evaluated by staining intensity and frequency of positive cells. Staining was graded on a scale of 1+ (10-20%), 2+ (20-50%) or 3+ (>50%), whereas frequency is classified based on the percentage of positive cells in each section.

The expression of GNX-8 antigen on human cancer cells was evaluated by flow cytometry. A number of human colorectal and gastric tumor cell lines, such as, Colo205, HT-29, DLD-1, SW1116, T84 and KATO III, were separately examined for the expression of GNX-8 antigen by flow cytometry.

Flow cytometric analyses demonstrate that mAb GNX-8 exhibits binding activity to all tested cancer cell lines. However, the binding is significantly stronger to SW1116, Colo205 and DLD-1 cells than to the other tested human cancer cell lines.

In addition, GNX-8 antigen expression was tested on HL60 (a human promyelocytic cell line), MCF-7 (a human breast cancer cell line) and PANC-1 (a human pancreas cancer cell line), as well as on a mouse colon cancer cell line, CT26. MAb GNX-8 does not bind to these four cell lines.

Two colorectal cancer cell lines, Colo205 and SW1116, were analyzed by Western blot. The two cell lines demonstrated strong binding with mAb GNX-8 in flow cytometry analyses.

A strong correlation was observed between primary and metastatic colorectal carcinomas in regard to GNX-8 antigen expression. An immunohistochemical staining of a panel of tissue sections from a colorectal cancer patient was conducted.

GNX-8 antigen was expressed not only on colorectal cancer tissues but also on adjacent tissues. For example, a polyp next to a cancer region was stained by mAb GNX-8. However, no staining was observed on distal normal tissues. Hence, it can be concluded mAb GNX-8 identifies transformed cells or cells undergoing transformation before recognizable cell morphology changes occur.

GNX-8 antigen expression was also studied on various grades of cancer.

GNX-8 antigen was expressed in each cancer stage.

GNX-8 did not bind to normal colon, rectum, stomach, small intestine, liver, esophagus, lung, prostate or breast.

Fifty-eight percent (44/76) of colon cancer samples were stained with mAb GNX-8, while 47% of rectum cancer samples, 57% of metastatic colon cancer samples, 53% of stomach cancer samples, 29% of esophageal cancer samples, 22% of lung cancer samples, 4% of prostate cancer samples, 17% of breast cancer samples and 67% of pancreatic cancer samples were stained with mAb GNX-8. MAb GNX-8 did not bind to small intestine, liver and kidney cancer samples.

TABLE 1

Binding specificity of GNX-8 on Human Normal Tissues
Normal Tissues

| Human tissues | Incidence (No. positive/No. tested) |
|---|---|
| Colon | 14/102 |
| Esophagus | 3/4* |
| Breast | 13/56§ |
| Pancreas | 4/12# |
| Kidney | 11/63# |
| Rectum | 1/106 |
| Small intestine | 0/2 |
| Liver | 0/4 |
| Lung | 0/3 |
| Prostate | 0/6 |

*Stained on keratinization of stratified squamous epithelium.
§Stained on epithelial cells of duct system/lactiferous ducts.
Stained on epithelial cells of duct system.

TABLE 2

Binding specificity of mAb GNX-8 on Human Cancer Tissues

| Human cancer tissues | Incidence (No. positive/No. tested) | Staining intensity |
|---|---|---|
| Colon | 44/76 | 3 + (5)*, 2 + (12), 1 + (27) |
| Rectum | 50/107 | 3 + (13), 2 + (20), 1 + (17) |
| Small intestine | 0/10 | |
| Liver | 0/12 | |
| Kidney | 0/3 | |
| Colon (metastatic) | 27/47 | 2 + (9), 1 + (18) |
| Esophagus | 4/14 | 2 + (1), 1 + (3) |
| Lung | 10/45 | 3 + (1), 2 + (5), 1 + (4) |
| Prostate | 2/45 | 2 + (2) |
| Breast | 7/45 | 3 + (1), 2 + (4), 1 + (2) |
| Pancreas | 8/12 | 2 + (3), 1 + (5) |

*Number of samples exhibiting the indicated staining intensity.

Example 9

Cloning and Sequencing of cDNA Encoding mAb GNX-8

GNX-8-producing hybridoma cells were routinely cultured in IMDM (Invitrogen) containing 10% low IgG fetal bovine serum (HyClone). To prepare RNA for cDNA synthesis, $1\times10^6$ hybridoma cells were first harvested by low speed centrifugation (1,000 rpm, 5 min). Total RNA then was isolated from the cell pellet using TRIZOL reagent (Invitrogen) according to the manufacturer's protocol. First strand cDNAs were synthesized from the purified RNA sample using the SMART RACE cDNA Amplification Kit (BD Biosciences-Clontech). Briefly, 1 μg total RNA was incubated with 1 μL 5'-CDS and 1 μL SMART II A oligo primers at 70° C. for 2 minutes. After addition of 2 μL 5× first-strand buffer, 1 μL 20 mM DTT, 1 μL 10 mM dNTP and 1 μL of PowerScript RT were added to the RNA/primer mixture. The sample was incubated further at 42° C. for 1.5 hours. The first strand cDNA synthesis reaction was terminated by adding 100 μL Tricine buffer and incubated at 72° C. for 7 minutes.

The cDNA encoding the heavy chain fragment of mAb GNX-8 was amplified from the first strand cDNAs obtained above by PCR using UPM (BD SMART RACE cDNA Amplification Kit) and a primer (SEQ ID NO:3) designed based on the 3'-end of the known $C_{H1}$ sequence of human IgG$^1$. The PCR reaction was carried out first for 5 cycles of 30 seconds at 94° C. and 3 minutes at 72° C., followed by 4 cycles of 30 seconds at 94° C., 30 seconds at 65° C., and 3 minutes at 72° C. Additional 26 cycles of gradient PCR reaction comprising 30 seconds at 94° C., 30 seconds at each of 56° C., 57.8° C., 59.9° C., 63.2° C., 65° C., and 3 minutes at 72° C. was added to ensure successful cloning.

The cDNA encoding the variable region of the aforesaid heavy chain fragment of mAb GNX-8 was re-amplified from 1 μL of the above 5 combined PCR reaction products in the presence of NUP (SMART RACE amplification kit) and a primer (SEQ ID NO:4) designed based on the middle region of the same $C_{H1}$ described above. The PCR reaction was performed as follows: preheating at 94° C. for 1 minutes, 25 cycles of PCR reaction comprising 15 seconds at 94° C., 30 seconds at 68° C., and a final extension step at 68° C. for 1 minutes. The amplified product was purified using a PCR purification kit (GeneMark) and the nucleotide sequence was determined using a primer (SEQ ID NO:5) designed based on the 5' end of the $C_{H1}$ sequence of human IgG$_1$.

Based on the sequence information, the full-length cDNA encoding mAb GNX-8's heavy chain was specifically amplified by PCR from previously prepared first strand cDNAs using newly synthesized primers to cover the beginning (SEQ ID NO:6), and the end (SEQ ID NO:7) of the heavy chain gene, with the BD Advantage™ 2 PCR Enzyme System (BD Biosciences). The PCR reaction was set as follows: preheating at 94° C. for 3 minutes, 35 cycles of PCR reaction comprising 40 seconds at 94° C., 30 seconds at 60° C. and 100 seconds at 72° C., and a final extension step at 72° C. for 5 minutes. Restriction enzyme recognition sequences were incorporated during PCR reaction at the 5' (EcoRI) and 3' (XbaI) ends to facilitate subsequent expression plasmids engineering. In addition, a T→G switch at position 4 (the nucleotide following ATG) was also introduced into the 5' end of heavy chain cDNA to fit Kozak rule.

To construct an expression plasmid, the amplified full-length heavy chain cDNA was first double digested with restriction enzymes EcoRI and XbaI. After gel purification, the recovered full-length heavy chain cDNA was then ligated to the pCIneo vector (Promega) at the same restriction enzyme cloning sites to obtain the expression vector pCI-GNX-8.H3. The inserted cDNA sequence was confirmed using a primer that hybridizes upstream of the multiple cloning site, i.e., SEQ ID NO:8, and a primer downstream of the multiple cloning site, i.e., SEQ ID NO:9. Sequencing confirmation was performed and the deduced nucleotide and amino acid sequences of mAb GNX-8's heavy chain variable region are shown in SEQ ID NOS:14 and 15, respectively. In addition, the peptide sequences of CDRs contained in the heavy chain variable region of mAb GNX-8 and their corresponding nucleotide sequences are shown in SEQ ID NOS: 18 to 23, respectively.

To identify the light chain cDNA sequences of mAb GNX-8, the light chain peptide of GNX-8 was subjected to mass spectrometry analysis and database search. According to the protein identification information, the light chain of mAb GNX-8 is homologous to the mouse X chain. A primer flanking the 5'-end of mouse lambda gene constant region, SEQ ID NO:10, was synthesized. A cDNA including the variable region and a part of the constant region of the light chain gene of mAb GNX-8 was amplified from the first strand cDNAs described above by touchdown PCR. After preheating at 94° C. for 2 minutes, the PCR reaction was carried out first for 5 cycles of 30 seconds at 94° C. and 90 seconds at 72° C., followed by 5 cycles of 30 seconds at 94° C., 30 seconds at 66° C., and 90 seconds at 72° C., and then 27 cycles of 30 seconds at 94° C., 30 seconds at 63° C., and 90 seconds at 72° C. The amplified PCR fragments were then introduced into the yT&A vector (Yeastern Biotech) for positive clone identification.

Four clones with the expected size were selected for sequence determination with a primer, SEQ ID NO:11. The results indicate that all four clones have the identical cDNA with a structure homologous to the 5'-end of known light chain genes.

To build an expression plasmid containing the light chain gene of mAb GNX-8, a new set of primers, SEQ ID NO:12 and SEQ ID NO:13, and the cloned cDNA in yT&A vector described above were used to prepare only the variable region of the light chain gene by PCR. The PCR reaction includes a preheating step at 94° C. for 2 minutes, 30 cycles of 94° C. for 30 seconds, 60° C. for 30 seconds and 72° C. for 45 seconds, and a final extension step at 72° C. for 3 minutes.

The amplified light chain variable region cDNA with incorporated EcoRI and BsiWI restriction enzyme cutting sites was digested with the respective enzymes. After agarose gel purification, the digested cDNA fragment was ligated to the same restriction enzyme cloning sites of the pCIck vector (a pCIneo based expression vector with the insertion of a human κ constant region between the XbaI and NotI restriction enzyme cloning sites) to give the light chain expression vector pCIck-GNX-8.mλ. Sequencing confirmation was performed and the deduced nucleotide and amino acid sequences of mAb GNX-8's light chain variable region are shown in SEQ ID NOS:16 and 17, respectively. In addition, the peptide sequences of CDRs contained in the light chain variable region of mAb GNX-8 and their corresponding nucleotide sequences are shown in SEQ ID NOS: 24 to 29, respectively.

To generate recombinant GNX-8 (rGNX-8) antibody, a single vector expressing both heavy chain and light chain genes of mAb GNX-8 was constructed with either the neomycin gene (pCIck-GNX-8-neo) or the DHFR gene (pCIck-GNX-8-DHFR) as a selection marker. The light chain vector pCIck-GNX-8.mλ was linearized by BglII digestion, followed by 5'-end dephosphorylation with calf intestine phosphatase (CIP) and then Klenow treatment to yield blunt ends. The heavy chain vector pCI-GNX-8.H3 was cleaved with restriction enzymes BglII and NgoMIV. The BglII-NgoMIV fragment containing the CMV promoter, full-length heavy chain cDNA and SV40 polyA was subjected to the Klenow treatment as well. After gel recovery, the heavy chain BglII-NgoMIV fragment was introduced into the linearized light chain vector by blunt end ligation to form the vector pCIck-GNX-8-neo. Subsequently, the vector pCIck-GNX-8-DHFR was generated by removing the neomycin gene via restriction enzymes NgoMIV/ClaI cleavage from the vector pCIck-GNX-8-neo and replacing with the DHFR gene. The DHFR minigene was prepared from the pdhfr3.2 vector (ATCC No. 37166) by restriction enzymes HindIII/SalI digestion. After gel recovery, both the isolated DHFR minigene and the NgoMIV/ClaI-cleaved pCIck-GNX-8-neo fragment were treated with Klenow to give blunt ends, and then linked together via blunt end ligation.

TABLE 3

Primers and Sequences

| Sequence (5' to 3') | SEQ ID NO |
|---|---|
| Glu Leu Leu Gly Gly | 1 |
| Met Ile Ser Arg Thr | 2 |
| gcatgtacta gttttgtcac aagatttggg | 3 |
| gtgcacgccg ctggtcaggg cgcctg | 4 |
| ggtgccaggg ggaagaccga tgg | 5 |
| cgaattcacc atggctgtct ccttcctc | 6 |
| gctctagatc atttacccgg agacagg | 7 |
| actcccagtt caattacagc | 8 |
| tggtttgtcc aaactcatc | 9 |
| gcatgtacta gttttgtcac aagatttggg | 10 |
| gttttcccag tcacgac | 11 |
| gcgaattcac catggcctgg acttcac | 12 |
| gccgtacgta ggacagtgac cttggttc | 13 |
| Gly Asp Ser Val Ser Ser Lys Ser Val Ala (Heavy chain CDR1) | 18 |
| ggggacagtg tctctagcaa gagtgttgct | 19 |
| Thr Tyr Tyr Arg Ser Lys Trp Tyr Asn (Heavy chain CDR2) | 20 |
| acatactaca ggtccaagtg gtataat | 21 |
| Ala Arg Asn Phe Asp Tyr (Heavy chain CDR3) | 22 |
| gcaagaaact ttgactac | 23 |
| Thr Gly Ala Val Thr Thr Asn Asn Tyr (Light chain CDR1) | 24 |
| actggggctg ttacaactaa taactat | 25 |
| Ala Thr Ser (Light chain CDR2) | 26 |
| gctaccagc | 27 |
| Ala Leu Trp Tyr Asn Thr His Phe Val (Light chain CDR3) | 28 |
| gctctatggt acaacaccca ttttgtt | 29 |

SEQ ID NO: 14
Length: 318
Type: DNA
(The coding sequence of the heavy
chain variable region of mAb GNX-8)
ggactggtga agccctcgca gaccctctca ctcacctgtg ccatctccgg ggacagtgtc tctagcaaga gtgttgcttg gaactggatc aggcagtccc cattgagagg ccttgagtgg ctgggaagga catactacag gtccaagtgg tataatgaat atgcagtatc tgtgaaaagt cgaataacca tcaatccaga cacatccaag aaccagttct ccctgcacct gaactctgtg actcccgagg acacggctgt gtattactgt gcaagaaact ttgactactg gggccaggga accctggtca ccgtctcc TABLE 3-continued

| Primers and Sequences |
|---|
| SEQ ID NO: 15<br>Length: 106<br>Type: amino acid<br>(The deduced amino acid sequence of the heavy chain variable region of mAb GNX-8)<br>Gly Leu Val Lys Pro Ser Gln Thr Leu Ser Leu Thr<br>Cys Ala Ile Ser Gly Asp Ser Val Ser Ser Lys Ser<br>Val Ala Trp Asn Trp Ile Arg Gln Ser Pro Leu Arg<br>Gly Leu Glu Trp Leu Gly Arg Thr Tyr Tyr Arg Ser<br>Lys Trp Tyr Asn Glu Tyr Ala Val Ser Val Lys Ser<br>Arg Ile Thr Ile Asn Pro Asp Thr Ser Lys Asn Gln<br>Phe Ser Leu His Leu Asn Ser Val Thr Pro Glu Asp<br>Thr Ala Val Tyr Tyr Cys Ala Arg Asn Phe Asp Tyr<br>Trp Gly Gln Gly Thr Leu Val Thr Val Ser |
| SEQ ID NO: 16<br>Length: 300<br>Type: DNA<br>(The coding sequence of the light chain variable region of mAb GNX-8)<br>ctcaccacag cacctggtgg aacagtcata ctcacttgtc<br>gctcaagtac tggggctgtt acaactaata actatgccaa<br>ctgggtccaa gaaaaaccag atcatttatt cactggtcta<br>atagatgcta ccagcaaccg agttccaggt gttcctgtca<br>gattctccgg ctccctgatt ggagacaagg ctgccctcac<br>catcacaggg gcacagactg aggatgatgc aatgtatttc<br>tgtgctctat ggtacaacac ccattttgtt ttcggcggtg<br>gaaccaaggt cactgtccta |
| SEQ ID NO: 17<br>Length: 100<br>Type: amino acid<br>(The deduced amino acid sequence of the light chain variable region of mAb GNX-8)<br>Leu Thr Thr Ala Pro Gly Gly Thr Val Ile Leu Thr<br>Cys Arg Ser Ser Thr Gly Ala Val Thr Thr Asn Asn<br>Tyr Ala Asn Trp Val Gln Glu Lys Pro Asp His Leu<br>Phe Thr Gly Leu Ile Asp Ala Thr Ser Asn Arg Val<br>Pro Gly Val Pro Val Arg Phe Ser Gly Ser Leu Ile<br>Gly Asp Lys Ala Ala Leu Thr Ile Thr Gly Ala Gln<br>Thr Glu Asp Asp Ala Met Tyr Phe Cys Ala Leu<br>Trp Tyr Asn Thr His Phe Val Phe Gly Gly Gly Thr<br>Lys Val Thr Val Leu |

Once the light and heavy chains of mAb GNX-8 were sequenced, the nucleic acid sequences can be recoded to optimize expression in, for example, specific human host cells.

Example 10

Transfectomas

NS0 cells were grown to a density of $1\times10^6$ cells/mL. The cells were maintained in exponential growth phase and medium was changed the day before transfection. On the day of transfection, $40\times10^6$ cells were washed. Then, 10 μg of linearized nucleic acid containing, for example, light chain DNA and linearized heavy chain DNA were added to the cell suspension (the total DNA volume should be less than 50 μL) and the culture was incubated on ice for 15 min. The DNA and cell mixture was transferred to a chilled cuvette (0.4 cm) and an electric pulse (750 V and 25 μF.) was applied. The cuvette was placed on ice immediately after the electric pulse and kept on ice for 10-15 min. The cells were collected and plated. The cells were incubated in a 5% CO2 incubator for 12-16 days or until colonies appear. The supernatant of the cell colonies or cells grown in suspension culture was tested by ELISA and positive transfectomas were cloned in fresh medium. To further screen the positive transfectomas, either titration ELISA or the BIAcore assay was conducted. Expanded transfectomas were maintained in shaker flasks and antibody or derivative thereof was collected from the supernatant.

Example 11

Pharmacokinetics

Rats were randomized into two groups (four rats/group). Animals received 1 or 10 mg/kg of mAb GNX-8 as a single i.v. bolus injection via a tail vein. Blood samples were collected at 0, 5, 15 and 30 minutes, and 1, 2, 4, 6, 24, 30, 72, 144, 168, 216, 240, 312, 336 and 360 hours. Sera were harvested and stored at −20° C. until the mAb GNX-8 concentration assay. mAb GNX-8 concentration was determined by ELISA.

GNX-8 was radiolabeled with $^{131}$I using the IODO-Gen method.

Nude mice were used for in vivo biodistribution and imaging studies. Five million Colo205 cells were inoculated subcutaneously. When the tumor reaches a size of 0.5 g, the biodistribution study was performed. For the biodistribution study, mice were injected in the tail vein with 10 μCi/2.3 μg $^{131}$I-labeled GNX-8. Five mice were sacrificed at 6, 24, 48, 72 and 96 hours after injection. Blood samples were taken just before the mice were sacrificed. Tumors and organs (brain, skin, muscle, bone, heart, lung, pancreas, eye, adrenal, tail, spleen, kidney, liver, bladder, stomach, small intestine and large intestine) were removed immediately and weighed. Presence of radiolabeled antibody in tumor, organ and blood were separately counted in a γ-counter (Packard). Standards were counted each time with the tissues and tumors. Tissue radioactivities were expressed as the percentage of injected dose per gram of organ (% ID/g).

Imaging studies were performed on a microSPECT single photon emission computerized tomography X-SPECT animal imaging system (Gamma Medica Inc. USA) and microCT X-ray computerized tomography. Nude mice bearing Colo205 tumors were i.v. injected with 200 mCi/5.5 mg/100 mL $^{131}$I-labeled GNX-8 via tail vein. Images were acquired at 1, 6, 24, 48, 72 and 96 hours. Pharmacokinetic (PK) studies were conducted for mAb GNX-8 in rats, SCID mice and nude mice following a single i.v. administration. Serum concentration of mAb GNX-8 was analyzed by ELISA.

A two-compartment model provided a good fit to the data and generated the PK parameters summarized in Tables 4 and 5. A dose-related increase in $C_{max}$ was observed following a single i.v. administration of 1.0 and 10 mg/kg mAb GNX-8 in rats. MAb GNX-8 was cleared from the serum in a terminal half-life of 3.81 and 4.98 days at a dose of 1 and 10 mg/kg, respectively.

The pharmacokinetic parameters of mAb GNX-8 after administration in nude mice and SCID mice with or without bearing Colo205 tumor presented with a $T_{1/2}$ that was about one day in both strains of mice with tumor. For non-tumor-bearing animals, $T_{1/2}$ values were 58.09 hr in SCID mice and 98.31 hr in nude mice, respectively. From the pharmacokinetic parameters, the $T_{1/2}$ was much longer in the non-tumor-bearing mice than in tumor-bearing mice.

TABLE 4

Pharmacokinetic parameters in rats

| Parameter | 1 mg/kg i.v. | 10 mg/kg i.v. |
|---|---|---|
| $T_{max}$ (minutes) | 5 | 5 |
| $C_{max}$ (µg/ml) | 9.49 | 102.08 |
| $T_{1/2}$ terminal (day) | 3.81 | 4.98 |

TABLE 5

Pharmacokinetic parameters in SCID mice and Nude mice (i.v. administration of 5 mg/kg GNX-8)

| | SCID mice | | Nude mice | |
|---|---|---|---|---|
| Tumor-bearing | + | − | + | − |
| $C_{max}$ (µg/ml) | 76.45 | 72.52 | 76.5 | 84.4 |
| $T_{max}$ (min) | 5 | 5 | 5 | 30 |
| $T_{1/2}$ (elimination) (hr) | 22.99 | 58.09 | 26.73 | 98.31 |

Biodistribution studies were done in nude mice bearing Colo205 xenografts to assess the in vivo tumor targeting activity and specificity of mAb GNX-8.

The highest level of $^{131}$I-GNX-8 radioactivity was detected in plasma at all time points (6 hr, 24 hr, 48 hr, 72 hr and 96 hr). At 6 hr, about 60% of the injected does per gram (% ID/g) was detected in plasma. At 48, 72 and 96 hours, the % ID/g for plasma was about 20%. The plasma level was significantly higher than in other organs, brain, skin, muscle, bone, heart, lung, pancreas, eye, adrenal gland, tail, spleen, kidney, liver, bladder, stomach, small intestine and large intestine, where the % ID/g at all time points in all organs did not exceed 5% ID/g. Radioactivity decreased over time in plasma and in the other organs, except the tumor. Plasma radioactivity decreased by about 70% between 6 and 96 hours.

Radioactivity of the tumor was initially higher than in normal organs. The highest tumor uptake was observed at 48 hours after $^{131}$I-GNX-8 injection, and maintained a steady state while the radioactivity of other organs decreased. Therefore, the tumor/organ ratios increased in other organs. Rapidly decreasing radioactivity was observed in plasma, heart, lung, adrenal gland, tail, spleen, kidney and liver between 6 and 24 hours. On the other hand, tumor/plasma ratios increased about 4 times from 6 to 96 hours after injection. No accumulation of $^{131}$I-GNX-8 in kidney was observed.

The in vivo tumor targeting activity in Colo205 tumor bearing nude mice was studied by imaging analysis. A time course experiment was done to monitor the distribution of $^{131}$I-GNX-8. The result also indicated that the majority of $^{131}$I-GNX-8 was located in blood, and tumor targeting was clearly visible from 24 to 72 hours after injection.

The in vivo data indicate that most GNX-8 was retained in blood after injection. There was no significant non-specific binding in various normal organs. Moreover, mAb GNX-8 targeted the Colo205 tumor rapidly after i.v. injection and maintained labeling at a steady state level over 96 hours.

Example 12

Toxicity

Single dose toxicity was performed in male and female BALB/c AnN Cr1 BR mice (6 mice/group) at 8-9 weeks of age. Mice were i.v. injected with mAb GNX-8 at a dose of 150 mg/kg or with vehicle alone (PBS). Body weight for all mice was measured on study days 1, 8 and 16 prior to sacrifice. Mice were observed daily for signs of morbidity or mortality.

Repeat dose toxicity was carried out in male Sprague-Dawley Cr1 CD (SD) rats (6 rats/group) at 8 weeks of age. Each group was administered vehicle (PBS) or 3, 15 or 75 mg/kg/dose of mAb GNX-8 twice weekly for 4 weeks. All animals were checked daily for mortality and any finding was recorded individually. Rats were weighed weekly during the pretreatment and treatment periods, and a final overnight fasting body weight was obtained at terminal sacrifice. Blood samples were collected at terminal sacrifice and evaluated for hematology and clinical chemistry parameters. The significance of differences in body weight and all tested parameters was determined by Student's t test.

To determine the cross reactivity of mAb GNX-8 on normal human tissues, a very high dose (150 µg/ml) of biotinylated GNX-8 was used. A tissue array with 72 human tissues (24 types of normal organs taken from 3 normal human individuals) (US Biomax FDA 801-1) were stained with GNX-8. Based on the results from the $C_{max}$ of the pharmacokinetic study, GNX-8 was used at 150 µg/ml to ensure that GNX 8 at $C_{max}$ would have no serious cross reactivity with normal human tissues. That concentration was much higher than regularly used in immunohistochemical studies.

Weak to moderate staining of GNX-8 was observed on several human tissues of epithelial origin, including mucosal epithelium of the gastrointestinal tract, epithelium cells of lactiferous ducts and keratinized cells of stratified squamous epithelium. According to the previous findings of Finstad et al. (*Clin. Cancer Res.*, 3:1433-1442, 1997), antibodies introduced into circulating blood showed specific localization to carcinoma cells and did not accumulate in the antigen-positive, adjacent normal epithelial cells. Also, antibodies do not traverse the basement membrane. Therefore, the staining in epithelial cells of ducts in normal tissue by GNX-8 is not considered a detriment.

Two additional studies were conducted for examining the cross reactivity of mAb GNX-8 on normal human blood cells. All tested blood cells from the four various blood type (ABO) donors show negative response with mAb GNX-8. The results support that mAb GNX-8 does not bind to blood cells. Therefore, mAb GNX-8 administered to the circulatory system should not cause damage to blood cells.

To address the safety of mAb GNX-8 in vivo, two studies were conducted to determine the acute and subacute toxicity effects.

The single dose toxicity of mAb GNX-8 was tested in BALB/c mice at a dose of 150 mg/kg. Mice were observed once daily and no deaths were found before scheduled sacrifice. All mice gained weight over the duration of the study and there was no significant difference in mean body weight gain between the GNX-8 treatment group and the control group.

The repeat dose toxicity of mAb GNX-8 was performed in Sprague Dawley Cr1 CD rats. Six animals of 8 weeks age were allocated to the groups. One group was administered vehicle (PBS) twice weekly for four weeks. Groups 2, 3 and 4 received mAb GNX-8 in PBS at 3, 15 and 75 mg/kg/dose, respectively, twice weekly for four weeks. All animals were examined daily for mortality and all findings were recorded. Rats were weighed weekly during the pretreatment and treatment periods and a final overnight fasting body weight was obtained at terminal sacrifice. Blood samples were collected at sacrifice and evaluated for hematology and clinical chemistry parameters. Significances of differences in body weight and all other measured parameters were analyzed by Student's t test.

There were no clinical signs of toxicity related to GNX-8 treatment. Analysis of final body weight gain indicated no difference between treatment and control groups. Blood samples of the control group and the high dose group were taken prior to euthanasia following an overnight fast, and were analyzed for hematology and clinical chemistry profiles.

There were no statistically significant differences between the high dose and the control groups for hemoglobin amount, hematocrit, RBC number, mean corpuscular volume, mean corpuscular hemoglobin and mean corpuscular hemoglobin concentration. The results indicate that no hematology toxicity is induced by repeated high-dose GNX-8 administration.

For clinical chemistry analyses, mean values for the parameters for the control and the high-dose groups are indicated in Table 6. A statistically significant increase in total protein is noted in the high dose group that might result from the repeated injections of high dose antibody. Additionally, a slight increase in albumin also is observed. However, the value is still within the range of normal limits for rats. The clinical chemistry data show no notable injury to metabolism and excretion function after repeated injection of high dose GNX-8.

Both hematology and clinical chemistry analyses verify the safety of repeated high dose GNX-8 administration over a four-week duration.

TABLE 6

Clinical Chemistry Analyses

| Items | Control Mean | SD | High dose mean | SD |
|---|---|---|---|---|
| Albumin (g/dL) | 3.3 | 0.4 | 3.9 | 0.2 |
| ALT(GPT) (U/L) | 118.6 | 50.0 | 67.6 | 6.0 |
| AST(GOT) (U/L) | 372.0 | 203.8 | 323.3 | 118.2 |
| Total bilirubin (mg/dL) | 0.3 | 0.1 | 0.6 | 0.2 |
| BUN (mg/dL) | 12.3 | 5.8 | 11.2 | 1.5 |
| Ca (mg/dL) | 11.0 | 0.2 | 11.2 | 0.2 |
| Cl$^-$ (mmol/L) | 108.0 | 2.1 | 106.0 | 2.2 |
| Cholesterol (mg/dL) | 96.6 | 9.2 | 86.4 | 18.7 |
| Creatinine (mg/dL) | 1.2 | 0.7 | 1.1 | 0.5 |
| K$^+$ (mmol/L) | 4.9 | 0.6 | 4.9 | 0.5 |
| Na$^+$ (mmol/L) | 144.6 | 2.7 | 148.2 | 4.2 |
| Phosphorous (mg/dL) | 8.4 | 0.6 | 7.4 | 0.9 |
| Total protein (g/dL) | 6.3 | 0.3 | 7.1 | 0.2 |

Example 13

Scale-Up

To obtain a stable cell line for large scale production of GNX-8, NS0 and CHO cell lines expressing recombinant GNX-8 (rGNX-8) were obtained. Briefly, cDNAs encoding both the heavy and light chains of mAb GNX-8 were cloned from the original hybridoma. The isolated antibody genes then were reassembled in expression vectors. The molecular weight of rGNX-8 purified from media conditioned by transfected NS0 cells was confirmed by SDS-PAGE. The specificity, binding activity and efficacy of rGNX-8 and the original mAb GNX-8 were compared by HPTLC, immunostaining, flow cytometry and CDC assay.

There were no differences between the original and recombinant GNX-8 antibodies.

The N-glycosylation profiles of rGNX-8 and mAb GNX-8 then were analyzed by MALDI-MS.

The data illustrate a highly similar N-linked sugar pattern between the two antibodies. Almost all N-glycans of the two antibodies contained the core fucosylation structure, but no terminal sialic acids.

Dihydrofolate reductase deficient Chinese hamster ovary (CHO/dhfr-) cells (ATCC CRL-9096) were maintained in IMDM containing 5% FBS and supplemented with 100 nM hypoxanthine and 16 µM thymidine. To prepare recombinant GNX-8 production cell lines, expression vector pCIck-GNX-8 DHFR was linearized by restriction enzyme BamHI and the concentration of recovered DNA in solution was determined by $OD_{260}$ absorbance. Approximately $1.2 \times 10^6$ CHO/dhfr-cells are transfected with 10 µg linearized DNA and 30 µL of Fugene6 transfection reagent (Roche) according to the manufacturer's instructions. After 48 hours, the culture medium was replaced with 5% dialyzed fetal bovine serum containing IMDM for transfectant selection. The selection was continued for approximately two weeks until stable colonies were obtained. Multiple colonies were picked and cultured under the same selective medium in 48-well plates. Individual CHO clones were screened for rGNX-8 expression by antigen-specific ELISA using HRP-labeled anti human IgG(Fc) antibodies as the secondary antibody.

A CHO clone that expressed high levels of antibody was selected for subsequent gene amplification with methotrexate (MTX). Gene amplification in 10 nM of MTX resulted in more than a 30-fold increase of rGNX-8 secretion. The stable CHO clone was named CHO-rGNX-8.5M10.

CHO-rGNX-8.5M10 cells were later adapted to serum-free culture in shaking flasks and achieved a maximum yield of approximately 120 µg/mL of rGNX 8 over a 14-day culture. The culture supernatant was collected and purified by Protein A chromatography. The rGNX-8 antibody purified from the CHO culture supernatant by Protein A chromatography revealed the expected light chain and heavy chain peptide bands on SDS-PAGE.

Example 14

Monoclonal Antibody GNX-10

Monoclonal antibody GNX-10 was generated from the same KM mouse as mAb GNX-8 described above, except for using different mouse myeloma cell lines as the fusion partner, namely, NS-1 and FO cell lines were used in generating the antibody-producing hybridoma clones GNX-8 and GNX-10, respectively.

The epitope of mAb GNX-10 was specified as extended Type I chain $Le^b$-$Le^a$ based on the results of HPTLC immunostaining and ELISA.

1. Sequence Analysis of mAb GNX-10

The amino acid sequences of both the heavy and light chain variable regions of mAb GNX-10 are very similar to those of mAb GNX-8. The amino acid sequences of the heavy and light chains of mAb GNX-10 are shown in SEQ ID NOS: 30 and 34, respectively, and the CDR regions contained therein are shown in SEQ ID NOS:31-33 and SEQ ID NOS:35-37.

```
The amino acid sequence of the heavy chain
variable region of mAb GNX-10
                                  (SEQ ID NO: 30)
G L V K P S Q T L S L T C T I S G D S V S S N T V

A W N W I R Q S P S R G L E W L G R T Y Y R S K W

Y N D Y A I F V K S R I T F N P D T S K N Q F S

L H L N S V T P E D T A V Y Y C A R N F D S W G

Q G T L V T V S
(CDR regions are underlined and marked with bold-
letter.)

The amino acid sequence of the light chain
variable region of mAb GNX-10
                                  (SEQ ID NO: 34)
L T T S P G G T V I L T C R S S T G A V T T D N Y

A N W V Q E K P D H L F T G L I D A T S N R V P G

V P V R F S G S L I G D K A A L T I T G A Q T E

D D A M Y F C A L W Y N T H F V F G G G T K V

T V L
(CDR regions are underlined and marked with bold-
letter.)
```

Alignments of the amino acid sequences of the heavy and light chain variable regions of mAbs GNX-8 and GNX-10 are shown below, in which 9 amino acid differences (i.e., the amino acid residues that are marked by box and bold-letter) are in the heavy chain variable region and 2 amino acid differences in the light chain variable region. There are 4 amino acid differences located in predicted CDR regions of the heavy chain variable region and only one amino acid difference in predicted CDR region (i.e., the underlined regions) of the light chain variable region.

cation kit (Clontech), in which primers GNX8hVH5Eco (5'-cgaattcaccatggctgtctccttcctc-3') (SEQ ID NO: 38) and hh-3 (5'-gtgcacgccgctggtcagggcgcctg-3') (SEQ ID NO: 39) were used to amplify the heavy chain variable region cDNA, and primers GNX8mvlSEco (5'-gcgaattcaccatggcctggacttcac-3') (SEQ ID NO: 40) and GNX8mvlASBwi (5'-gccgtacgtagga-cagtgaccttggtta-3') (SEQ ID NO: 41) were used to amplify the light chain variable region cDNA.

The heavy and light chain variable regions cDNAs thus obtained were inserted to heavy and light chain expression vectors, respectively. The expression vectors were derived from GNX8 expression vectors pCI-GNX-8.H3 and pCIck-GNX-8.mλ. Both expression vectors were co-transfected into FreeStyle 293F cells (Invitrogen) to transiently express recombinant GNX-10 (rGNX-10) antibody. Dual vector of GNX8 pCI-GNX-8.H3 was included as a control. Culture supernatants were harvested and directly used for characterization or purified by Protein A. Antibody concentrations were determined by human IgG-specific ELISA.

Since the sequences of mAb GNX-8 and mAb GNX-10 are very similar, the applicants further generated 2 cross-matched antibodies (i.e., hybrid antibody "GNX8H/GNX10L" constituted of GNX-8 heavy chain and GNX-10 light chain, and hybrid antibody "GNX10H/GNX8L" constituted of GNX-10 heavy chain and GNX-8 light chain) and found that these two hybrid antibodies exhibited binding specificity substantially to that of mAbs GNX-8 and GNX-10 (data not shown).

3. Comparison of mAbs GNX-8 and GNX-10

A. TLC immunostaining

Colo205 neutral glycosphigolipids (2 μL/sample) were spotted on HPTLC plate (Merck, 1.05642, silica gel 60 F254), and developed with a mobile phase containing chloroform:methanol:water with a ratio of 50:40:10 (V:V:V). For glycan staining of glycolipids, 0.2% orcinol (Sigma, O-1875) in 10% $H_2SO_4$ were sprayed onto a HPTLC plate and incubated for 10 minutes at 110° C. in oven. For immunostaining, the HPTLC plate was first fixed with 0.5% poly(isobutyl methacrylate) (Aldrich, 181544) in chloroform:hexane (1:9,

```
Alignment of heavy chain variable region (mAb GNX-8 vs. mAb GNX-10)

GNX-10  GLVKPSQTLSLTCTISGDSVSSNTVAWNWIRQSPSRGLEWLGRTYYRSKWYNDYAIFVKS

::::::::::::: :::::::  ::::::::::::: ::::::::::::::::  :::

GNX-8   GLVKPSQTLSLTCAISGDSVSSKSVAWNWIRQSPLRGLEWKGRTYYRSKWYNEYAVSVKS

GXN-10  RITFNPDTSKNQFSLHLNSVTPEDTAVYYCARNFDSWGQGTLVTVSSASTKGP

::: :::::::::::::::::::::::::::::::::: :::::::::::::

GXN-8   RITINPDTSKNQFSLHLNSVTPEDTAVYYCARNFDYWGQGTLVTVSSASTKGP

Alignment of light chain variable region (mAb GNX-8 vs. mAb GNX-10)

GXN-10  LTTSPGGTVILTCRSSTGAVTTDNYANWVQEKPDHLFTGLIDATSNRVPG

::: ::::::::::::::::::::: ::::::::::::::::::::::::

GXN-8   LTTAPGGTVILTCRSSTGAVTTNNYANWVQEKPDHLFTGLIDATSNRVPG

GXN-10  VPVRFSGSLIGDKAALTITGAQTEDDAMYFCALWYNTHFVFGGGTKVTVL

::::::::::::::::::::::::::::::::::::::::::::::::::

GXN-8   VPVRFSGSLIGDKAALTITGAQTEDDAMYFCALWYNTHFVFGGGTKVTVL
```

2. Cloning and Expression of cDNA Encoding mAb GNX-10 in FreeStyle 293F Cell

The heavy and light chain variable region cDNAs of mAb GNX-10 were cloned using SMART RACE cDNA amplifi- V:V) for 45 seconds, followed by blocking for 10 minutes in 3% BSA/PBS. The plates were then washed with PBS and incubated with the primary antibody at room temperature for 1 hr, followed by HRP-labeled secondary antibody at room temperature for 1 hr. Immunostaining HRP-1000 kit (Konica Minolta, #130990) was used for color development according to manufacturer's protocol.

Referring to FIG. 1, mAbs GNX-8 and GNX-10 bind to substantially the same epitope band.

B. Antigen Specific ELISA

B1) Using Colo205 Neutral GSLs as Antigen 96-well ELISA plates (Costar, Corning, N.Y.) coated with 1 µg/well of Colo205 neutral glycosphigolipids (GSLs). GSLs were dissolved in ethanol and directly dried on wells. Wells were blocked with 1% bovine serum. Diluted mAbs GNX-8 and GNX-10 were added into wells (100 µL/well) in duplicate, incubated at 37° C. for 30 min. Antibodies bound to the coated GSLs were detected by mouse anti-human IgG (Fc)-HRP (Southern Biotech, #9040-05) at 1:5000 dilution (100 µL/well), incubated at 37° C. for 30 min, followed by color development with TMB (KPL, Cat#53-00-03). The reaction was stopped by 0.5N HCl and was read by ELISA reader at 450 nm.

Figure 2:
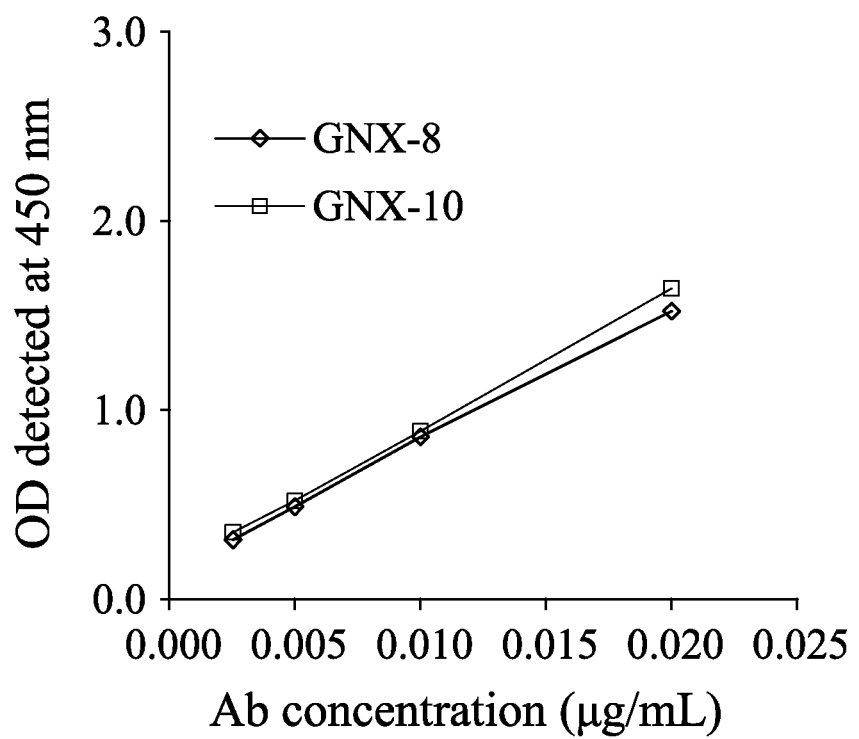
FIG. 2 shows the binding specificity of GNX-8 and GNX-10 to Colo205 neutral glycosphingolipids, in which mAbs GNX-8 and GNX-10 were examined by ELISA using mouse anti-human IgG (Fc)-HRP as the secondary antibody and 3,3',5,5'-tetramethylbenzidine (TMB) as the substrate for color development, which was read by an ELISA reader at 450 nm.

It can be seen from FIG. 2 that the binding behavior of mAb GNX-10 to Colo205 neutral glycosphigolipids is closely similar to that of mAb GNX-8.

B2) Using Biotinylated Leb-Lea as Antigen 96-well ELISA plates were sequentially coated with 0.3 µg/well ImmunoPure Streptavidin (Thermo scientific, Cat. #21125) and biotinylated $Le^b$-$Le^a$-Lac prepared by the applicants' lab. Wells were blocked with 0.1% skim milk. MAbs GNX-8 and GNX-10 were added into wells (100 µL/well) in duplicate and incubated at 37° C. for 30 min, followed by incubation with mouse anti-human IgG (Fc)-HRP (Southern Biotech, #9040-05) at 1:5000 dilution (100 µL/well) for 30 min. Color development with TMB (KPL, Cat#53-00-03) was stopped by 0.5N HCl and read by ELISA reader at 450 nm.

Figure 3:
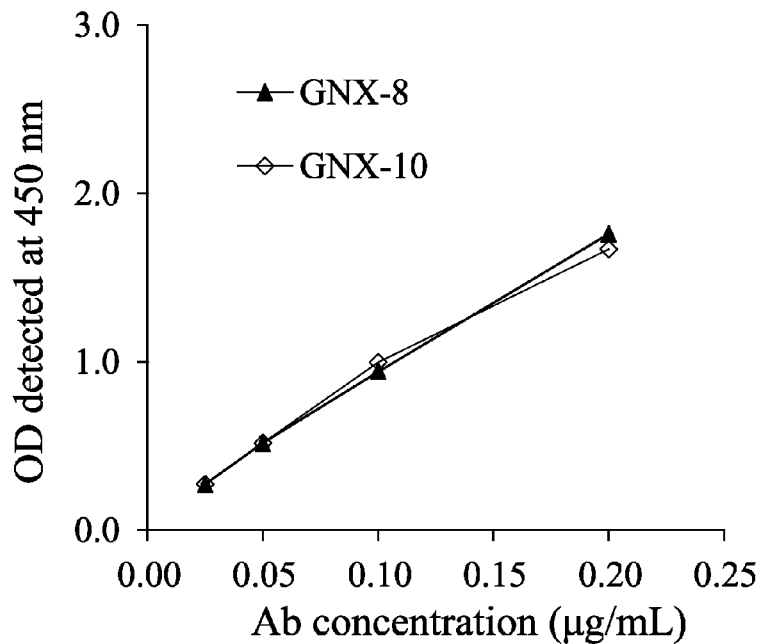
FIG. 3 shows the respective binding specificities of mAbs GNX-8 and GNX-10 to $Le^b$-$Le^a$-Lac, in which mAbs GNX-8 and GNX-10 were added into the wells of 96-well ELISA plates sequentially coated with ImmunoPure Streptavidin and biotinylated $Le^b$-$Le^a$-Lac and then examined by ELISA using mouse anti-human IgG (Fc)-HRP as the secondary antibody and TMB as the substrate for color development, which was read by an ELISA reader at 450 nm.

Like FIG. 2, the binding behavior of mAb GNX-10 to $Le^b$-$Le^a$-Lac as shown in FIG. 3 is closely similar to that of mAb GNX-8.

B3) ADCC Assay

The ADCC assay was performed substantially according to the procedures described in Example 4, in which Colo205 cells were used as target cells, and human peripheral blood mononuclear cells (PBMC) as effector cells. Blood donors were selected from healthy volunteers of GlycoNex's employees.

Figure 4:
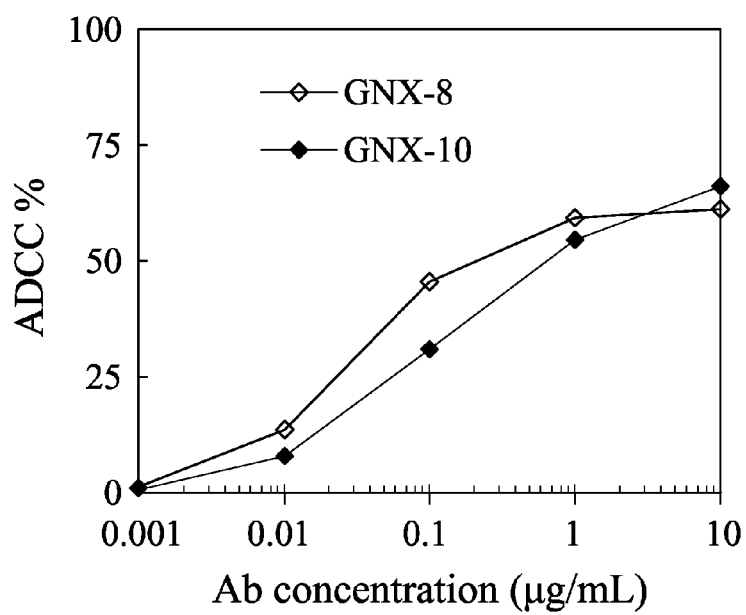
FIG. 4 shows the respective antibody-dependent cellular cytotoxicity (ADCC) activities of mAbs GNX-8 and GNX-10 as determined by dehydrogenase (LDH) release assay described in Example 4, infra.

It can be seen from FIG. 4 that the ADCC activity of mAb GNX-10 to Colo205 cells is similar to that of mAb GNX-8.

B4) CDC Assay

The CDC assay was performed substantially according to the procedures described in Example 4, in which Colo205 cells were used as target cells, and cells treated with normal human IgGs purified from normal human serum served as a negative control.

Figure 5:
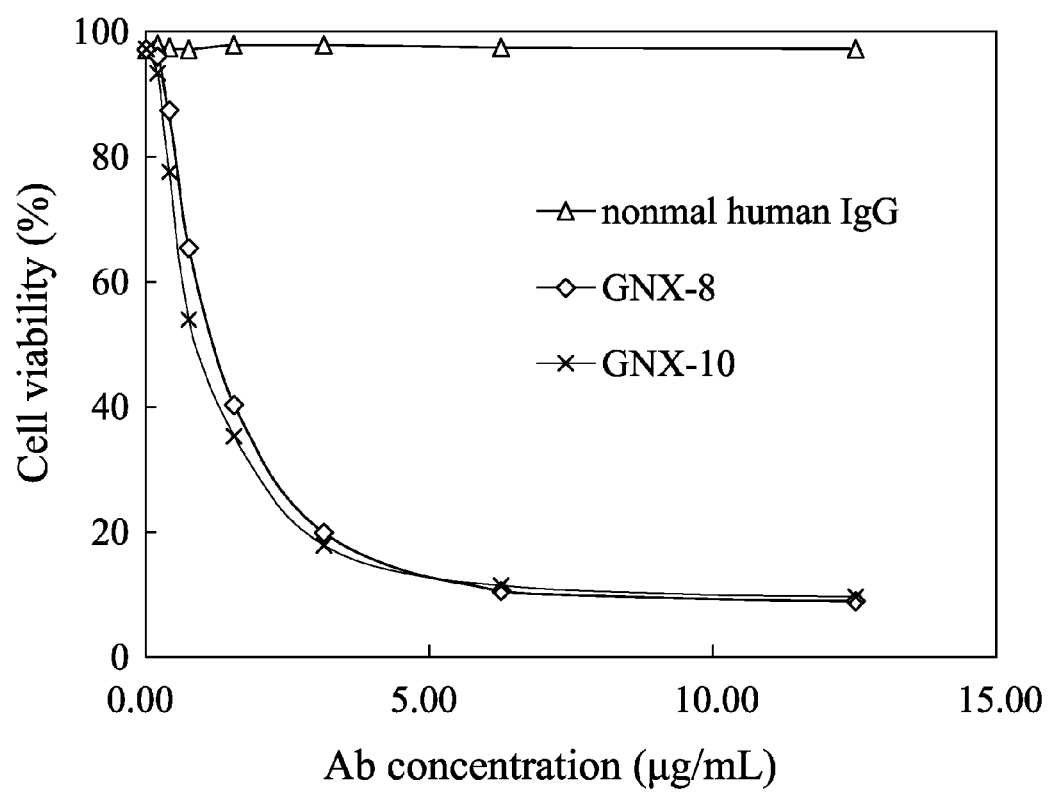
FIG. 5 shows the respective complement-dependent cytotoxicity (CDC) activities of mAbs GNX-8 and GNX-10 on human colon cancer cell line Colo205, as described in Example 4, infra., in which cancer cells treated with normal human IgGs served as a negative control.

It can be seen from FIG. 5 that the CDC activity of mAb GNX-10 to Colo205 cells is similar to that of mAb GNX-8.

Those skilled in the art will recognize, or be able to ascertain using no more than routine experimentation, many equivalents to the specific embodiments of the invention described herein. Such equivalents are intended to be encompassed by the following claims.

---

We claim:

1. An isolated binding moiety which specifically binds to an epitope comprising an extended Type I chain comprising Le$^b$, wherein the binding moiety comprises:
   (a) a heavy chain variable region ($V_H$) that includes:
      (i) a $V_H$ CDR1 sequence: Gly-Asp-Ser-Val-Ser-Ser-$X_1$-$X_2$-Val-Ala (SEQ ID NO:42), wherein $X_1$ is selected from the group consisting of Asn and Lys, and $X_2$ is selected from the group consisting of Thr and Ser;
      (ii) a $V_H$ CDR2 sequence: Thr-Tyr-Tyr-Arg-Ser-Lys-Trp-Tyr-Asn (SEQ ID NO:32); and
      (iii) a $V_H$ CDR3 sequence: Ala-Arg-Asn-Phe-Asp-$X_3$ (SEQ ID NO:43), wherein $X_3$ is selected from the group consisting of Ser and Tyr; and
   (b) a light chain variable region ($V_L$) that includes:
      (i) a $V_L$ CDR1 sequence: Thr-Gly-Ala-Val-Thr-Thr-$X_4$-Asn-Tyr (SEQ ID NO:44), wherein $X_4$ is Asp;
      (ii) a $V_L$ CDR2 sequence: Ala-Thr-Ser (SEQ ID NO:36); and
      (iii) a $V_L$ CDR3 sequence: Ala-Leu-Trp-Tyr-Asn-Thr-His-Phe-Val (SEQ ID NO:37);
   wherein the binding moiety is an antibody or an antigen-binding fragment thereof.

2. The isolated binding moiety of claim 1, wherein the epitope comprises an extended Type I chain Le$^b$-Le$^a$.

3. The isolated binding moiety of claim 1, wherein the epitope is expressed on a cancer cell of primary and metastatic colorectal cancers, breast cancers, pancreas cancers, lung cancers, stomach cancers, esophagus cancers, and prostate cancers.

4. The isolated binding moiety of claim 3, wherein the cancer cell is an epithelial cell.

5. The isolated binding moiety of claim 1, wherein the binding moiety binds to glycosphigolipids, glycoproteins or glycans present on or isolated from cancer cells expressing the epitope.

6. The isolated binding moiety of claim 1, wherein the binding moiety is an antibody or an antigen-binding fragment thereof, said antibody being selected from the group consisting of polyclonal antibodies, monoclonal antibodies, chimeric antibodies, humanized antibodies, and human antibodies.

7. The isolated binding moiety of claim 6, wherein the binding moiety is an antigen-binding fragment of the antibody, said fragment being selected from the group consisting of Fab fragments, Fab' fragments, F(ab')$_2$ fragments, Fv fragments, disulfide-linked Fv (dsFv) fragments, single domain antibodies, and single chain Fv (scFv) molecules.

8. The isolated binding moiety of claim 7, wherein the binding moiety is a scFv molecule.

9. The isolated binding moiety of claim 1, wherein the binding moiety comprises a $V_H$ CDR1 sequence of SEQ ID NO:31, a $V_H$ CDR2 sequence of SEQ ID NO:32, a $V_H$ CDR3 sequence of SEQ ID NO:33, a $V_L$ CDR1 sequence of SEQ ID NO:35, a $V_L$ CDR2 sequence of SEQ ID NO:36, and a $V_L$ CDR3 sequence of SEQ ID NO:37.

10. The isolated binding moiety of claim 1, wherein the binding moiety comprises a $V_H$ CDR1 sequence of SEQ ID NO:18, a $V_H$ CDR2 sequence of SEQ ID NO:20, a $V_H$ CDR3 sequence of SEQ ID NO:22, a $V_L$ CDR1 sequence of SEQ ID NO:35, a $V_L$ CDR2 sequence of SEQ ID NO:36, and a $V_L$ CDR3 sequence of SEQ ID NO:37.

11. The isolated binding moiety of claim 1, wherein the binding moiety comprises a heavy chain variable region of SEQ ID NO:30 and a light chain variable region of SEQ ID NO:34.

12. The isolated binding moiety of claim 1, wherein the binding moiety comprises a heavy chain variable region of SEQ ID NO:15 and a light chain variable region of SEQ ID NO:34.

13. A pharmaceutical or diagnostic composition comprising the isolated binding moiety of claim 1.

14. The pharmaceutical or diagnostic composition of claim 13, wherein the binding moiety is labeled.

* * * * *